(12) United States Patent
Baldauf-Lenschen et al.

(10) Patent No.: US 12,136,484 B2
(45) Date of Patent: *Nov. 5, 2024

(54) METHOD AND APPARATUS UTILIZING IMAGE-BASED MODELING IN HEALTHCARE

(71) Applicant: ALTIS LABS, INC., Toronto (CA)

(72) Inventors: Felix Baldauf-Lenschen, Toronto (CA); Sally Daub, Coldwater (CA); Alyssa Randall, Toronto (CA); Shazia Akbar, Toronto (CA)

(73) Assignee: ALTIS LABS, INC., Toronto (CA)

( * ) Notice: Subject to any disclaimer, the term of this patent is extended or adjusted under 35 U.S.C. 154(b) by 499 days.

This patent is subject to a terminal disclaimer.

(21) Appl. No.: 17/520,289

(22) Filed: Nov. 5, 2021

(65) Prior Publication Data

US 2023/0145034 A1 May 11, 2023

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0016* (2013.01); *G06T 7/10* (2017.01); *G16H 50/20* (2018.01);
(Continued)

(58) Field of Classification Search
CPC . G06T 2207/20081; G06T 2207/20084; G06T 2207/30048; G06T 2207/30096;
(Continued)

(56) References Cited

U.S. PATENT DOCUMENTS 5,305,204 A 4/1994 Ohhashi
5,785,042 A 7/1998 Kao
(Continued)

FOREIGN PATENT DOCUMENTS

CN 106295139 A 1/2017
CN 106551704 A 4/2017
(Continued)

OTHER PUBLICATIONS

Andersch, Michael; Inference: The Next Step in GPU-Accelerated Deep Learning; https://devblogs.nvidia.com/parallelforall/inference-next-step-gpu-accelerated-deep-learning/; Nov. 11, 2015; 7 pages.
(Continued)

*Primary Examiner* — Ajibola A Akinyemi
(74) *Attorney, Agent, or Firm* — Garlick & Markison; Bruce E. Stuckman

(57) ABSTRACT

Aspects of the subject disclosure may include, for example, obtaining pre-treatment images; analyzing the pre-treatment images according to an imaging model that includes a machine learning model; predicting, according to the analyzing the pre-treatment images, one or more clinical variables; obtaining on-treatment images; analyzing the on-treatment images according to the imaging model; predicting, based on the analyzing the on-treatment images, the one or more clinical variables for the on-treatment images; and presenting event estimation information in a graphical user interface. Other embodiments are disclosed.

19 Claims, 36 Drawing Sheets

(51) Int. Cl.
*G06T 7/10* (2017.01)
*G16H 50/20* (2018.01)
*G16H 50/30* (2018.01)
*G16H 50/70* (2018.01)

(52) U.S. Cl.
CPC ............ *G16H 50/30* (2018.01); *G16H 50/70* (2018.01); *G06T 2200/24* (2013.01); *G06T 2207/10081* (2013.01); *G06T 2207/20081* (2013.01); *G06T 2207/20084* (2013.01); *G06T 2207/30096* (2013.01)

(58) Field of Classification Search
CPC ............ G06T 5/70; G06T 2207/10081; G06T 7/0014; G06T 7/0016; G06T 7/10; G06T 2200/24; G06T 2207/10024; G06T 2207/30016; G06T 2207/30024
USPC .......................................................... 382/128
See application file for complete search history.

(56) References Cited

U.S. PATENT DOCUMENTS

| | | | |
|---|---|---|---|
| 6,058,322 A | 5/2000 | Nishikawa |
| 6,452,677 B1 | 9/2002 | Do |
| 6,466,687 B1 | 10/2002 | Uppaluri |
| 6,470,092 B1 | 10/2002 | Li |
| 6,524,246 B1 | 2/2003 | Kelly |
| 6,549,646 B1 | 4/2003 | Yeh |
| 6,754,380 B1 | 6/2004 | Suzuki |
| 6,819,790 B2 | 11/2004 | Suzuki |
| 6,871,174 B1 | 3/2005 | Dolan |
| 6,901,277 B2 | 5/2005 | Kaufman |
| 6,937,776 B2 | 8/2005 | Li |
| 7,054,473 B1 | 5/2006 | Roehrig |
| 7,123,762 B2 | 10/2006 | Giger |
| 7,418,123 B2 | 8/2008 | Giger |
| 7,813,822 B1 | 10/2010 | Hoffberg |
| 7,860,287 B2 | 12/2010 | Zahlmann |
| 8,120,804 B2 | 2/2012 | Isobe et al. |
| 8,121,362 B2 | 2/2012 | Zhan |
| 8,303,505 B2 | 11/2012 | Webler |
| 8,331,637 B2 | 12/2012 | Bar-Aviv |
| 8,379,950 B2 | 2/2013 | Ye |
| 8,600,133 B2 | 12/2013 | Buelow |
| 8,873,818 B1 | 10/2014 | Ostermann |
| 8,885,898 B2 | 11/2014 | Liu |
| 8,949,079 B2 | 2/2015 | Rao |
| 8,953,858 B2 | 2/2015 | Becker |
| 9,165,360 B1 | 10/2015 | Bates |
| 9,349,178 B1 | 5/2016 | Itu |
| 9,501,863 B1 | 11/2016 | Fram |
| 9,569,736 B1 | 2/2017 | Ghesu |
| 9,579,518 B2 | 2/2017 | Gertner |
| 9,589,231 B2 | 3/2017 | Csurka |
| 9,613,416 B1 | 4/2017 | Bates |
| 9,760,978 B1 | 9/2017 | Lu |
| 9,792,682 B2 | 10/2017 | Gluncic |
| 9,805,072 B2 | 10/2017 | Spiess |
| 9,888,969 B2 | 2/2018 | Cohen et al. |
| 10,019,654 B1 | 7/2018 | Pisoni |
| 10,140,421 B1 | 11/2018 | Bernard |
| 10,140,675 B2 | 11/2018 | Sowden |
| 10,152,571 B1 | 12/2018 | Lyman |
| 10,162,866 B2 | 12/2018 | Fink |
| 10,304,198 B2 | 5/2019 | Yan |
| 10,340,041 B2 | 7/2019 | Chan |
| 10,340,044 B2 | 7/2019 | Yao |
| 10,360,999 B2 | 7/2019 | Bernard |
| 10,366,183 B2 | 7/2019 | Wilson |
| 10,410,092 B1 | 9/2019 | Chen |
| 10,452,813 B2 | 10/2019 | Sorenson |
| 10,499,857 B1 | 12/2019 | Nguyen |
| 10,540,554 B2 | 1/2020 | Guo |
| 10,541,050 B2 | 1/2020 | Lyman |
| 10,546,403 B2 | 1/2020 | Grady |
| 10,553,311 B2 | 2/2020 | Lyman |
| 10,553,312 B2 | 2/2020 | Bernard |
| 10,706,970 B1 | 7/2020 | Florissi |
| 10,729,351 B1 | 8/2020 | Chen |
| 10,748,652 B2 | 8/2020 | Yao |
| 10,755,811 B1 | 8/2020 | Bernard |
| 10,783,990 B2 | 9/2020 | Lyman |
| 10,811,134 B2 | 10/2020 | Bernard |
| 10,818,386 B2 | 10/2020 | Yao |
| 10,819,881 B1 | 10/2020 | Smolyar |
| 10,867,697 B2 | 12/2020 | Lyman |
| 10,878,948 B2 | 12/2020 | Lyman |
| 10,878,949 B2 | 12/2020 | Prosky |
| 10,896,747 B2 | 1/2021 | Lyman |
| 10,896,753 B2 | 1/2021 | Lyman |
| 10,902,940 B2 | 1/2021 | Lyman |
| 10,910,097 B2 | 2/2021 | Bernard |
| 10,916,337 B2 | 2/2021 | Poblenz |
| 10,930,387 B2 | 2/2021 | Lyman |
| 10,943,681 B2 | 3/2021 | Yao |
| 11,011,257 B2 | 5/2021 | Lints |
| 11,056,220 B2 | 7/2021 | Lyman |
| 11,087,872 B2 | 8/2021 | Bernard |
| 11,107,564 B2 | 8/2021 | Poblenz |
| 11,114,189 B2 | 9/2021 | Prosky |
| 11,145,059 B2 | 10/2021 | Yao |
| 11,152,089 B2 | 10/2021 | Lyman |
| 11,158,406 B2 | 10/2021 | Lyman |
| 11,177,034 B2 | 11/2021 | Lyman |
| 11,200,969 B2 | 12/2021 | Lyman |
| 11,211,153 B2 | 12/2021 | Lyman |
| 11,211,161 B2 | 12/2021 | Lyman |
| 11,222,717 B2 | 1/2022 | Lyman |
| 11,257,575 B2 | 2/2022 | Lyman |
| 11,282,198 B2 | 3/2022 | Lyman |
| 11,282,595 B2 | 3/2022 | Yao |
| 11,295,840 B2 | 4/2022 | Lyman |
| 11,315,665 B2 | 4/2022 | Poblenz |
| 11,322,232 B2 | 5/2022 | Lyman |
| 11,322,233 B2 | 5/2022 | Yao |
| 11,328,798 B2 | 5/2022 | Lyman |
| 11,348,669 B2 | 5/2022 | Lyman |
| 2002/0186818 A1 | 12/2002 | Arnaud |
| 2003/0016850 A1 | 1/2003 | Kaufman |
| 2003/0220816 A1 | 11/2003 | Giesler |
| 2003/0229278 A1 | 12/2003 | Sinha |
| 2004/0064029 A1 | 4/2004 | Summers |
| 2004/0100476 A1 | 5/2004 | Morita |
| 2004/0147840 A1 | 7/2004 | Duggirala |
| 2004/0181431 A1 | 9/2004 | Kuth |
| 2004/0249676 A1 | 12/2004 | Marshall |
| 2004/0252870 A1 | 12/2004 | Reeves |
| 2005/0010445 A1 | 1/2005 | Krishnan |
| 2005/0027566 A1 | 2/2005 | Haskell |
| 2005/0105788 A1 | 5/2005 | Turek |
| 2005/0114380 A1 | 5/2005 | Eldar |
| 2005/0137910 A1 | 6/2005 | Rao |
| 2005/0143641 A1 | 6/2005 | Tashiro |
| 2005/0207630 A1 | 9/2005 | Chan |
| 2005/0210015 A1 | 9/2005 | Zhou |
| 2005/0213832 A1 | 9/2005 | Schofield |
| 2005/0251013 A1 | 11/2005 | Krishnan |
| 2005/0267351 A1 | 12/2005 | Humphrey |
| 2005/0283450 A1 | 12/2005 | Matsugu |
| 2006/0018524 A1 | 1/2006 | Suzuki |
| 2006/0116908 A1 | 6/2006 | Dew |
| 2006/0122480 A1 | 6/2006 | Luo |
| 2006/0228015 A1 | 10/2006 | Brockway |
| 2006/0277073 A1 | 12/2006 | Heilbrunn |
| 2007/0004980 A1 | 1/2007 | Warner |
| 2007/0014454 A1 | 1/2007 | Sawyer |
| 2007/0036402 A1 | 2/2007 | Cahill |
| 2007/0052716 A1 | 3/2007 | Jabri |
| 2007/0052734 A1 | 3/2007 | Skinner |
| 2007/0053483 A1 | 3/2007 | Nagata |
| 2007/0177779 A1 | 8/2007 | Dennison |
| 2008/0004505 A1 | 1/2008 | Kapit |
| 2008/0008366 A1 | 1/2008 | Desh et al. |

(56) References Cited

U.S. PATENT DOCUMENTS

| | | |
|---|---|---|
| 2008/0015418 A1 | 1/2008 | Jarrell |
| 2008/0021834 A1 | 1/2008 | Holla |
| 2008/0052112 A1 | 2/2008 | Zahlman |
| 2008/0069446 A1 | 3/2008 | Ancelin |
| 2008/0154848 A1 | 6/2008 | Haslam |
| 2008/0195600 A1 | 8/2008 | Deakter |
| 2008/0201280 A1 | 8/2008 | Martin |
| 2008/0205717 A1 | 8/2008 | Reeves |
| 2008/0243539 A1 | 10/2008 | Barish et al. |
| 2008/0267467 A1 | 10/2008 | Sokulin et al. |
| 2008/0267483 A1 | 10/2008 | Zhan |
| 2008/0292152 A1 | 11/2008 | Nekrich |
| 2009/0060120 A1 | 3/2009 | Mukumoto |
| 2009/0080731 A1 | 3/2009 | Krishnapuram |
| 2009/0080734 A1 | 3/2009 | Moriya |
| 2009/0089098 A1 | 4/2009 | Schoenberg |
| 2009/0097723 A1 | 4/2009 | Washburn et al. |
| 2009/0132636 A1 | 5/2009 | Natanzon |
| 2009/0132916 A1 | 5/2009 | Filatov |
| 2009/0148010 A1 | 6/2009 | Boroczky |
| 2009/0171991 A1 | 7/2009 | Gitai |
| 2009/0177495 A1 | 7/2009 | Abousy |
| 2009/0187407 A1 | 7/2009 | Soble |
| 2009/0204009 A1 | 8/2009 | Powers |
| 2009/0222388 A1 | 9/2009 | Hua |
| 2009/0228299 A1 | 9/2009 | Kangarloo |
| 2009/0310836 A1 | 12/2009 | Krishnan |
| 2010/0010587 A1 | 1/2010 | Skelton |
| 2010/0088117 A1 | 4/2010 | Belden |
| 2010/0152577 A1 | 6/2010 | Young et al. |
| 2010/0177942 A1 | 7/2010 | Kolatt |
| 2010/0211409 A1 | 8/2010 | Kotula |
| 2010/0260399 A1 | 10/2010 | Hajnal |
| 2010/0278405 A1 | 11/2010 | Kakadiaris |
| 2010/0278427 A1 | 11/2010 | Li |
| 2011/0010192 A1 | 1/2011 | Backhaus |
| 2011/0075920 A1 | 3/2011 | Wu |
| 2011/0103675 A1 | 5/2011 | Marshall |
| 2011/0122241 A1 | 5/2011 | Wang |
| 2011/0137132 A1 | 6/2011 | Gustafson |
| 2011/0141118 A1 | 6/2011 | Cardno |
| 2011/0153351 A1 | 6/2011 | Vesper |
| 2011/0160543 A1 | 6/2011 | Parsey |
| 2011/0176712 A1 | 7/2011 | Hill |
| 2011/0188718 A1 | 8/2011 | Hill |
| 2011/0235910 A1 | 9/2011 | Soceanu |
| 2011/0263994 A1 | 10/2011 | Burns |
| 2011/0276343 A1 | 11/2011 | Lagor |
| 2011/0276346 A1 | 11/2011 | Reiner |
| 2011/0276348 A1 | 11/2011 | Ahn |
| 2012/0014559 A1 | 1/2012 | Suehling |
| 2012/0041937 A1 | 2/2012 | Dhillon |
| 2012/0130734 A1 | 5/2012 | White |
| 2012/0158432 A1 | 6/2012 | Jain |
| 2012/0166209 A1 | 6/2012 | Lacal |
| 2012/0172700 A1 | 7/2012 | Krishnan |
| 2012/0265551 A1 | 10/2012 | Backhaus |
| 2012/0269407 A1 | 10/2012 | Criminisi |
| 2012/0330876 A1 | 12/2012 | Bryce |
| 2013/0004044 A1 | 1/2013 | Ross |
| 2013/0018674 A1 | 1/2013 | Bedi |
| 2013/0116573 A1 | 5/2013 | Herman |
| 2013/0124527 A1 | 5/2013 | Lee |
| 2013/0173308 A1 | 7/2013 | Hough |
| 2013/0190637 A1 | 7/2013 | Zhang |
| 2013/0226616 A1 | 8/2013 | Nigam |
| 2013/0251233 A1 | 9/2013 | Yang |
| 2013/0321286 A1 | 12/2013 | Petruzzelli et al. |
| 2013/0338496 A1 | 12/2013 | Hielscher et al. |
| 2014/0058746 A1 | 2/2014 | Drucker |
| 2014/0058748 A1 | 2/2014 | Ford |
| 2014/0063011 A1 | 3/2014 | Noshi |
| 2014/0073904 A1 | 3/2014 | Biber |
| 2014/0177947 A1 | 6/2014 | Krizhevsky |
| 2014/0219500 A1 | 8/2014 | Moehrle |
| 2014/0222444 A1 | 8/2014 | Cerello |
| 2014/0292814 A1 | 10/2014 | Tsujimoto |
| 2014/0314311 A1 | 10/2014 | Garera |
| 2014/0316793 A1 | 10/2014 | Pruit |
| 2014/0328517 A1 | 11/2014 | Gluncic |
| 2014/0330855 A1 | 11/2014 | Atanasiu |
| 2014/0341471 A1 | 11/2014 | Ono et al. |
| 2014/0365239 A1 | 12/2014 | Sadeghi |
| 2015/0025909 A1 | 1/2015 | Hayter |
| 2015/0031979 A1 | 1/2015 | Rappaport et al. |
| 2015/0063667 A1 | 3/2015 | Sprencz |
| 2015/0066539 A1 | 3/2015 | Sheffer |
| 2015/0089337 A1 | 3/2015 | Grady |
| 2015/0089365 A1 | 3/2015 | Zhao |
| 2015/0112992 A1 | 4/2015 | Lee |
| 2015/0127370 A1 | 5/2015 | Cornelis |
| 2015/0230773 A1 | 8/2015 | Cho |
| 2015/0254843 A1 | 9/2015 | Brown |
| 2015/0269143 A1 | 9/2015 | Park |
| 2015/0278457 A1 | 10/2015 | De la Torre |
| 2015/0286802 A1 | 10/2015 | Kansara |
| 2015/0305706 A1 | 10/2015 | Kanik |
| 2015/0332111 A1 | 11/2015 | Kisilev |
| 2015/0347464 A1 | 12/2015 | Takata |
| 2015/0356260 A1 | 12/2015 | D'Souza |
| 2015/0356450 A1 | 12/2015 | Dursun |
| 2016/0019695 A1 | 1/2016 | Chukka |
| 2016/0027175 A1 | 1/2016 | Kim et al. |
| 2016/0048972 A1 | 2/2016 | Kam |
| 2016/0104281 A1 | 4/2016 | Grady |
| 2016/0140300 A1 | 5/2016 | Purdie |
| 2016/0148351 A1 | 5/2016 | Hilbert |
| 2016/0174902 A1 | 6/2016 | Georgescu |
| 2016/0203281 A1 | 7/2016 | Zalis |
| 2016/0239962 A1 | 8/2016 | Markin |
| 2016/0239969 A1 | 8/2016 | Davatzikos |
| 2016/0260211 A1 | 9/2016 | Gillies |
| 2016/0267221 A1 | 9/2016 | Larcom |
| 2016/0292856 A1 | 10/2016 | Niemeijer |
| 2016/0307319 A1 | 10/2016 | Miller et al. |
| 2016/0314588 A1 | 10/2016 | Harper |
| 2016/0335403 A1 | 11/2016 | Mabotuwana |
| 2016/0343127 A1 | 11/2016 | Miller |
| 2016/0350620 A1 | 12/2016 | Rao |
| 2016/0350914 A1 | 12/2016 | Champlin |
| 2016/0350919 A1 | 12/2016 | Steigauf |
| 2016/0364526 A1 | 12/2016 | Reicher |
| 2016/0364862 A1 | 12/2016 | Reicher |
| 2017/0004619 A1 | 1/2017 | Liang |
| 2017/0024517 A1 | 1/2017 | Biegert |
| 2017/0032084 A1 | 2/2017 | Stalling |
| 2017/0053074 A1 | 2/2017 | Enzmann |
| 2017/0053102 A1 | 2/2017 | Katz |
| 2017/0068780 A1 | 3/2017 | Dobrean |
| 2017/0076043 A1 | 3/2017 | Dormer |
| 2017/0109881 A1 | 4/2017 | Avendi |
| 2017/0116497 A1 | 4/2017 | Georgescu |
| 2017/0200268 A1 | 7/2017 | Podilchuk |
| 2017/0215840 A1 | 8/2017 | Gregg |
| 2017/0301092 A1 | 10/2017 | Kikuchi |
| 2017/0304732 A1 | 10/2017 | Velic |
| 2017/0308680 A1 | 10/2017 | Efros |
| 2017/0330320 A1 | 11/2017 | Lynch |
| 2017/0337329 A1 | 11/2017 | Liu |
| 2017/0337343 A1 | 11/2017 | Kakadiaris |
| 2017/0372007 A1 | 12/2017 | Lu |
| 2018/0012360 A1 | 1/2018 | Bredno |
| 2018/0025255 A1 | 1/2018 | Poole |
| 2018/0033144 A1 | 2/2018 | Risman |
| 2018/0046758 A1 | 2/2018 | Gogin |
| 2018/0046764 A1 | 2/2018 | Katwala |
| 2018/0060488 A1 | 3/2018 | Reicher |
| 2018/0060512 A1 | 3/2018 | Sorenson |
| 2018/0060535 A1 | 3/2018 | Reicher |
| 2018/0060691 A1 | 3/2018 | Bernal |
| 2018/0061049 A1 | 3/2018 | Robb |
| 2018/0101923 A1 | 4/2018 | Griesmann |
| 2018/0114595 A1 | 4/2018 | Stern |
| 2018/0116620 A1 | 5/2018 | Chen |

(56) References Cited

U.S. PATENT DOCUMENTS

| | | |
|---|---|---|
| 2018/0137244 A1 | 5/2018 | Sorenson |
| 2018/0150905 A1 | 5/2018 | Lee |
| 2018/0184931 A1 | 7/2018 | Chen |
| 2018/0189325 A1 | 7/2018 | Hohwald |
| 2018/0204111 A1 | 7/2018 | Zadeh |
| 2018/0214086 A1 | 8/2018 | Park |
| 2018/0239868 A1 | 8/2018 | Kopylov |
| 2018/0240140 A1 | 8/2018 | Whitley |
| 2018/0260950 A1 | 9/2018 | Samset |
| 2018/0268737 A1 | 9/2018 | Garnavi |
| 2018/0276248 A1 | 9/2018 | Burkett |
| 2018/0286037 A1 | 10/2018 | Zaharchuk |
| 2018/0315182 A1 | 11/2018 | Rapaka |
| 2018/0322632 A1 | 11/2018 | Barnes |
| 2018/0330193 A1 | 11/2018 | Ideka |
| 2018/0341747 A1 | 11/2018 | Bernard |
| 2018/0341753 A1 | 11/2018 | Lyman |
| 2018/0341833 A1 | 11/2018 | Bernard |
| 2018/0342055 A1 | 11/2018 | Lyman |
| 2018/0365281 A1 | 12/2018 | Patel |
| 2018/0373999 A1 | 12/2018 | Xu |
| 2019/0005195 A1 | 1/2019 | Peterson |
| 2019/0005200 A1 | 1/2019 | Zimmerman |
| 2019/0005684 A1 | 1/2019 | De Fauw |
| 2019/0006024 A1 | 1/2019 | Kapoor |
| 2019/0019300 A1 | 1/2019 | Simpson |
| 2019/0026278 A1 | 1/2019 | Abedin |
| 2019/0056496 A1 | 2/2019 | Sakai |
| 2019/0087544 A1 | 3/2019 | Peterson |
| 2019/0122360 A1 | 4/2019 | Zhang |
| 2019/0139647 A1 | 5/2019 | Wekel |
| 2019/0142519 A1 | 5/2019 | Siemionow |
| 2019/0147225 A1 | 5/2019 | Thodberg |
| 2019/0156477 A1 | 5/2019 | Perrin |
| 2019/0156921 A1 | 5/2019 | Kohli |
| 2019/0189264 A1 | 6/2019 | Stoval |
| 2019/0197358 A1 | 6/2019 | Madani |
| 2019/0209121 A1 | 7/2019 | Miyachi |
| 2019/0237198 A1 | 8/2019 | Grady |
| 2019/0279009 A1 | 9/2019 | Srirangam |
| 2019/0279761 A1 | 9/2019 | Bernard |
| 2019/0287686 A1 | 9/2019 | Takeda |
| 2019/0294961 A1 | 9/2019 | Zuev |
| 2019/0295440 A1 | 9/2019 | Hadad |
| 2019/0303677 A1 | 10/2019 | Choutas |
| 2019/0326007 A1 | 10/2019 | Sharma |
| 2019/0370969 A1 | 12/2019 | Katzmann |
| 2019/0378278 A1 | 12/2019 | Bose |
| 2019/0385056 A1 | 12/2019 | Girard |
| 2020/0019823 A1 | 1/2020 | Wang |
| 2020/0020097 A1 | 1/2020 | Do |
| 2020/0020133 A1 | 1/2020 | Najaf-Zadeh |
| 2020/0037962 A1 | 2/2020 | Shanbhag |
| 2020/0043599 A1 | 2/2020 | Yoon |
| 2020/0043600 A1 | 2/2020 | Glottmann |
| 2020/0082934 A1 | 3/2020 | Venkataraman |
| 2020/0085382 A1 | 3/2020 | Taerum |
| 2020/0089983 A1 | 3/2020 | Manickam |
| 2020/0097727 A1 | 3/2020 | Stumpe |
| 2020/0104646 A1 | 4/2020 | Eno |
| 2020/0118317 A1 | 4/2020 | Mysore Siddu |
| 2020/0143912 A1 | 5/2020 | Rosenberg |
| 2020/0160301 A1 | 5/2020 | Lyman |
| 2020/0160511 A1 | 5/2020 | Lyman |
| 2020/0160520 A1 | 5/2020 | Prosky |
| 2020/0160979 A1 | 5/2020 | Lyman |
| 2020/0161005 A1 | 5/2020 | Lyman |
| 2020/0167930 A1 | 5/2020 | Wang |
| 2020/0168304 A1 | 5/2020 | Manasco |
| 2020/0190585 A1 | 6/2020 | Wassmann |
| 2020/0210490 A1 | 7/2020 | Hutchins |
| 2020/0226462 A1 | 7/2020 | Maddison |
| 2020/0250794 A1 | 8/2020 | Zimmer |
| 2020/0265946 A1 | 8/2020 | Benjamin |
| 2020/0302168 A1 | 9/2020 | Vo |
| 2020/0320682 A1 | 10/2020 | Alexander |
| 2020/0334228 A1 | 10/2020 | Matyska |
| 2020/0342206 A1 | 10/2020 | Jobin |
| 2020/0352518 A1 | 11/2020 | Lyman |
| 2020/0364104 A1 | 11/2020 | Chan |
| 2020/0364501 A1 | 11/2020 | Herz |
| 2020/0364856 A1 | 11/2020 | Nicolase |
| 2020/0373003 A1 | 11/2020 | Lyman |
| 2020/0380675 A1 | 12/2020 | Golden |
| 2020/0381105 A1 | 12/2020 | Bernard |
| 2020/0387810 A1* | 12/2020 | Hodgson ................ G06N 20/00 |
| 2020/0395119 A1 | 12/2020 | Lyman |
| 2021/0057067 A1 | 2/2021 | Lyman |
| 2021/0074394 A1 | 3/2021 | Prosky |
| 2021/0082545 A1 | 3/2021 | Lyman |
| 2021/0082547 A1 | 3/2021 | Yao |
| 2021/0112377 A1 | 4/2021 | Zhang |
| 2021/0118533 A1 | 4/2021 | Lyman |
| 2021/0118534 A1 | 4/2021 | Lyman |
| 2021/0118552 A1 | 4/2021 | Bernard |
| 2021/0158936 A1 | 5/2021 | Rao |
| 2021/0181287 A1 | 6/2021 | Sommer |
| 2021/0183485 A1 | 6/2021 | Yao |
| 2021/0183498 A1 | 6/2021 | Kalafut |
| 2021/0202072 A1 | 7/2021 | Yi |
| 2021/0216822 A1 | 7/2021 | Paik |
| 2021/0224546 A1 | 7/2021 | Lu |
| 2021/0233633 A1 | 7/2021 | Lints |
| 2021/0295966 A1 | 9/2021 | Lyman |
| 2021/0335464 A1 | 10/2021 | Poblenz |
| 2021/0366106 A1 | 11/2021 | Yao |
| 2021/0398283 A1 | 12/2021 | Yao |
| 2021/0407634 A1 | 12/2021 | Lyman |
| 2022/0005187 A1 | 1/2022 | Lyman |
| 2022/0005561 A1 | 1/2022 | Lyman |
| 2022/0005565 A1 | 1/2022 | Lyman |
| 2022/0005566 A1 | 1/2022 | Lyman |
| 2022/0028530 A1 | 1/2022 | Lyman |
| 2022/0028551 A1* | 1/2022 | Jordan ................... G16H 50/20 |
| 2022/0037019 A1 | 2/2022 | Covington |
| 2022/0051114 A1 | 2/2022 | Lyman |
| 2022/0051768 A1 | 2/2022 | Lyman |
| 2022/0051771 A1 | 2/2022 | Lyman |
| 2022/0061746 A1 | 3/2022 | Lyman |
| 2022/0068444 A1 | 3/2022 | Prosky |
| 2022/0076793 A1 | 3/2022 | Lyman |
| 2022/0076810 A1 | 3/2022 | Lyman |
| 2022/0084642 A1 | 3/2022 | Lyman |

FOREIGN PATENT DOCUMENTS

| | | |
|---|---|---|
| CN | 111046951 | 4/2020 |
| EP | 1503359 A1 | 2/2005 |
| EP | 2457512 A1 | 5/2012 |
| EP | 3511941 A1 | 7/2019 |
| GB | 2457022 A | 8/2009 |
| KR | 1020100014065 A | 2/2010 |
| KR | 1020180040287 A | 4/2018 |
| WO | 2003003796 | 1/2003 |
| WO | 2005001742 | 1/2005 |
| WO | 2008093561 | 8/2007 |
| WO | 2010040075 A2 | 4/2010 |
| WO | 2015175799 A1 | 11/2015 |
| WO | 2016013004 | 1/2016 |
| WO | 2017201540 | 11/2017 |
| WO | 2018236497 A1 | 12/2018 |
| WO | 2019051359 A1 | 3/2019 |
| WO | 2020106631 A1 | 5/2020 |
| WO | 2020170533 A1 | 8/2020 |
| WO | 2021108100 A1 | 6/2021 |
| WO | 2022005934 A1 | 1/2022 |
| WO | 2022036351 A1 | 2/2022 |

OTHER PUBLICATIONS

Anwar, et al., "Medical Image Analysis using Convolutional Neural Networks: A Review", Journal of Medical Systems, Oct. 2018; 20 pgs.

(56) References Cited

OTHER PUBLICATIONS

Armato, et al.; Assessment of Radiologist Performance in the Detection of Lung Nodules: Dependence on the Definition of 'Truth', Academic Radiology, Jan. 2009; pp. 28-38; vol. 16, No. 1.

Attaluri, et al.; Efficient and Accurate Abnormality Mining from Radiology Reports with Customized False Positive Reduction; arXiv:1810.000967v1; Oct. 1, 2018; 15 pgs.

BraTS Multimodal Brain Tumor Segmentation Challenge; Pre-Conference Proceedings of the 7th MICCAI BraTS Challenge (2018); Sep. 16, 2018; 578 pgs; Granada, Spain.

Broglio; Randomization in Clinical Trials Permuted Blocks and Stratification; 2018 American Medical Association; JAMA Guide to Statistics and Methods; Jun. 5, 2018, pp. 2223-2224; vol. 319, No. 21.

Choi, et al.; Learning low-dimensional representations of medical concepts; AM IA Summits on Translational Science Proceedings, 2016, pp. 41-50.

Clunie et al.; Technical Challenges of Enterprise Imaging: HIMSS-SIIM Collaborative White Paper; J Digit Imaging, Aug. 30, 2016; pp. 583-614.

Gueld, et al.; Quality of DICOM header information for image categorization; Proceedings of the SPIE; May 16, 2002; pp. 280-287; vol. 4685.

Hofmanniger, et al.; Mapping Visual Features to Semantic Profiles for Retrieval in Medical Imaging; 2015 IEEE Conference on Computer Vision and Pattern Recognition (CVPR); Jun. 7-12, 2015; pp. 457-465.

International Searching Authority; International Search Report and Written Opinion; International Application No. PCT/US2018/032927; Sep. 14, 2018; 9 pgs.

International Searching Authority; International Search Report and Written Opinion; International Application No. PCT/US2020/059064; Feb. 26, 2021; 12 pgs.

International Searching Authority; International Search Report and Written Opinion; International Application No. PCT/US2021/039313; Oct. 21, 2021; 9 pgs.

International Searching Authority; International Search Report and Written Opinion; International Application No. PCT/US2021/071143; Dec. 3, 2021; 10 pgs.

Kalpathy-Cramer et al.; Automated Image Modality Based Classification and Annotation to Improve Medical Image Retrieval; 2007.

Ker, et al.; Deep Learning Applications in Medical Image Analysis; IEEE Access; 2018; pp. 9375-9389; vol. 6; 2018, doi: 10.1109/ACCESS.2017.2788044.

Kuzmak, et.al., Streamlining Importation of Outside Prior DICOM Studies Into An Imaging System, J. Digit. Imaging 25: 70-77; pp. 70-77.

Lai et al., Medical Image Classification Based on Deep Features Extracted by Deep Model and Statistic Feature Fusion with Multilayer Perceptron; Comput Intell Neurosci. 2018; Sep. 12, 2018; 41 pgs.

Lai, et al.; An adaptive window width/center adjustment system with online training capabilities for MR images. Artificial intelligence in medicine 33.1 (2005): pp. 89-101.

Long, et al.; Fully convolutional networks for semantic segmentation; Proceedings of the IEEE Conference on Computer Vision and Pattern Recognition; 2015; pp. 3431-3440.

Lorch et al.; Automated Detection of Motion Artefacts in MR Imaging Using decision Forests; Journal of Medical Engineering; vol. 2017, Art. ID 4501647; 2017; 9 pgs.

Minnaar, Alex; Deep Learning Basics: Neural Networks, Backpropagation and Stochastic Gradient Descent; http://alexminnaar.com/deep-learning-basics-neural-networks-backpropagation-and-stochastic-gradient-descent.html; Feb. 14, 2015; 11 pages.

Olah, Christopher; Calculus on Computational Graphs: Backpropagation; http://colah.github.io/posts/2015-08-Backprop/; Aug. 31, 2015; 7 pages.

Olatunji; Learning to estimate label uncertainty for automatic radiology report parsing; Oct. 1, 2019, 4 pages.

Pham, et al.; Natural language processing of radiology reports for the detection of thromboembolic diseases and clinically relevant incidental findings; BMC Bioinformatics; 15:266; 2014; 10 pgs [https://www.biomedcentral.com/1471-2105/15/266].

Pons, et al.; Natural Language Processing in Radiology: A Systematic Review; Radiology; vol. 279, No. 2; May 2016; pp. 329-343.

Reid, Stuart; 10 misconceptions about Neural Networks; http://www.turingfinance.com/misconceptions-about-neural-networks/; May 8, 2014; 24 pages.

Sandler, Ted S.; Regularlized Learning with Feature Networks; A Dissertation in Computer and Information Science; 2010; 99 pgs.

Torres, et al.; End-to-End Non-Small-Cell Lung Cancer Prognostication Using Deep Learning Applied to Pretreatment Computed Tomography; American Society of Clinical Oncology; JCO Clinical Cancer Informatics; 2021; pp. 1141-1150 [downloaded from ascopubs.org by 99.229.212.49 on Mar. 2, 2023 from 099.229.212.049].

VistA Imaging DICOM Gateway Importer User Manual; Department of Veteran Affairs; Jul. 2010; 88 pgs.

VistA Imaging System, VistA Imaging DICOM Gateway User Manual; Department of Veteran Affairs; Jun. 2013; Rev 14, MAG. 3.0 34, 116, 118; Jun. 2013; 254 pgs.

Wang, et al.; Chestx-ray8: Hospital-scale chest x-ray database and benchmarks on weakly-supervised classification and localization of common thorax diseases; Proceedings of the IEEE Conference on Computer Vision and Pattern Recognition. 2017; pp. 2097-2106.

Weydert, et al.; A preliminary Diagnosis Service Provides Prospective Blinded Dual-Review of All General Surgical Pathology Cases in an Academic Practice; Am J Surg Pathol; vol. 29, 2005; pp. 801-805.

What Not to Include in a Medical Record; Jun. 6, 2012; 3 pgs; [Retrieved from https://www.texmed.org/Template.aspx?id=1741].

Wikipedia: Backpropagation; https://en.wikipedia.org/wiki/Backpropagation#Assumptions_about_the_loss_function; downloaded from the internet on 18/15/18; 12 pages.

Wikipedia; Convolutional neural network; https://en.wikipedia.org/wiki/Convolutional_neural_network#Pooling_layer; downloaded from the internet on Jan. 15, 2018; 21 pages.

Yao, et al.; Weakly supervised medical diagnosis and localization from multiple resolutions; 2018; 17 pgs; arXiv preprint arXiv: 1803.07703.

Yao; et al., Analysis of focal loss with noisy labels; Dec. 2019.

Yoo Jae Chern; Remote medical-diagnosis system and method; 2010; 33 pgs (Translated by IP.com).

Zhang et al; "Personalized Pancreatic Tumor Growth Prediction via Group Learning"; arXiv:1706.00493v1 {cs.CV]; Jun. 1, 2017.

\* cited by examiner

300B

300F

300H

Outcome Variability: Case Study 2

| | Patient A | Patient B |
|---|---|---|
| Diagnosis | NSCLC | NSCLC |
| Stage (T / N / M) | IIIB (3 / 0 / 0) | IIIB (0 / 3 / 0) |
| Histology | AC | AC |
| Treatment | Chemo | Chemo |
| Age | 72 | 72 |
| Sex | Female | Male |
| BMI | 21.9 | 29.7 |
| Smoker | Yes | No |
| ECOG | 0 | 0 |
| Survival | 40 months | 13 months |
| IPRO Risk Prediction | Low (2/10) | High (10/10) |

Outcome Variability: Case Study 3

| | Patient A | Patient B |
|---|---|---|
| Diagnosis | NSCLC | NSCLC |
| Stage (T / N / M) | IIB (2 / X / X) | IIB (2 / 1 / X) |
| Histology | AC | AC |
| Treatment | Surgery | Surgery |
| Age | 67 | 67 |
| Sex | Male | Male |
| BMI | [missing] | [missing] |
| Smoker | Yes | Yes |
| ECOG | 0 | 0 |
| Survival | >71 months | 9 months |
| IPRO Risk Prediction | Low (4/10) | High (10/10) |

Patient A:

Patient B:

FIG. 3L

METHOD AND APPARATUS UTILIZING IMAGE-BASED MODELING IN HEALTHCARE

FIELD OF THE DISCLOSURE

The subject disclosure relates to a method and apparatus utilizing image-based modeling in healthcare.

BACKGROUND

Many conditions and diseases can be detected, classified and monitored through visual inspection of the particular body part, such as through use of imaging. The detection, classification and/or monitoring through use of radiologist interpretations of images can be used not only to facilitate treatment of the individual, but also to conduct and manage clinical trials for treatments.

Visual inspection, such as reading or interpreting an image, typically utilizes radiologists to manually annotate regions of interest, such as primary tumors. However, manual interpretation of an image including manual annotation is a time-consuming process, requires radiological expertise, is subject to inter-reader variability, and enforces the implication that only annotated regions of interest are correlated with outcomes.

BRIEF DESCRIPTION OF THE DRAWINGS

Reference will now be made to the accompanying drawings, which are not necessarily drawn to scale, and wherein:

FIGS. 3J-3L illustrate case studies comparing patients and their risk predictions generated in accordance with various aspects described herein.

FIGS. 3N-3R illustrate graphical user interfaces that can be generated by the modeling platform in accordance with various aspects described herein.

DETAILED DESCRIPTION

Figure 1:
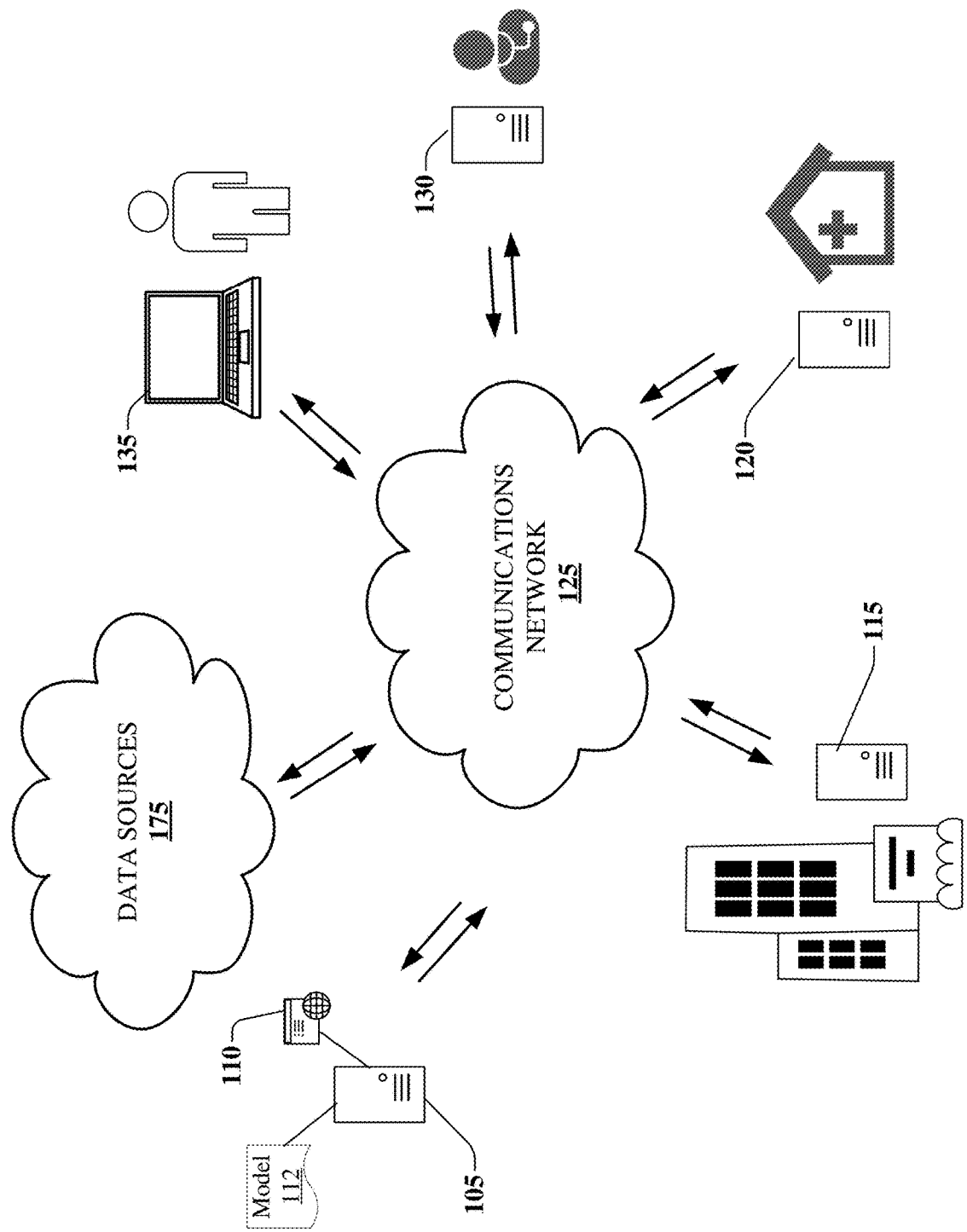
FIG. 1 is a block diagram illustrating an exemplary, non-limiting embodiment of a system in accordance with various aspects described herein.

The subject disclosure describes, among other things, illustrative embodiments for providing image-based modeling and a modeling platform to assist in clinical trials, healthcare treatment or other health-related events. Some of the embodiments described herein are directed towards analyzing a clinical trial(s) (e.g., not yet started, on-going, and/or completed), however, other embodiments are directed to analyzing patient treatment which may be occurring within a clinical trial or may be occurring outside of or otherwise not associated with any clinical trial (e.g., analysis of on-going treatment of a patient where the treatment was already approved). In one or more embodiments, the image-based modeling is applied only to images (which can include data representative of the images) for determining predicted variable(s) or is used with the images in conjunction with other medical/user data that is ingested by or otherwise analyzed by the model to facilitate the determining of the predicted variable(s). The predicted variable(s) alone or in conjunction with other information (including imputed variables that are determined from analysis of the images) can be used to generated event estimation information including time-to-event curves, survival curves, Kaplan Meier curves, and other outcome models. The predicted variables can include mortality risk scores. In one or more embodiments, the modeling platform can extract and utilize other data from the images (and/or can obtain the other data from other sources independent of the model's analysis of the images), which may or may not be a clinical variable (e.g., tumor size, cleanliness of margins, etc.), and which may not be a variable per se, but can be utilized for or otherwise facilitate some of the determinations (e.g., survival predictions). Some of the embodiments described herein are directed towards applying the image-based models to particular imaging modalities (e.g., computed tomography (CT) scans), however, other embodiments can apply the image-based models to other types of images or combinations of types (e.g., X-ray, Magnetic Resonance Imaging (MRI), etc.).

In one or more embodiments with respect to clinical trials (which can include various types of medical studies such as ones that utilize a control group and an investigational group), a cloud platform is provided so that automated patient eligibility determinations, screening and randomization can be derived by the image-based model from baseline images (e.g., pre-treatment images such as CT scans). In this cloud platform, ongoing treatment efficacy and prediction can be derived by the image-based model from follow-up images (e.g., CT scans during (i.e., on-treatment or in-treatment images) and after treatment), which can be reviewed by various entities such as the clinical operations manager. In this cloud platform, data submissions for the clinical trial(s) can be submitted to the FDA according to any requirements to obtain approval for the treatment of the clinical trial(s). The particular interaction with governmental regulatory bodies can be differ and can be accommodated by the exemplary systems and methodologies described herein including submissions of data from multiple clinical trials associated with a treatment which can then be evaluated by the agency (e.g., FDA) for approval. In one or more embodiments, the data generated or otherwise determined from the systems and methodologies described herein can be accessed (e.g., via the cloud platform) and/or utilized for various purposes including internal business decisions, regulatory authorities, or other purposes. In one or more embodiments, data can be generated or otherwise determined via the systems and methodologies described herein for various clinical endpoints which can include survival or survivability assessments, but which can also include other types of clinical endpoints.

In one or more embodiment, the modeling platform (based on predictions such as survival or survivability data or mortality time that are generated from the image-based model applied to baseline/pre-treatment images and/or follow-up images) allows for predicting success of a trial during the trial at different time periods, such as based on particular clinical endpoints. In another embodiment, the modeling platform (based on predictions such as survival data or mortality time that are generated from the image-based model applied to baseline/pre-treatment images and/or follow-up images) allows for measuring current treatment effect and/or predicting treatment effect during an on-going clinical trial. All of which is information that a clinical trial manager, pharmaceutical company or other entity involved in a clinical trial would desire to know and which is a practical application to operating or managing clinical trial(s). One or more of the embodiments described herein allow for generating event estimation curves according to predictive analysis of various images (e.g., pre-treatment, on-treatment and/or post treatment) which can be associated with various data or be of various types, including clinical endpoint estimation, time-to-event estimation, survival estimation, random forest, Kaplan Meier curves, and so forth. One or more of the embodiments described herein can generate the event estimation curves or data representations in a format (or of a selected type) that can be best suited for providing an analysis of the data and/or an analysis of the clinical trial.

In one or more embodiments, the modeling platform (e.g., based on predictions such as survival data or mortality time that are generated from the image-based model applied to baseline/pre-treatment images and/or follow-up images) can be used with, or in place of, radiologists manually interpreting or annotating regions of interest. The modeling platform improves efficiency, avoids use of limited resources such as radiological expertise, is not subject to inter-reader variability, and avoids the implication that only annotated regions of interest are correlated with outcomes. Further efficiency is added by the modeling platform, particularly through its cloud-based platform, since in typical clinical trials, the hospital often has to download the image onto a DVD and mail it to the organization managing the clinical trial, which is a time consuming and inefficient process.

In one or more embodiments, the trained image-based model(s) can be generalizable to a broader population based on the size of the training dataset (e.g., 5% of all lung cancer patients across a country such as Canada although other sizes of datasets from various places can be utilized), which will include patients having various sorts of conditions, diseases and other comorbidities.

In one or more embodiments, the image-based modeling can provide time to event predictions. For example, these predictions can be according to treatment (e.g., surgery vs chemotherapy vs different chemotherapy vs. radiation). As another example, these predictions can be done longitudinally (i.e., predicting at different time points to show improvement or deterioration). This can include imaging before, during and/or after treatments for each patient, looking at visual changes in images over times for prediction, and/or predicting whether a tumor will return. As another example, these predictions can be by comorbidity, such as taking into account competing risks (e.g., heart disease).

In one or more embodiments, the modeling platform can provide explainability. For example, information can be generated as to why the model made a particular prediction. As another example, the model can generate a predicted image representative of the predicted tumor size and/or predicted shape corresponding to various points in the future. In one or more embodiments, the image-based modeling allows for inputting image(s) of a body part (e.g., lung) and the model can generate outcome prediction and a new image showing what the tumor/organ/image is predicted to look like in 3 months, 6 months, 1 year, and so forth to show how the tumor is expected to grow or shrink supporting the model's outcome prediction. In one or more embodiments, the image-based modeling can provide information corresponding to predictions being made that are categorized by various criteria such as by organ, by clinical variable, and so forth.

In one or more embodiments, the image-based modeling can provide predictions for treatment planning. These predictions can be done in conjunction with patients that may or may not be enrolled in a clinical trial. For example, the model can predict from an image (e.g., pre-treatment CT scan) outcomes for specific treatments. The clinician would then choose treatment that offers optimal outcome. As another example, the model can predict from an image (e.g., pre-treatment CT scan) optimal radiation dose by anatomical region to also reduce toxicity risk (i.e., radiation-induced pneumonitis). In another example, image guided treatment can be facilitated such as via an overlay on the image which is fed to the model and the model quantifies the input. As another example, the model can predict from an image (e.g., pre-treatment CT scan) treatment toxicity by treatment type or plan so that the physician can select or plan optimal treatment. As another example, the model can predict from an image (e.g., pre-treatment CT scan) functional test results (e.g., cardiopulmonary function) to quantify fitness for specific treatments (e.g., surgery). For example, the model can predict lung capacity which is used for qualifying patients for surgery. In this example, the prediction from the pre-treatment image can be used to determine at what point in the future the patient may no longer be eligible for surgery. As another example, the model can predict from an image (e.g., pre-treatment CT scan) a quantification of quality of life for various treatment options. In this example, the prediction from the pre-treatment image can be used to assess quality of life at particular time periods in the future, which may be used in place of or in conjunction with test walks, surveys, or other quantification techniques.

In one or more embodiments, the modeling platform can obtain information from personal data sources (e.g., smartwatch, pedometer, HR monitor, and so forth) of the patient which can be utilized as part of the prediction analysis and/or can be provided as additional medical data along with the predicted variables to assist in treatment planning.

In one or more embodiments, the image-based modeling and modeling platform can be utilized to facilitate and improve clinical trials, such as through use of a digital twin that is generated from an image (e.g., a pre-treatment CT scan of a candidate that will be in the investigational arm) where the digital twin can be utilized in a control arm of the clinical trial. The digital twin can be imputed with various information based on predictions from the image-based model applied to the baseline/pre-treatment image, similar to the information that an actual candidate in the control trial arm would exhibit or be associated with (e.g., survival data). In one or more embodiments, the use of a digital twin can speed up clinical trials and make them more efficient by reducing the number of actual candidates required to be utilized in the control arm, such as populating the control arm with a digital twin(s) derived from a candidate(s) that is in the investigational arm. In one or more embodiments, the digital twin can speed up clinical trials and make them more efficient by improving randomization between the investigational arm and the control arm such that the control arm can be balanced by digital twin(s) derived from a candidate (s) that is in the investigational arm. In one or more embodiments, digital twins can be utilized that are simulated control outcomes for individual patients/candidates. For example, during a clinical trial or before treatment, a digital twin can be created from the data collected from a patient/candidate, which can be solely image-based data or can be other information utilized in conjunction with the image-based data. In this example, this baseline data can be fed into a generative AI-model (e.g., a three-dimensional convolutional neural network (3DCNN) or other image-based model) that has been pre-trained, such as on a database of longitudinal patient data (e.g., image data of the patient) from historical trials, observational studies, and/or treatments. The AI-model can predict the likely outcome for that patient/candidate if the patient/candidate was to receive the control while the actual patient/candidate goes on to receive the treatments (which can be active or control) and the outcome under that treatment is observed. In one or more embodiments, generative AI-models can be trained on historical data which can then be used to create digital twins that predict what would likely happen to a particular patient/candidate over the course of a trial if the patient/candidate was treated with the current standard of care (which may be in addition to a placebo).

As an example, the modeling platform can provide automated eligibility screening and/or matching to clinical trials based on a pre-treatment image (alone or in conjunction with other medical/user data for the candidate). As another example, the modeling platform can provide automated trial randomization (investigational arm vs control arm) to clinical trial(s) based on analysis of a pre-treatment image (alone or in conjunction with other medical/user data for the participant). As another example, the modeling platform can provide imaging-based prognostic enrichment for participants in the clinical trial. As another example, the modeling platform can provide imaging-based companion diagnostic to qualify patients for treatment. For example, past clinical trial data can be used to identify ideal patient type for clinical trial success. As another example, inclusion/exclusion criteria based on historical trials can be utilized. As is described herein, the functions of the systems and methodologies described herein including the application of the image-based modeling can have many practical uses which not only improve clinical trials but also allow for a better understanding of the outcome of a clinical trial such as predicting commercial value of a new drug, such as based on changes in predicted patient outcomes. In one or more embodiments, the image-based modeling and modeling platform can automate or otherwise provide information for commercial value and/or pricing of treatment/medications, such as based on cost of current treatments and in consideration of demonstrated benefit during clinical trial. In one or more embodiments, the image-based modeling and modeling platform can predict the cost of a clinical trial, such as based on predicted variables including time of treatment, time at which treatment difference (i.e., treatment effect) will be detectable, and so forth. As is described herein, the functions of the systems and methodologies described herein including the application of the image-based modeling can have other practical uses in the context of patient treatment which not only provides predictions as to treatment results but also allow for a better understanding of the outcome of the treatment and whether changes to the treatment plan could or should be made.

In one or more embodiments, the modeling platform provides tools to assist various entities including pharmaceutical companies, clinical trial managers, healthcare providers and/or patients. As an example, the modeling platform can automate collection of terms via common language, abbreviations, spelling errors, etc. As another example, the modeling platform can automate protected health information (PHI) aggregation creating uniform formats. As another example, the modeling platform can make it easier to interpret data in a more uniform way out of multiple datasets. In one or more embodiments, the modeling platform can automate evaluation of clinical trial design such as improved endpoints, broader patient population, and so forth. In one or more embodiments, the image-based modeling can automate identification of organs (or other body parts) from image and/or automate annotations to the data including points of interest. In one or more embodiments, the modeling platform can create a searchable tool based on the identified organs or other body parts. In one or more embodiments, the modeling platform can create or otherwise provide automatic QA tools to ensure imaging protocols are properly followed. In one or more embodiments, the modeling platform allows for a reverse image search, such as finding similar images (e.g., similar tumor size and/or shape, similar organ size and/or shape, and so forth) based on a submitted image.

In one or more embodiments, the modeling platform facilitates and/or guides preventative care, which may or may not be for a patient participating in a clinical trial. As an example, the modeling platform through use of the image-based modeling can ingest a whole-body scan (or scans of target areas/organs of the body) to identify long term health risks. In this example, various models can be trained and utilized for the analysis such as models particular to a single organ or body part, models particular to groups of organs or body parts, or whole-body scan models. As another example, the modeling platform can rank health care risk by organ(s) and/or by comorbidity risk(s). As another example, the modeling platform can interface with portable devices to auto-screen without the need for manual interpretation, such as for use in a breast cancer screening.

In one or more embodiments, image-based modeling and the modeling platform can be combined with or otherwise used in conjunction to pathology, genomic sequencing, proteomics, transcriptomics. For example, digitized pathology images can be processed and included in the modeling platform in conjunction with the patient's images (e.g., CT imaging). In another example, results of genomic sequencing can be provided as an input into the modeling platform.

In one or more embodiments, image-based modeling and the modeling platform can be used by consumers for predicting optimal financial portfolio construction, predicting optimal diet, predicting optimal workout, physical therapy exercises. In one or more embodiments, image-based modeling and the modeling platform can be used by consumers for ranking long-term care facilities based on residents' health deterioration compared to the expected outcome.

In one or more embodiments, image-based modeling and the modeling platform can be used in veterinary medicine to create organ-based risk assessment for pets along with an expected response to treatment; decrease pet insurance based on the animal's risk score and/or recommend pet food based on animal's risk score. Other embodiments are described in the subject disclosure.

One or more aspects of the subject disclosure include a method performed by one or more processors or processing systems. For example, the method can include obtaining, by a processing system, a baseline/pre-treatment image for each candidate of a group of candidates for a clinical trial resulting in a group of baseline/pre-treatment images, where the baseline/pre-treatment image captures at least an organ that is to be subject to treatment for a disease in the clinical trial, and where the group of baseline/pre-treatment images are captured prior to the treatment. The method can include analyzing, by the processing system, the group of baseline/pre-treatment images according to an imaging model that includes a machine learning model (e.g., a neural network such as a convolutional neural network (CNN), 3DCNN, recurrent neural network (RNN), long short term memory (LSTM), and other modeling networks including current or future models). The method can include predicting, by the processing system according to the analyzing of the group of baseline/pre-treatment images, one or more clinical variables for the group of baseline/pre-treatment images resulting in predicted variables. The method can include determining, by the processing system, a first subset of candidates of the group of candidates that are eligible for the clinical trial based on the predicted variables and based on study criteria of the clinical trial, where the study criteria include inclusion criteria and/or exclusion criteria. The method can include determining, by the processing system, a second subset of candidates of the group of candidates that are ineligible for the clinical trial based on the predicted variables and based on the study criteria of the clinical trial. In other embodiments, the method can include obtaining consent for participation in the clinical trial according to the various laws, rules and/or regulations that are applicable to that jurisdiction which in some instances can include generating notices and obtaining consent to participate in the clinical trial(s).

One or more aspects of the subject disclosure include a device having a processing system including a processor; and having a memory that stores executable instructions that, when executed by the processing system, facilitate performance of operations. The operations can include obtaining a group of baseline/pre-treatment images for a group of candidates for a clinical trial, where the group of baseline/pre-treatment images capture at least an organ that is to be subject to treatment for a disease in the clinical trial, and where the group of baseline/pre-treatment images are captured prior to the treatment. The operations can include analyzing the group of baseline/pre-treatment images according to an imaging model that includes a machine learning model. The operations can include predicting, according to the analyzing of the group of baseline/pre-treatment images, one or more clinical variables for the group of baseline/pre-treatment images resulting in predicted variables. The operations can include generating, based on the predicted variables, digital twins for the group of candidates. The operations can include generating a graphical user interface and providing equipment of an entity managing the clinical trial with access to the graphical user interface. The operations can include obtaining images for the group of candidates participating in the clinical trial resulting in a group of on-treatment images, where the group of on-treatment images are associated with a time period of the treatment. The operations can include analyzing the group of on-treatment images according to the imaging model. The operations can include predicting, based on the analyzing of the group of on-treatment images, the one or more clinical variables for the group of on-treatment images resulting in predicted on-treatment variables. The operations can include generating event estimation curves (e.g., survival curves such as Kaplan Meier (KM) curves) based on the predicted on-treatment variables for an investigational trial arm and a control trial arm of the clinical trial, where the investigational arm includes the group of candidates and the control arm includes the digital twins. The operations can include presenting the event estimation curves in the graphical user interface.

One or more aspects of the subject disclosure include a non-transitory machine-readable medium, including executable instructions that, when executed by a processing system(s) including a processor(s), facilitate performance of operations. The operations can include obtaining a group of baseline/pre-treatment images for a group of candidates for a clinical trial, the group of baseline/pre-treatment images capturing at least an organ that is to be subject to treatment for a disease in the clinical trial, where the group of baseline/pre-treatment images are captured prior to the treatment. The operations can include analyzing the group of baseline/pre-treatment images according to an imaging model that includes a machine learning model. The operations can include predicting, according to the analyzing of the group of baseline/pre-treatment images, one or more clinical variables for the group of baseline/pre-treatment images resulting in predicted variables. The operations can include randomizing, based at least on the predicted variables, each candidate of the group of candidates to one of an investigational trial arm or a trial control arm of the clinical trial. The operations can include generating a graphical user interface and providing equipment of an entity managing the clinical trial with access to the graphical user interface. The operations can include obtaining images for the group of candidates participating in the clinical trial resulting in a group of on-treatment images, where the group of on-treatment images are associated with a time period of the treatment. The operations can include analyzing the group of on-treatment images according to the imaging model. The operations can include predicting, based on the analyzing of the group of on-treatment images, the one or more clinical variables for the group of on-treatment images resulting in predicted on-treatment variables. The operations can include generating event estimation curves (e.g., KM curves) based on the predicted on-treatment variables for the investigational trial arm and the control trial arm of the clinical trial. The operations can include presenting the event estimation curves in the graphical user interface.

Referring now to FIG. 1, a block diagram is shown illustrating an example, non-limiting embodiment of a system 100 in accordance with various aspects described herein. For example, system 100 can facilitate in whole or in part providing image-based modeling to assist in clinical trials, healthcare treatment or other health-related events. As an example, the image-based modeling can be performed based solely on analysis of an image(s) according to a trained image model or can be performed in conjunction with consideration, incorporation and/or analysis of other information, such as medical/user data for the individual (e.g., one or more of age, sex, weight, Eastern Cooperative Oncology Group (ECOG) status, smoking status, competing mortality risk, cardiac and pulmonary toxicity, TNM (Tumor, Nodes and Metastases) stage, pulmonary function, or other characteristics associated with the individual) or other clinical factors depending on the disease. In one or more embodiments, the other information that can be utilized as part of the image-based modeling via one or more imputed variable(s) (such as one or more described above) can be derived, generated or otherwise determined based solely on an analysis of the image (e.g., baseline/pre-treatment image) or can be derived, generated or otherwise determined based on other information (e.g., user input information, corresponding data collected for the potential candidates, etc.) and which can be in conjunction with the analysis of the image. In one or more embodiments, the images can be 2D and/or 3D images, such as CT scans and the image-based modeling can be according to 2D and/or 3D modeling. In one or more embodiments, system 100 can apply the image-based modeling to various organs (e.g., lungs, brain, liver, pancreas, colon, and so forth) alone or in combination, or to various regions of the body, including regions that have a tumor. In one or more embodiments, system 100 can apply the image-based modeling to volumes surrounding and including various organs, such as the thorax which includes the lungs. In one or more embodiments, system 100 can apply the image-based modeling to humans or animals. In one or more embodiments, system 100 can apply the image-based modeling for generating predicted variables for patients who are or are not part of a clinical trial.

In one or more embodiments, system 100 includes one or more servers or computing devices 105 (only one of which is shown) which can manage or otherwise provide image-based modeling to equipment of various entities to assist in clinical trials, healthcare treatment and/or other health-related events. As an example, the server 105 can communicate over a communications network 125 with equipment of a pharmaceutical entity (ies) or other entity (ies) managing a clinical trial(s), such as a computing device or server 115 (only one of which is shown). The server 105 can communicate over the communications network 125 with equipment of a hospital(s) or other healthcare treatment facility (ies) which may have a patient(s) that is, was or will be taking part in a clinical trial(s), such as a computing device or server 120 (only one of which is shown). The server 105 can communicate over the communications network 125 with equipment of a healthcare provider(s) such as a physician that may have a patient(s) who is, was, or will be taking part in the clinical trial(s), such as a computing device or server 130 (only one of which is shown). The server 105 can communicate over the communications network 125 with equipment of a patient(s) who is, was, or will be taking part in the clinical trial(s), such as a computing device or server 135 (only one of which is shown). Any number of devices or servers 105, 115, 120, 130, 135 can be utilized at any number of locations for facilitating image-based modeling that assists in clinical trials, healthcare treatment and/or other health-related events.

In one or more embodiments, server 105 can provide a modeling platform 110 accessible (in whole or in part) to devices or servers 115, 120, 130, 135. In one or more embodiments, the modeling platform 110 can provide one, some or all of the functions described herein, including image-based modeling which facilitates clinical trials, healthcare treatment and/or other health-related events. It should be understood by one of ordinary skill in the art that the modeling platform 110 can operate in various architectures including centralized or distributed environments, browser-based, installed software, and so forth. As an example, server 115 of the pharmaceutical entity or the other entity managing a clinical trial and server 120 of the hospital(s) or the other healthcare treatment facility may utilize installed software, while server 130 of the healthcare provider(s) and device 135 of the patient(s) utilize a browser-based access to the modeling platform 110.

In one or more embodiments, modeling platform 110 applies a trained image-based model to baseline (e.g., prior to treatment), on-treatment and/or post-treatment images (e.g., CT scans) to predict one or more clinical variables, such as mortality risk score, age, sex, weight, ECOG status, smoking status, competing mortality risk, cardiac and pulmonary toxicity, TNM stage, pulmonary function, or a combination thereof. In one or more embodiments, modeling platform 110 can selectively obtain, train and/or apply one of multiple trained image-based models, only one of which is shown (model 112), to one or more clinical trials, treatments, and so forth. In one or more embodiments, the modeling platform 110 can selectively apply the trained image-based model to each of the images (e.g., baseline/pre-treatment, on-treatment and post-treatment images), for instance as they are obtained or acquired, to predict the one or more clinical variables and to show changes in the predictions over time (i.e., different time periods of each of the images). In one or more embodiments, the baseline images (e.g., pre-treatment images) can be captured before and/or after a candidate(s) is accepted to the clinical trial, such as analyzing a first baseline/pre-treatment image as part of evaluating whether the candidate should participate in the clinical trial and analyzing a second baseline/pre-treatment image (captured later after being accepted to the clinical trial but before treatment commences such as according to a time limit for capturing imaging) as part of generating predicted variables and/or generating event estimation curves such as survival curves.

As an example, an image-based model 112 (e.g., a deep learning model such as a 3DCNN) can be trained based on images associated with a particular organ and/or a particular disease (e.g., which may be pre-treatment images where the treatment was the standard of care at the time), as well as survival data for the individuals associated with the images. The image-based model 112 can be, or can be derived from, various types of machine-learning systems and algorithms. The dataset (e.g., pre-treatment CT scans of individuals that underwent standard of care treatment and/or for whom survival or other data is available) for training the image-based model 112 can be from one or more of various data sources 175 which can be private and/or public data in various formats and which may or may not be anonymized data). In one or more embodiments, the training of the model can be performed based on historical relevant data (e.g., images where outcomes of treatment are known) from individuals that are different from the clinical trial candidates (e.g., where outcomes of treatment have not yet occurred and are unknown). In one embodiment, 80% of the historical relevant data can be utilized to train the model while 20% of the historical relevant data is utilized to validate the model. Other percentages for training and validation distribution can also be utilized. The model training can be done utilizing only images (e.g., from a private and/or public source) and survival data, or can be done in conjunction with other medical/user data (e.g., one or more of age, sex, weight, ECOG status, smoking status, co-morbidities, cardiac and pulmonary toxicity, TNM stage, pulmonary function, and so forth) for each of the individuals. Various modeling techniques can be applied for validation and/or improvement of the model, such as generating class activation maps as a visual explanation to indicate upon which anatomical regions the image-based model placed attention to generate its clinical variables (e.g., a mortality risk prediction). In one embodiment, the model 112 is not expressly or directly trained to focus on tumors.

In one embodiment, the modeling platform 110 can obtain a baseline/pre-treatment image(s) (e.g., CT scan) for each candidate of a group of candidates for a clinical trial resulting in a group of baseline/pre-treatment images. The baseline/pre-treatment images can capture an organ (which may also include capturing a surrounding area around the organ) that is to be subject to future treatment for a disease in the clinical trial. The group of baseline/pre-treatment images are captured prior to the treatment and can be provided to the modeling platform 110 from various equipment such as servers 120, 130. The modeling platform 110 can analyze the group of baseline/pre-treatment images according to the image-based model 112 which in this example is a 3DCNN trained model. According to the analysis of the group of baseline/pre-treatment images (which in one embodiment can be limited to only the images and not other medical/user data), the modeling platform 110 can predict one or more clinical variables (i.e., predicted variables) for the group of baseline/pre-treatment images. As an example, the predicted variables can include (or in one embodiment be limited to) a mortality risk score or other survival valuation for each candidate corresponding to each of the baseline/pre-treatment images. The baseline/pre-treatment images can also be obtained and analyzed for candidates who are to be part of the control trial arm (e.g., receive the standard of care treatment) to generate predicted variables for the control trial arm.

In one embodiment, the modeling platform 110 can assess eligibility for the clinical trial based on the predicted variables. In one embodiment, the modeling platform 110 can determine or otherwise identify a first subset of the candidates that are eligible for the clinical trial based on the predicted variables and based on study criteria of the clinical trial, such as inclusion criteria and exclusion criteria defined by the manager of the clinical trial. In one embodiment, the modeling platform 110 can determine a second subset of the candidates that are ineligible for the clinical trial based on the predicted variables and based on the study criteria of the clinical trial. For instance, the clinical trial manager can access the modeling platform 110 via the server 115 to view a graphical user interface (e.g., a Trial View) in order see the eligibility determinations that have been made as well as other information indicating the status of the clinical trial, such as subjects screened, screen failures, subject enrolled, which may be broken down by various criteria such as site names, investigators, and so forth (See FIG. 3E).

Various techniques can be utilized to determine which of the candidates will be participating in the clinical trial from those that have been selected as eligible by the modeling platform, where those techniques may or may not be implemented by the modeling platform 110. As an example, although other techniques can be implemented, the modeling platform 110 can generate notices for the first subset of candidates regarding eligibility, such as communications that can be sent to the second subset of candidates via their devices 135 (or otherwise sent to them) and/or communications that can be sent to healthcare providers of the second subset of candidates via their devices 130 (or otherwise sent to them). In one embodiment, the modeling platform 110 can obtain consent for the second subset of candidates to participate in the clinical trial according to the particular requirements of the jurisdiction.

In one embodiment, modeling platform 110 generates survival estimation curves such as Kaplan Meier curves based on the predicted variables for an investigational trial arm and a control trial arm of the clinical trial. In one embodiment, the modeling platform 110 can determine or detect an improper or erroneous randomization of the clinical trial (e.g., the control arm predictions such as survival are better than the investigational arm predictions). In this example, the investigational arm data can be calibrated or adjusted such as based on a difference in the KM curves between the investigational trial arm and the control trial arm (e.g., at baseline). Continuing with this example, the calibrating can occur after the treatment begins or after the treatment has finished.

In one embodiment, as follow-up images are captured or obtained for the candidates after treatment commences, the model 112 can be applied to the follow-up images to generate on-treatment predicted variables and the KM curves can be updated according to the updated data. In one embodiment, the generating of the on-treatment predicted variables and updating of the data can be performed for both the investigational arm and the control arm. In one embodiment, the process of capturing follow-up images, generating on-treatment predicted variables according to the model 112 being applied to the follow-up images, and updating of the data for the KM curves can be repeated, such as throughout the length of treatment.

In one embodiment, a graphical user interface of the modeling platform 110 can provide an option for selecting different time periods of the treatment and presenting particular KM curves for the investigational arm and/or the control arm corresponding to the selection (see FIGS. 3N-3Q).

In one or more embodiments, the modeling platform 110 provides information that allows a clinical manager or other entity to determine whether to make an adjustment to the clinical trial according to the predicted variables (e.g., baseline/pre-treatment and/or on-treatment) which can include, but is not limited to, one of: continuing the clinical trial, terminating the clinical trial or accelerating the clinical trial.

Figure 3A:
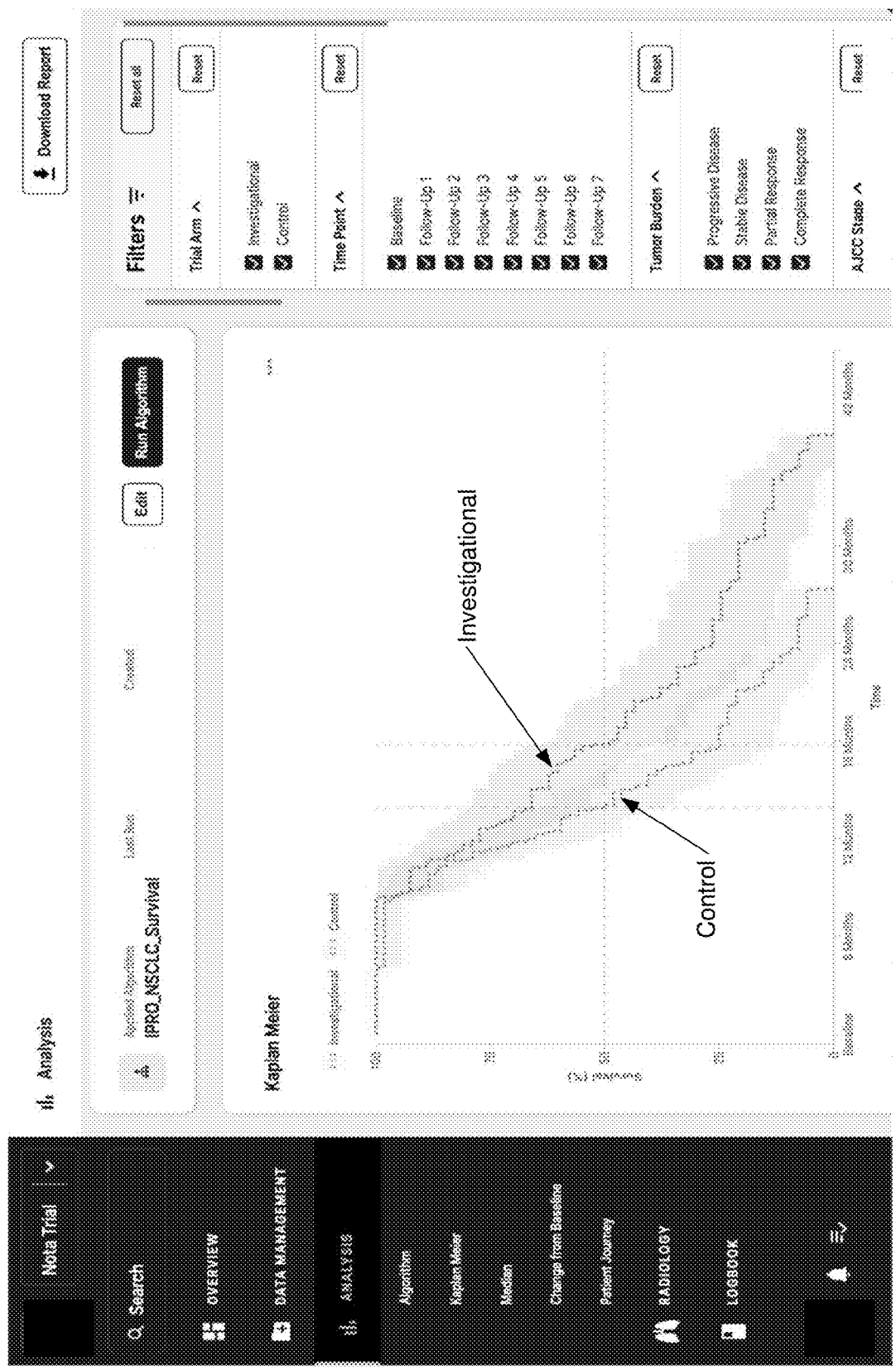
FIGS. 3A-3I illustrate graphical user interfaces that can be generated by the modeling platform in accordance with various aspects described herein.
Figure 3B:
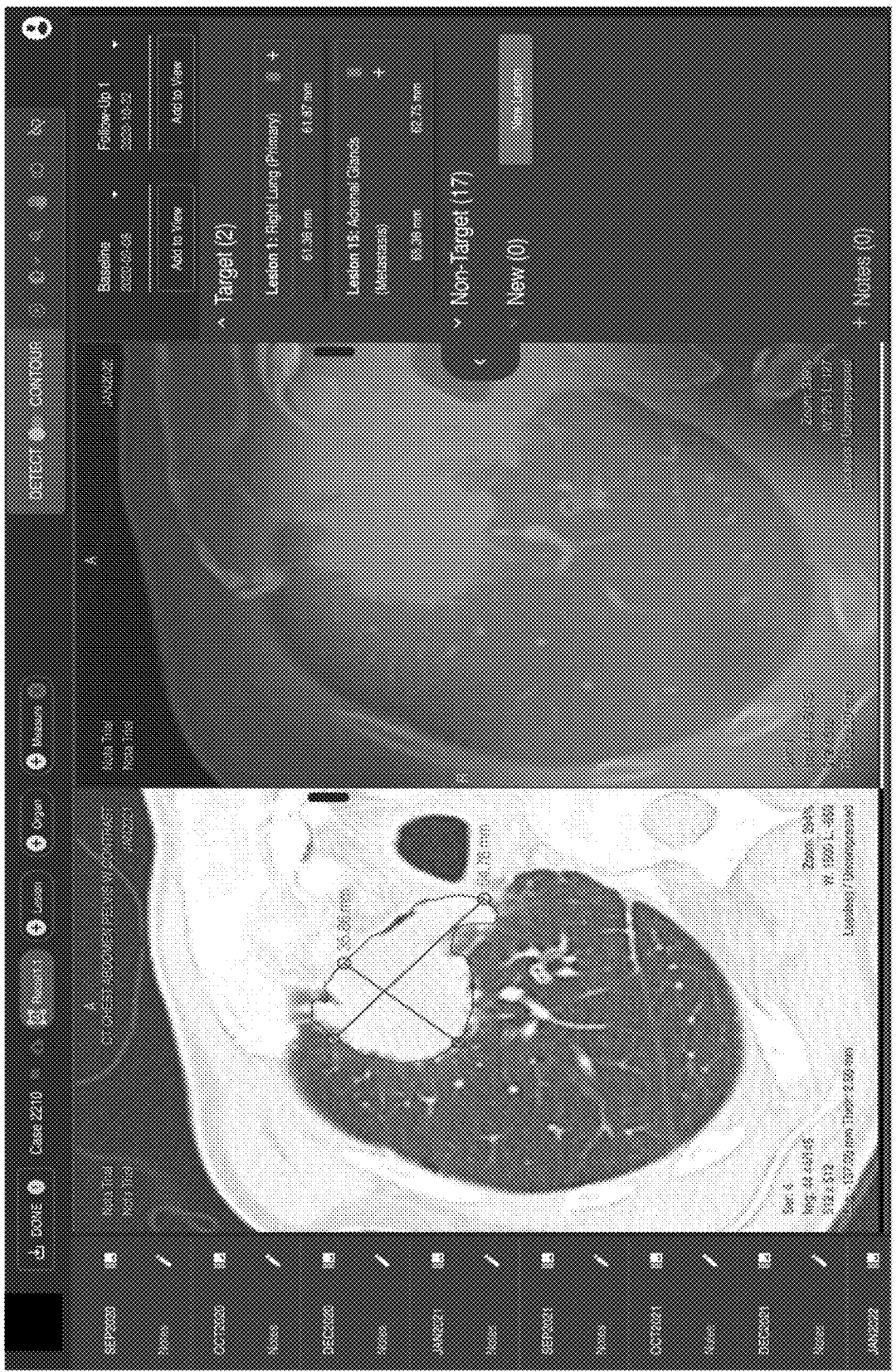
Figure 3C:
Figure 3D:
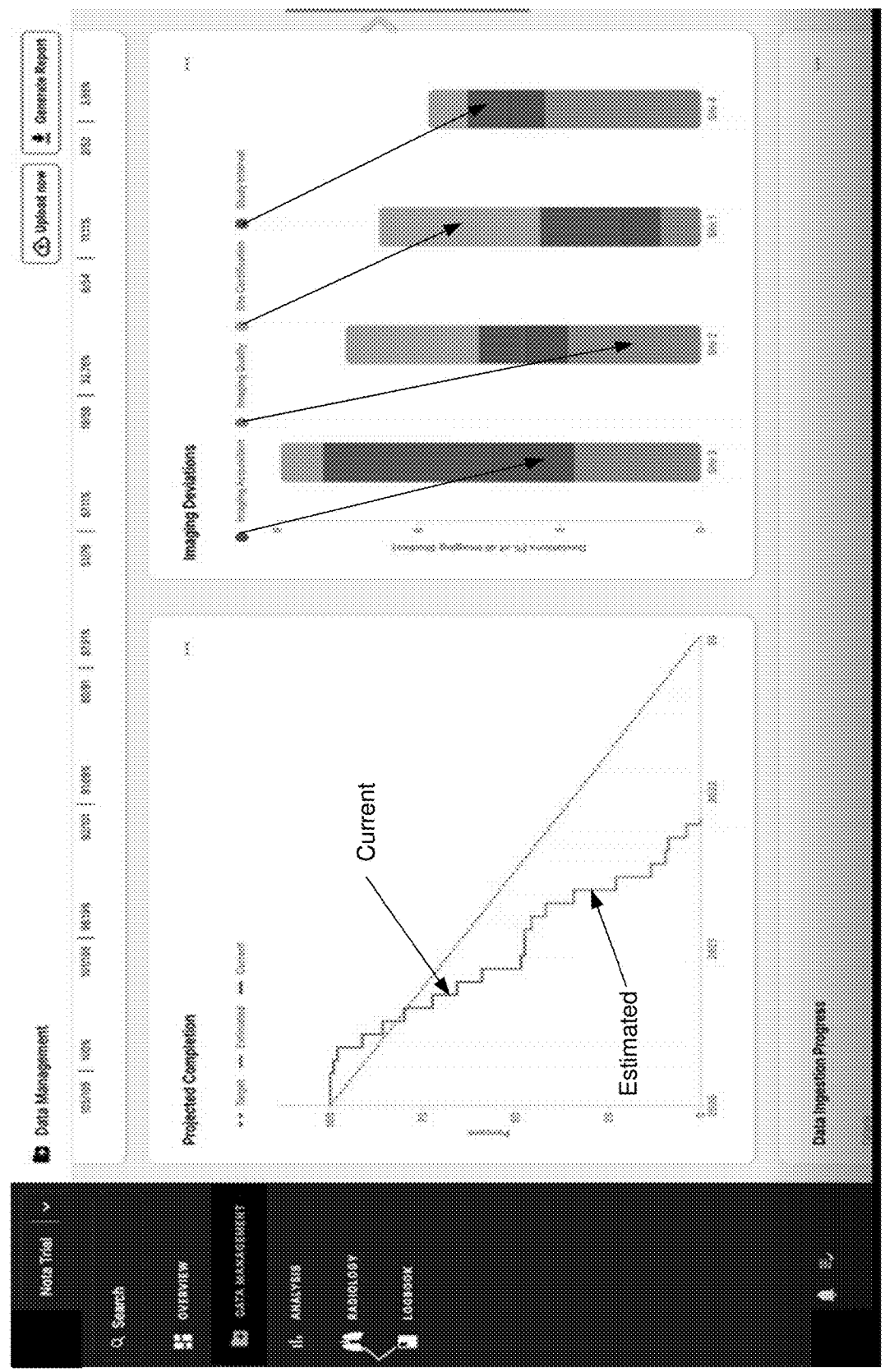
Figure 3E:
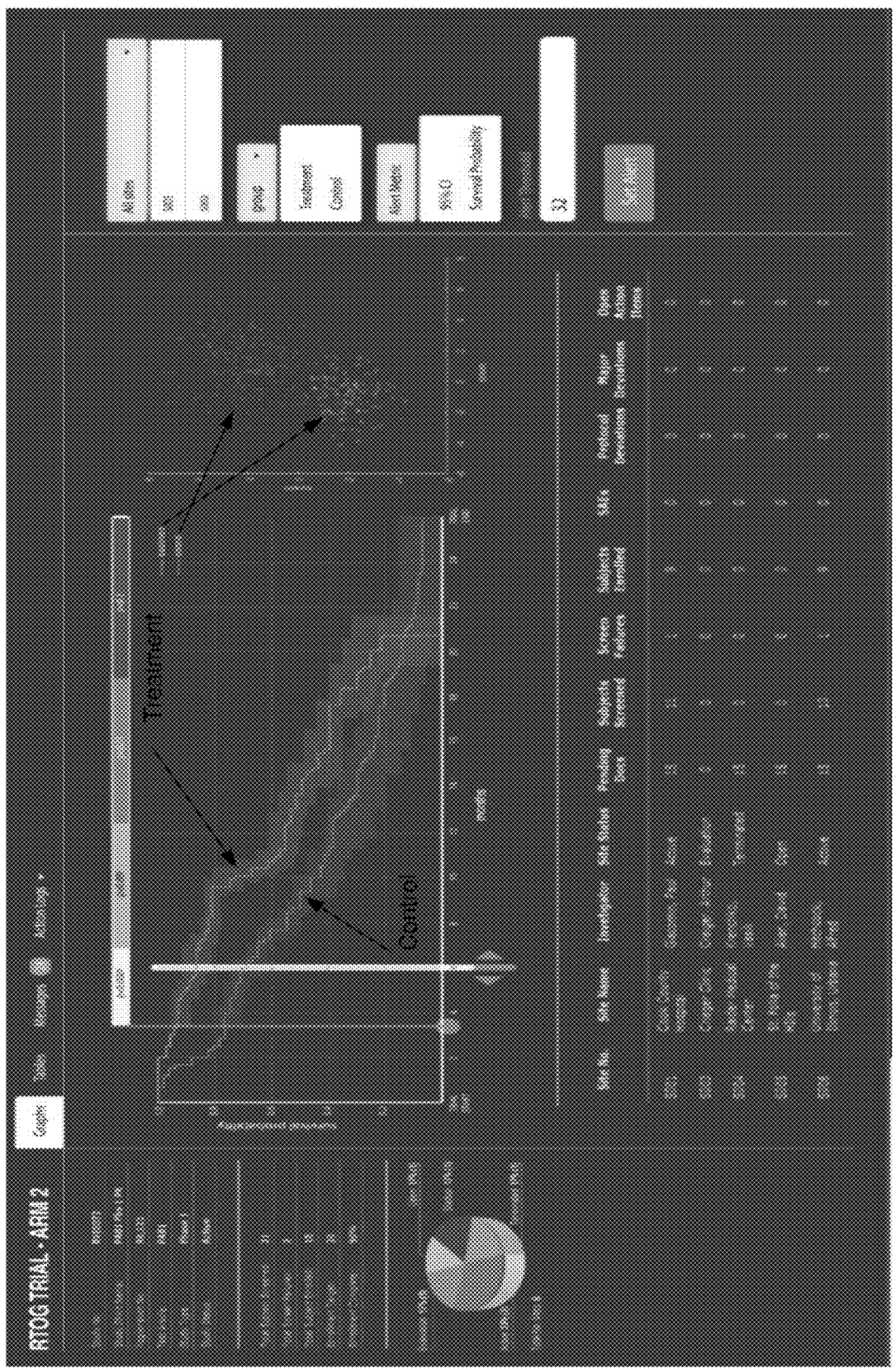
Figure 3F:
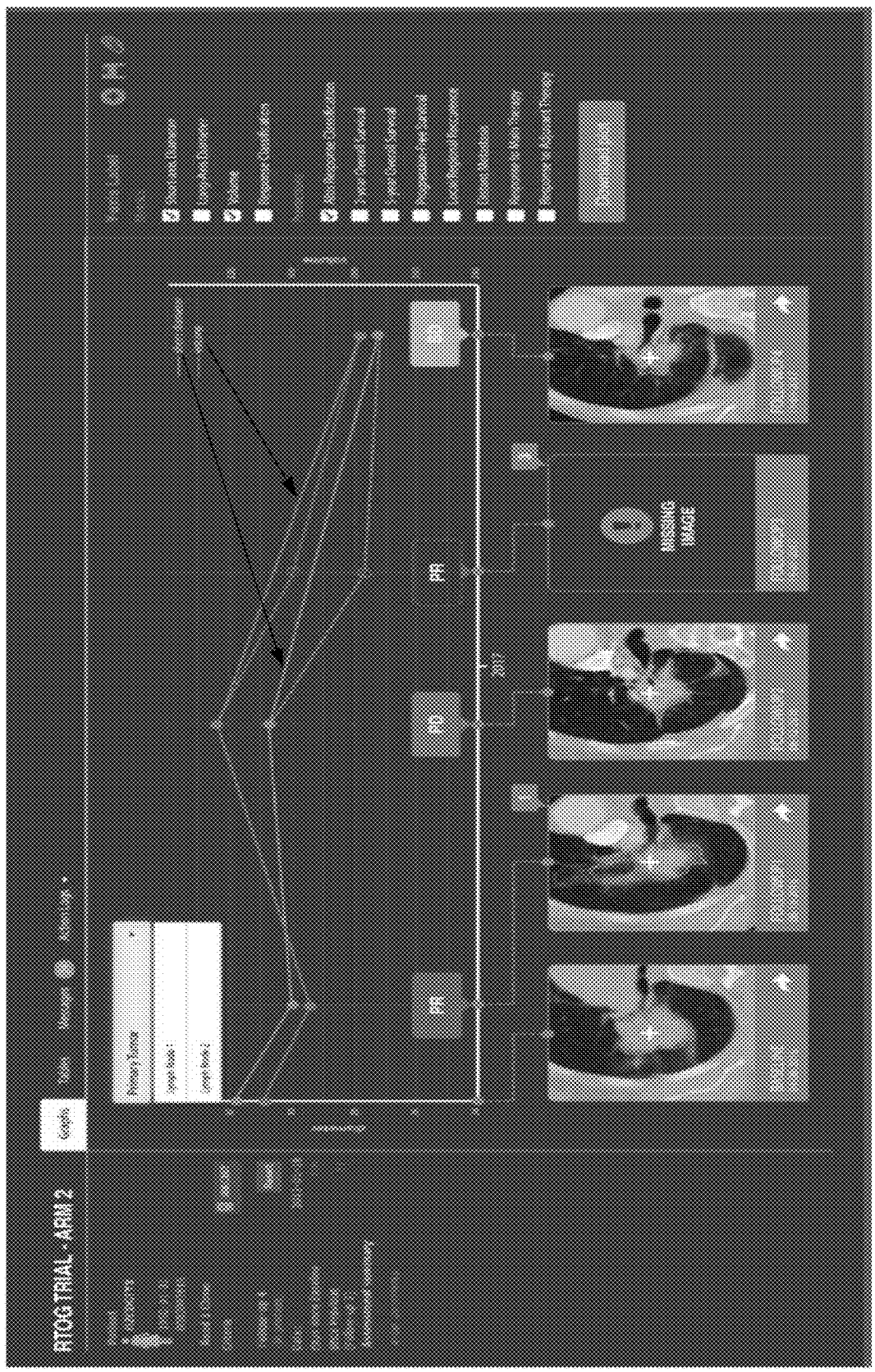

In one embodiment, a graphical user interface of the modeling platform 110 can be accessed by one or more of the devices 120, 130, 135 to view a patient portion of the graphical user interface that is related to a particular candidate without providing access to a remainder of the graphical user interface (e.g., data of other candidates) (see FIG. 3F). In one embodiment, the patient portion of the graphical user interface can include a predicted image(s) of the organ or body part at a future time(s) that is generated based on the image-modeling of the baseline/pre-treatment and/or on-treatment images, and/or based on the predicted variables and/or the predicted on-treatment variables. As an example, the predicted image(s) of the organ or body part at the future time(s) can be generated based on predicted tumor size, predicted tumor shape, predicted growth pattern, and/or predicted tumor location (which can be generated based on the image-modeling of the baseline/pre-treatment and/or on-treatment images). In one embodiment, the patient portion including the predicted image(s) of the organ or body part at the future time(s) for all of the candidates can be viewed in a Trial View by the pharmaceutical company and/or clinical manager. In one or more embodiments, the patient portion of the graphical user interface of the modeling platform 110 can be used to facilitate treatment and treatment decisions for the particular patient as described herein. In one embodiment, the graphical user interface of the modeling platform 110 allows a viewer to toggle on or off the image predictions for any follow up images such that if toggled on then the KM curve will include those images in the predictions.

Modeling platform 110 allows for imaging data acquisition from various sources, including trial sites, private and/or public data repositories, and so forth, which can accelerate clinical trial operations, and can increase their transparency. Modeling platform 110 can generate clinically meaningful predictions from each imaging study, which can be utilized alone or can complement traditional imaging interpretation frameworks. Modeling platform 110 can assist clinical trial sponsors in optimizing or improving internal decision making and allow for treatments to be brought to market sooner at a lower cost.

Modeling platform 110 can facilitate and enhance data management associated with a clinical trial. In one or more embodiments, modeling platform 110 provides automated imaging de-identification and quality control to be implemented for acquired baseline/pre-treatment, on-treatment and/or post-treatment images. In one or more embodiments, modeling platform 110 provides centralized cloud and/or on-premises storage of data. In one or more embodiments, modeling platform 110 provides a secure and access-controlled environment, such as based on entity-based permissions (e.g., clinical manager having full access while patients and physicians have limited access pertaining to their own treatment).

Modeling platform 110 can facilitate and enhance collaboration associated with a clinical trial. In one or more embodiments, modeling platform 110 can communicate image, patient, and/or cohort specific findings to a particular team (or other authorized groups of recipients). In one or more embodiments, modeling platform 110 can conduct research anytime, anywhere over the Internet or web. In one or more embodiments, modeling platform 110 can upload, download and/or transfer data associated with the clinical trial or entities, including patients.

Modeling platform 110 can facilitate and enhance analysis associated with the clinical trial and/or treatment of patients. In one or more embodiments, modeling platform 110 can streamline customizable imaging workflows using a Platform Viewer. In one or more embodiments, modeling platform 110 can increase reproducibility of imaging interpretation. In one or more embodiments, modeling platform 110 can generate (e.g., with or without user input or user assistance) annotations for ML research and biomarker discovery. In other embodiments, the modeling platform 110 can allow for editing annotations after their generation.

Modeling platform 110 can facilitate and enhance obtaining or otherwise determining insights associated with the clinical trial and/or treatment of patients. In one or more embodiments, modeling platform 110 can enhance trial design, patient stratification, and/or covariate analyses. In one or more embodiments, modeling platform 110 can facilitate patient enrichment strategies, such as adjustments or supplements to treatment. In one or more embodiments, modeling platform 110 can improve biomarker surrogacy.

Communications network 125 can provide various services including broadband access, wireless access, voice access and/or media access utilizing a plurality of network elements which can also facilitate the distribution of data (e.g., images, medical/user data, and so forth) from data sources 175, which may be any number of data sources that can be private and/or public sources. The communications network 125 can include a circuit switched or packet switched network, a voice over Internet protocol (VOIP) network, Internet protocol (IP) network, a cable network, a passive or active optical network, a 4G, 5G, or higher generation wireless access network, WIMAX network, UltraWideband network, personal area network or other wireless access network, a broadcast satellite network and/or other communications network. The computing devices or servers 105, 115, 120, 130, 135 can be various devices including personal computers, laptop computers, netbook computers, tablets, mobile phones, e-readers, phablets, or other computing devices and can communicate via various devices such as digital subscriber line (DSL) modems, data over coax service interface specification (DOCSIS) modems or other cable modems, a wireless modem such as a 4G, 5G, or higher generation modem, an optical modem and/or other access devices. Communications network 125 can include wired, optical and/or wireless links and the network elements can include service switching points, signal transfer points, service control points, network gateways, media distribution hubs, servers, firewalls, routers, edge devices, switches and other network nodes for routing and controlling communications traffic over wired, optical and wireless links as part of the Internet and other public networks as well as one or more private networks, for managing subscriber access, for billing and network management and for supporting other network functions.

In one or more embodiments, system 100 can provide an end-to-end imaging research stack to accelerate clinical trials, which can include patient eligibility screening, randomization of participating candidates, efficacy predictions and/or FDA submissions. In one or more embodiments, the modeling platform 110 can analyze other related organs as part of the image-based modeling (which is trained accordingly) and prediction process, such as the liver where the disease is lung cancer. In another embodiment, multiple organs (as a single image or multiple images) can be fed into the appropriately trained model to generate the predicted variables. In one or more embodiments, the modeling platform 110 can be applied to (and the image-based models trained for) various diseases such as cardiovascular disease. In one or more embodiments, model 112 can be trained as a new version of the algorithm on individual treatment types then utilized to predict a patient's response to multiple treatment types. For example, this could be used to inform a doctor's decision on how to treat a patient.

In one or more embodiments, model 112 can be trained utilizing pre-, in- and/or post-treatment images (e.g., where the treatment was the standard of care or another treatment). In one embodiment, the training images can include images from disease-free individuals. In one or more embodiments, treatment information such as lab reports, type of treatment, and so forth may or may not be incorporated into the longitudinal model to adjust for changes visible or detectable in the follow-up images.

In one or more embodiments, model 112 can be adjusted, revised or otherwise fine-tuned to take into account additional newer data points. In this example, this allows the model to retain what it has already learned and only adjust the weights by a specified factor. In one or more embodiments, model 112 can be versioned for any iteration. For example, a study or clinical trial can reference the version of the model used. In one or more embodiments, model 112 can be trained on a first clinical trial and then used to predict outcomes of another clinical trial cohort's response to the treatment. This would provide a comparison of two clinical trials. This technique can be repeated over multiple treatments for comparison of multiple clinical trials. In one or more embodiments, model 112 can stratify patients in a clinical trial or otherwise associated with a particular treatment based on the image (e.g., baseline/pre-treatment CT scan) alone.

Figure 2A:
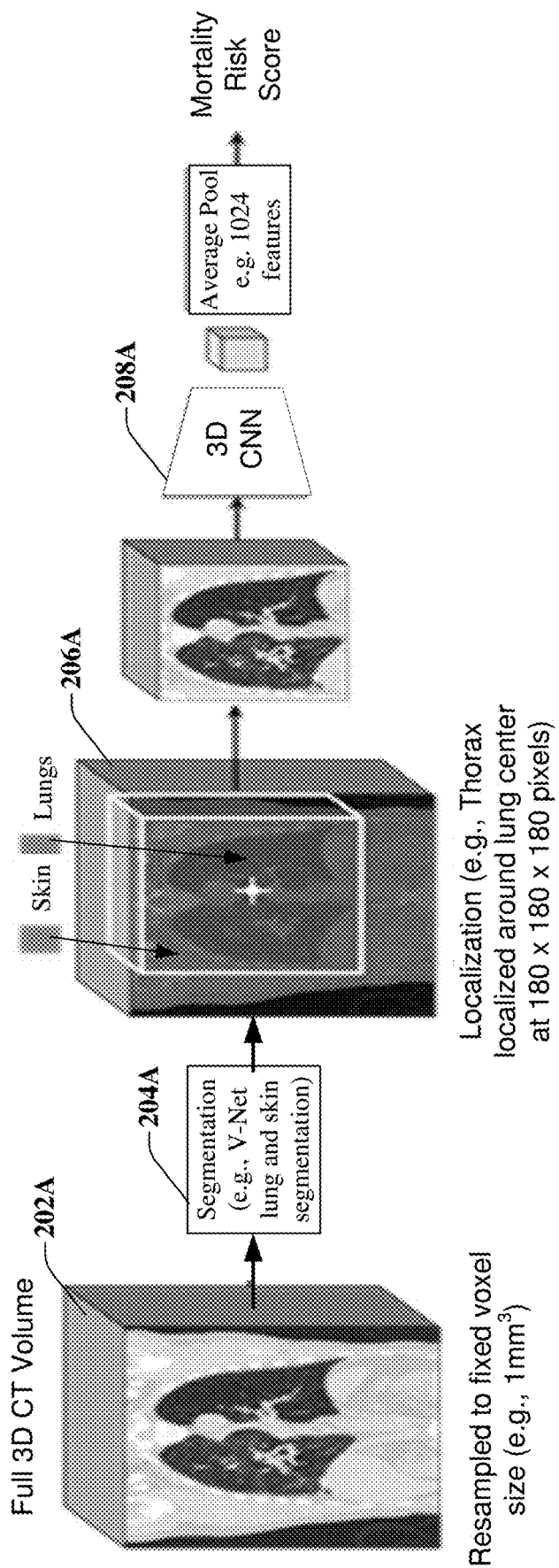
FIG. 2A is a block diagram illustrating an example, non-limiting embodiment of an image-based modeling prediction pipeline functioning within the system of FIG. 1 in accordance with various aspects described herein.

FIG. 2A is a block diagram illustrating an example, non-limiting embodiment of image-based modeling that can function or otherwise be performed within the system of FIG. 1 in accordance with various aspects described herein. The imaging-based prognostication (IPRO) framework 200A can process 3D CT volumes 202A, such as resampling them to a fixed voxel size. Segmentation 204A can be performed and then a localizer 206A (e.g. a thorax localizer) and a 3DCNN 208A can extract imaging features automatically along the axial, sagittal and coronal directions, such as simultaneously. As an example, the localizer 206A can limit the model input to a 3D space (of a selected size) centered on the organ of interest (e.g., lungs), thus excluding features outside of a particular region or volume (e.g., excluding features outside of the thorax, such as the abdomen, and outside of the skin, such as the CT scanner table). The automatically identified thorax region can then be fed into the 3DCNN which outputs probability scores, such as between 0 and 1, indicating mortality at different time intervals (e.g., 1-year, 2-year, and 5-year) for a given CT scan.

While the example illustrated for IPRO framework 200A processes 3D CT volumes 202A to obtain a predicted variable of a mortality risk score, in one or more embodiments the IPRO framework can also be based on 2D images (alone or in combination with 3D images) and the images can be of various types including X-ray, MRI, Ultrasound, Nuclear medicine imaging, and so forth.

The IPRO framework 200A can also provide other predicted variables (in combination with the mortality risk score or in place of it), including one or more of age, sex, weight, ECOG status, smoking status, co-morbidities, cardiac and pulmonary toxicity, TNM stage, pulmonary function, and so forth based solely on the image analysis (or in conjunction with other ingested data).

The IPRO framework 200A can be applied prospectively and/or retrospectively. For instance, predicted variables can be generated based on images ingested by a trained model for individuals where treatment in the clinical trial has not yet started or where the treatment in the clinical trial is finished (which can include clinical trials that have been completed but are being re-evaluated as to their efficacy or for planning related trials). Similarly, independent of any clinical trial, predicted variables can be generated based on images ingested by a trained model for individuals where treatment has not yet started or where the treatment has finished. In one embodiment, the modeling and analysis to generate predictive variables can be commenced during treatment where pre-treatment image(s) are available for the individual(s) and an image-based model has been trained for the organ, disease and/or treatment as described herein. For example, this can be helpful to a physician and patient in determining whether an on-going treatment should be adjusted or changed (e.g., adjusting dosage, changing treatment type, and so forth). While some of the embodiments herein describe detection and prognostication with respect to cancer and tumors, in one or more embodiment, the IPRO framework 200A can be applied to any disease, condition or medical characteristic that allows for image-based detection or evaluation. It should further be understood that the timing of application of the system and methodology can vary and can include being applied after a clinical trial(s) is over, during the clinical trial(s), and/or before the clinical trial(s) has commenced. For example, a clinical trial may have concluded and the manager of the clinical trial desires to retrospectively analyze the clinical trial. In this example, the imaging model and other functions described herein can be applied to various images that were captured at various time periods, such as pre-treatment, on-treatment and/or post-treatment images. In one or more embodiments, the imaging model and other functions described herein can be applied to some or all of the pre-treatment, on-treatment and post-treatment images, to provide an analysis of clinical trial(s), which may have already begun or may have already finished. In one or more embodiments of a retrospective analysis, the same imaging model and same functions can be applied to all (or some) of the pre-treatment, on-treatment and post-treatment images, to provide an analysis of a clinical trial(s), which has already finished.

In one or more embodiments, the IPRO framework 200A can utilize various deep learning techniques and algorithms that can analyze images. For example, different algorithms can be utilized by different models, such as based on the selected algorithm being determined to be more accurate in generating predicted variables for a particular body part or organ. In another embodiment, different algorithms can be utilized by different models being applied to the same body part or organ and the results (e.g., predicted variables at different time intervals) can be compared, such as to confirm accuracy. In yet another embodiment, different algorithms can be utilized by different models being applied to the same body part or organ, where the predicted variables at particular time intervals are selectively taken from the different models, such as based on model A being known to be more accurate at earlier time intervals and model B being known to be more accurate at later time intervals. As another example, a convolutional neural network can be utilized where the images are 2D (e.g., X-ray) while a 3DCNN can be utilized for 3D images (e.g., CT scans). In one embodiment, the best model(s) can be selected and applied according to the particular circumstances, such as the type of images, type of disease, and/or other factors that can influence model efficiency and/or accuracy. In one or more embodiments, future machine learning models that are developed, including future imaging models, can be implemented by the systems and methodologies described herein.

In one or more embodiments, the selection of a particular modeling algorithm for the IPRO framework 200A can be based on performance evaluation. For example, various algorithms can be selected and can be implemented iteratively to determine best performance, most accurate, most efficient or other performance criteria. As an example, different numbers of layers and settings can be implemented for one or different algorithms to avoid overfitting (e.g., the inclusion of dropout layers, batch normalization, and so forth) and evaluate the algorithm performance.

Clinical TNM staging can be a key prognostic factor for cancer patients (e.g., lung cancer) and can be used to inform treatment and/or monitoring. Imaging, such as radiological imaging (e.g., computed tomography), can play a central role in defining the stage of disease. As an example, deep learning applied to pretreatment CTs can offer additional, individualized prognostic information to facilitate more precise mortality risk prediction and stratification.

In one or more embodiments, the selection of the volume size for the IPRO framework 200A can be performed in a number of different ways, such as being predetermined by the algorithm and remaining the same for the organ being analysed via determining organ sizes (from automated segmentations) from multiple datasets and selecting a size that fitted the largest organs.

In one or more embodiments, the IPRO framework 200A can perform pre-processing for images including gathering organ segmentation and extracting an organ box of a particular size (e.g., 360×360×360 mm for the lungs); and/or rescaling the image such that images can be fitted into GPU(s) while retaining as much information as possible. In one or more embodiments utilizing the 3DCNN (which can be other types of machine learning models in other embodiments), a balance between the size of the image and a higher resolution for the image (which can give better performance but can make the model more prone to overfitting) can be determined and maintained. In one or more embodiments, image normalization is implemented to prevent the model from overfitting and can be determined by assessing the training loss/accuracy trend over multiple training iterations (i.e., epochs). In one or more embodiments, clipping (Hounsfield Unit) HU values between −1000 and 1000 (e.g., for thorax images) can be utilized where a range of HU values can improve performance.

In one or more embodiments, the IPRO framework 200A can analyze and reduce bias introduced into the process. For example in one embodiment, the input image(s) can be modified to remove pixels which suggest such bias (e.g., based on scanner used, hospital where acquired, and so forth).

In one or more embodiments, the IPRO framework 200A can capture and analyze multiple organs including a primary organ (e.g., exhibiting a tumor) and a secondary organ (which may or may not be exhibiting a tumor). As an example, the IPRO framework 200A may utilize multiple "arms" in the 3DCNN to learn features from various body parts. This can also include developing segmentation models to extract a 3D box encompassing the particular organ(s).

In one or more embodiments, the IPRO framework 200A can perform post-processing techniques. For example, heatmaps or activation or attention maps can be generated (e.g., utilizing GradCAM or other back propagation techniques and tools) which indicate where greatest attention is placed by the model in a particular image, and which can indicate which parts of the image were of particular importance for predicting the particular variable(s), such as survival. As an example, GradCAM activation maps were generated that indicated that an IPRO applied to the thorax learned to place outsized attention on primary lesions, where on average 54% more attention was placed on primary lesions (0.2458) compared to the average attention throughout the thorax (0.15920), which was statistically significant ($p<0.001$).

In one or more embodiments, an end-to-end fully-automated framework of imaging-based prognostication can ingest images (e.g., CTs) of varying sources and imaging protocols, and can automatically analyse a 3D region encompassing one or more organs and/or their surrounding area, such as the thorax. In one or more embodiments, the IPRO can predict mortality at various time intervals (e.g., 1-year, 2-year, and/or 5-year). In one or more embodiments, the IPRO can predict other variables from the ingested image(s). In one or more embodiments, the IPRO can predict the size and/or shape of tumor(s) in the future at different time intervals. In one or more embodiments, the IPRO can perform its predictions based only on applying the trained model to the particular image, without the need for other medical/user data associated with the patient corresponding to the image. In one or more embodiments, the IPRO can perform its predictions based on applying the trained model to the particular image, in conjunction with other medical/user data (height, weight, age, gender, comorbidity, BMI, etc.) associated with the patient corresponding to the image. In one or more embodiments, IPRO can be combined with TNM staging. In one or more embodiments, the imaging analysis includes a volume surrounding the organ of interest so that the IPRO is not limited to learning prognostic features only from present lesion(s). In one or more embodiments, the IPRO can be utilized without needing or utilizing radiologists (or other users) to manually annotate regions of interest, such as primary tumors. The IPRO provides an improvement in that manual annotation is a time-consuming process, requires radiological expertise, is subject to inter-reader variability, and enforces the implication that only annotated regions of interest are correlated with outcomes.

Figure 2B:
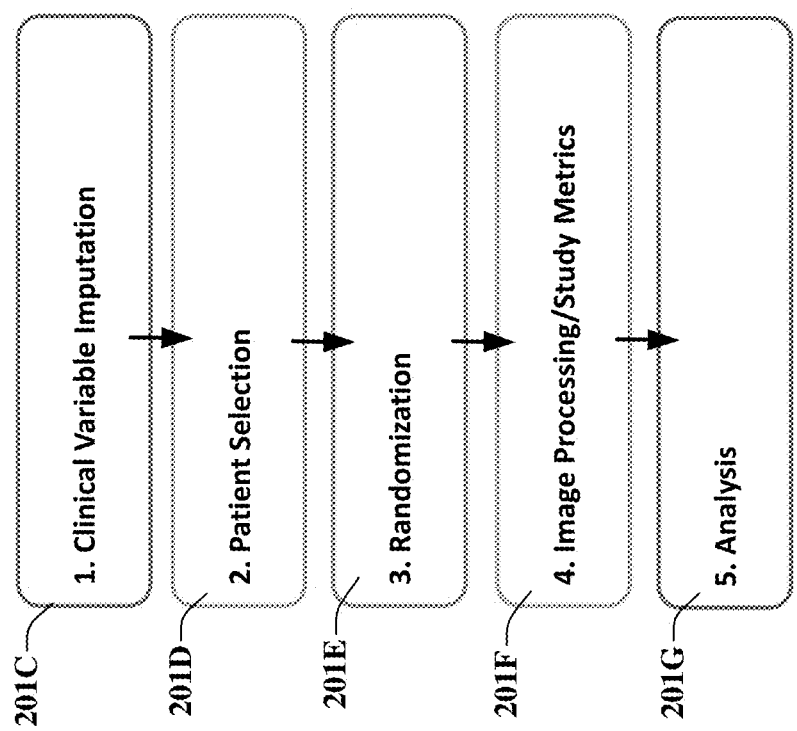
FIGS. 2B-2G are block diagrams illustrating exemplary, non-limiting embodiments of processes functioning within the system of FIG. 1 in accordance with various aspects described herein.

FIG. 2B is a block diagram illustrating an example, non-limiting embodiment of a modeling platform process 201B that employs image-based modeling (e.g., as described with respect to FIG. 2A) to facilitate one or more clinical trials. Modeling platform process 201B can function or otherwise be performed within the system of FIG. 1 in accordance with various aspects described herein. Process 201B includes clinical variable imputation at 201C which can be performed utilizing captured images, such as CT scans. At 201D, patient selection for the clinical trial (e.g., eligibility) can be determined. At 201E, randomization can be determined for eligible candidates that have consented to participate, such as being randomized between an investigational arm (e.g., receives the trial treatment) and a control arm (e.g., does not receive the trial treatment but which can include receiving the standard of care treatment). At 201F, image processing can be performed and study metrics generated such as ingesting images (e.g., follow-up images after trial treatment begins) and performing quality control for the images. At 201G, an analysis can be performed according to the generated predictions from the model being applied to the images (e.g., follow-up images after trial treatment begins). As an example, the analysis allows for managing the clinical trial, including generating predicted variables (e.g., survival data that can be used to generate KM curves including predicted KM curves at different future time intervals) and providing access to the various predictions that have been made, as well as changes that have occurred to the predictions (e.g., between baseline/pre-treatment and/or between follow-up images).

Figure 2C:
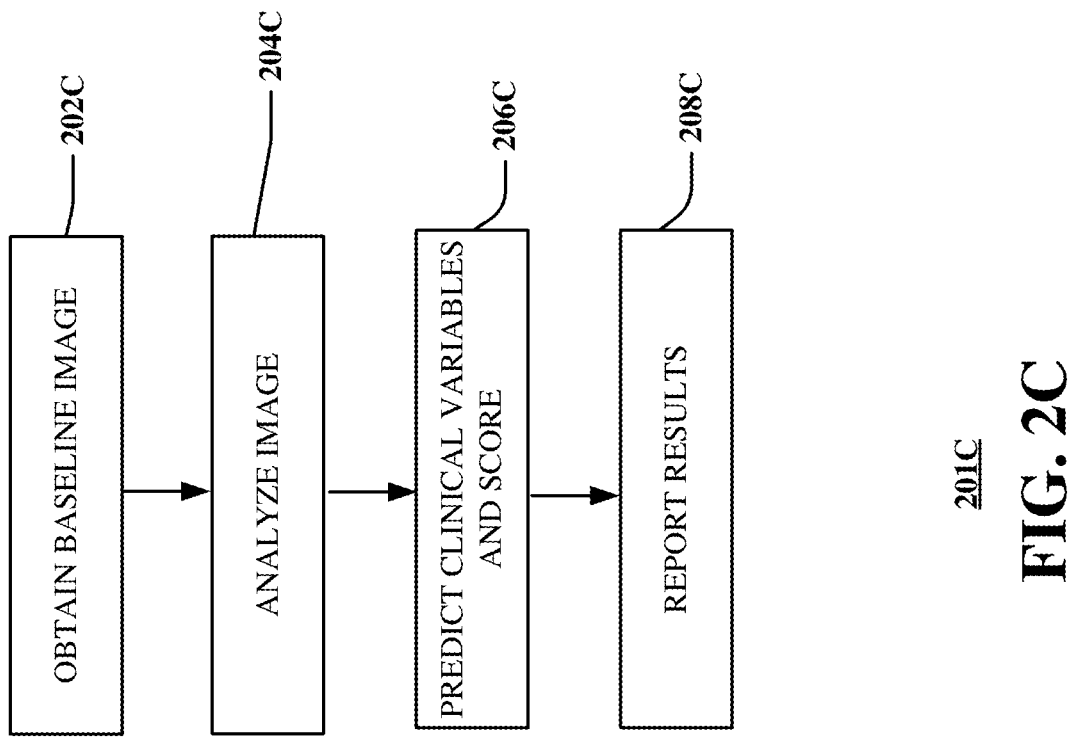

FIG. 2C is a block diagram illustrating an example, non-limiting embodiment of the clinical variable imputation 201C that employs image-based modeling (e.g., as described with respect to FIG. 2A) to facilitate one or more clinical trials and that can function or otherwise be performed within the system of FIG. 1 in accordance with various aspects described herein. Process 201C includes obtaining baseline/pre-treatment images at 202C for each of the potential candidates for clinical trial(s). For example, the radiology department of a particular facility for each candidate can transmit or upload the baseline/pre-treatment images to the modeling platform. At 204C, the baseline/pre-treatment images can be analyzed by the image-based platform according to a trained image-based model (e.g., a model trained as described with respect to FIGS. 1, 2A or elsewhere herein). The training of the image-based model can be based on various datasets (public and/or private sources) that are relevant to the clinical trial (e.g., same disease, same organ, and so forth) which may or may not include images of healthy or otherwise disease-free individuals. In one or more embodiments, the datasets can be of individuals that received the standard of care treatment and/or of individuals that have not received any treatment. The analysis of the baseline/pre-treatment images can include quality control and pre-processing, including de-identification, segmentation and so forth. At 206C, clinical variables and/or scores can be predicted according to the trained image-based model (which may be only based on the baseline/pre-treatment image or may be in conjunction with other medical/user data ingested by the model). As an example and based on the submitted baseline/pre-treatment CT scans of the participants, the modeling platform can predict specific clinical variables, including, but not limited to: age, sex, ECOG status, smoking status, competing mortality risk, cardiac and pulmonary toxicity/AE, TNM stage (including relevant Tumor, Lymph Node and Metastasis classifications), pulmonary function and/or IPRO mortality risk score. At 208C, reporting or otherwise access to the results of the analysis can be provided by the modeling platform. For example, the output of the model can be provided to the referring physician (e.g., oncologist) via an official report. This information can also be provided to other relevant entities, such as the clinical manager or sponsor of the clinical trial.

Figure 2D:
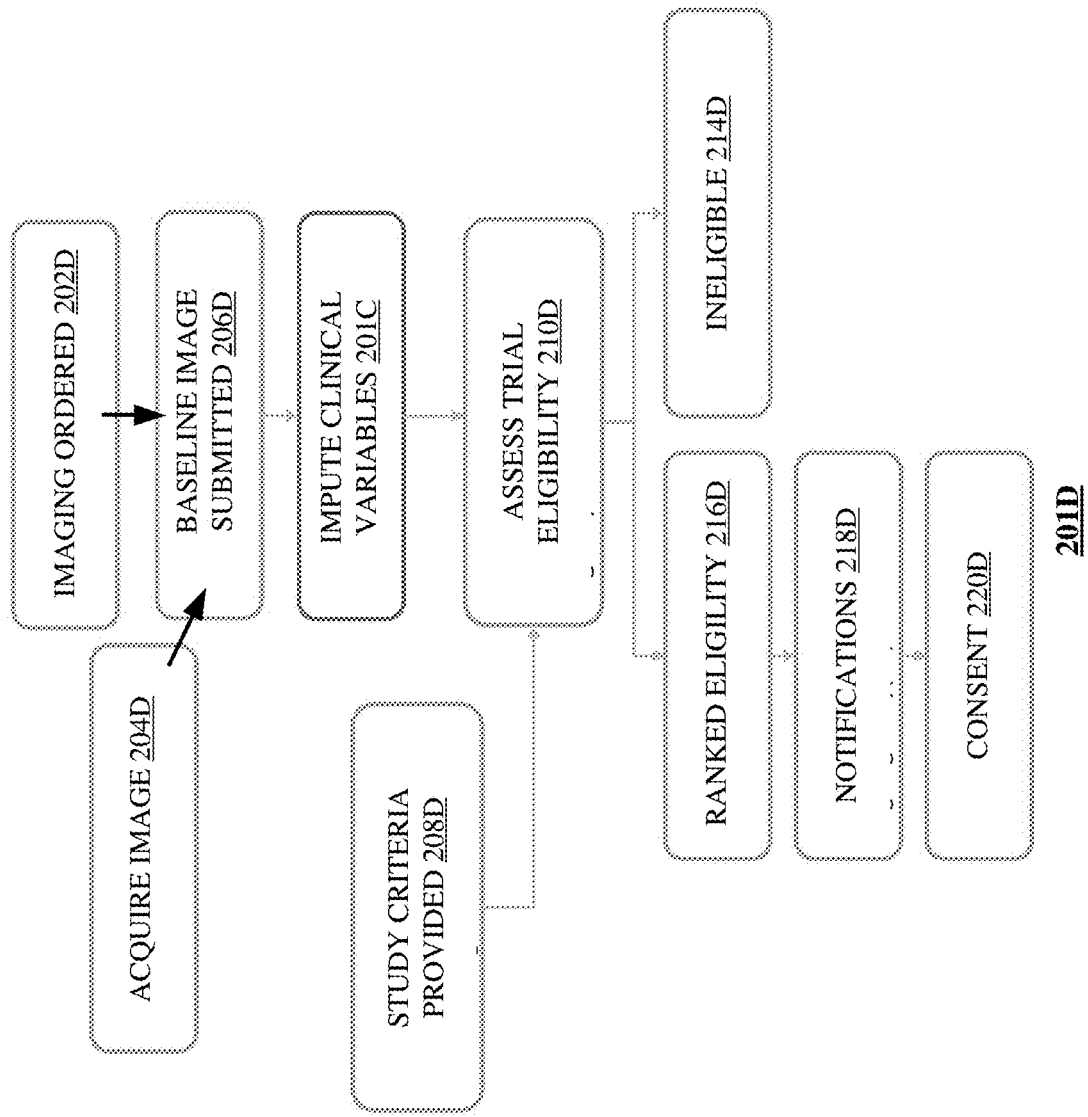

FIG. 2D is a block diagram illustrating an example, non-limiting embodiment of the patient or candidate screening 201D for a clinical trial(s) that employs image-based modeling (e.g., as described with respect to FIG. 2A) to facilitate one or more clinical trials and that can function or otherwise be performed within the system of FIG. 1 in accordance with various aspects described herein. Process 201D includes ordering (e.g., by a candidate's physician) or acquiring images at 202D, 204D which will serve as baseline/pre-treatment images for the candidates. As described herein, the baseline/pre-treatment images can be pre-treatment images of various types including 2D images or 3D images (e.g., CT scans). At 206D, baseline/pre-treatment images can be submitted. For example, the image can be ingested by the model, such as an upload from the imaging department of a facility. At 201C, one or more clinical variables can be imputed (such as described with respect to FIG. 2C). At 208D, study criteria for the clinical trial can be obtained by the modeling platform. For example, study inclusion/exclusion criteria can be incorporated into the modeling platform from various sources, such as from public databases (e.g., clinicaltrials.gov). In one embodiment, the exclusion criteria can include specific anatomical features that are deemed or defined as being ineligible for the clinical trial, such as a lesion that is greater than a particular size. In one embodiment, this exclusion criteria can be applied by the modeling platform according to image analysis that determines the lesion size. At 210D, clinical trial eligibility can be assessed by the modeling platform. For example, using imputed variable(s) for each candidate, and comparing those to the study criteria, patients can be assessed by the modeling platform for trial eligibility. This assessment can be performed with or without user intervention. As described herein, the imputed criteria can include mortality risk scores, as well as other data that is determined from the model based on the image and/or is determined from data provided for the particular candidate.

In one embodiment, there can be multiple clinical trials that are seeking candidates (e.g., managed/commenced by a same entity or different entities). In this example, the modeling platform can determine eligibility for one, some or all of the multiple clinical trials. In one embodiment, where a candidate is eligible for more than one clinical trial, the modeling platform can analyze a best fit trial or otherwise rank the clinical trials from the perspective of the best candidates for a particular trial and/or from the perspective of the best trials for a particular candidate, based on various factors which may or may not be derived from the imputed variable(s) and/or the study criteria.

At 214D, the modeling platform can determine those candidates that are ineligible for the clinical trial(s), such as a candidate that is not eligible for any clinical trials. This determination can be performed with or without user intervention. At 216D, the modeling platform can determine those candidates that are eligible for the clinical trial(s). This determination can be performed with or without user intervention. In one embodiment, ranked eligibility can be performed by the modeling platform based on assessment of ongoing trials and imputed patient data. In one embodiment, the eligibility determination can include ranking candidates for the clinical trial, such as based on predicted risk mortality score, a number of criteria of the study criteria that are satisfied by the particular candidate, or other factors. At 218D, notification can be provided or otherwise generated for eligible candidates. For example, a notification can be sent to a referring physician of the candidate and/or to the candidate indicating that the candidate is eligible for ongoing clinical trial(s) or study (ies). At 220D, consent can be obtained from the candidate, such as a written consent to participate in the particular clinical trial.

Figure 2E:
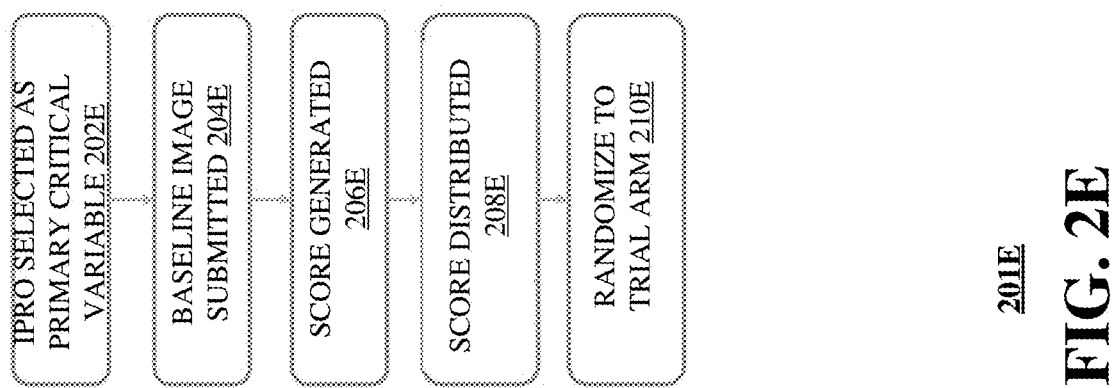

FIG. 2E is a block diagram illustrating an example, non-limiting embodiment of randomization 201E for a clinical trial that employs image-based modeling (e.g., as described with respect to FIG. 2A) to facilitate one or more clinical trials and that can function or otherwise be performed within the system of FIG. 1 in accordance with various aspects described herein. Process 201E includes selecting or otherwise determining (e.g., according to user input) a primary critical variable(s) (e.g., IPRO mortality risk score) that is to be utilized for randomization. In one embodiment, the IPRO mortality risk score can be the sole critical variable or can be used in combination with other selected primary critical variables. At 204E, baseline/pre-treatment images are submitted (e.g., as described with respect to FIG. 2C and/or FIG. 2D). At 206E, the primary critical variable is generated based on the baseline/pretreatment image, such as determining an IPRO mortality risk score from applying model 112 to the baseline/pre-treatment image for the candidate (e.g., as described with respect to FIG. 2C and/or FIG. 2D).

At 208E, the modeling platform can distribute the primary critical variable, such as the IPRO mortality risk score. For example, the modeling platform can provide IPRO mortality risk score to study staff and/or to integrated randomization software (e.g., Interactive Voice/Web Response System (IxRS), Interactive Response Technology (IRT)). At 210E, the candidate can be randomized to a trial arm according to the primary critical variable and an analysis of balancing the trial arms, such as an investigational arm and a control arm. As an example, a candidate can be randomized automatically to a trial arm by the modeling platform per a predefined randomization scheme. The scheme can include balancing the primary critical variables among the investigational and control arm, and/or balancing other candidate criteria amongst the arms. In one embodiment, the IPRO mortality risk score can be included in the randomization determination (e.g., balancing between trial arms) in addition to other stratification factors (e.g., smoking, histology. TMN stage, age, prior treatment, etc.). In one embodiment, a balanced stratification can be achieved by the modeling platform utilizing a single IPRO factor (e.g., the IPRO mortality risk score). In one embodiment, the randomization is performed by the modeling platform and is based on achieving a distribution of predicted survival outcomes before the treatment commences that are equal or within a threshold of each other for the investigational and control trial arms as determined from the predictions generated from applying the image-based model to the baseline/pre-treatment CT scans (or other images). In one embodiment, the randomization can be performed by the modeling platform according to only the predicted variable(s) (e.g., without relying on the imputed variables). In another embodiment, the randomization can be performed by the modeling platform according to the predicted variable(s) in combination with other criterion, such as one or more of the imputed variables (e.g., age, sex, weight, ECOG status, smoking status, competing mortality risk, cardiac and pulmonary toxicity, TNM stage, pulmonary function, or a combination thereof) which can be determined from image analysis and/or determined from other information.

Figure 2F:
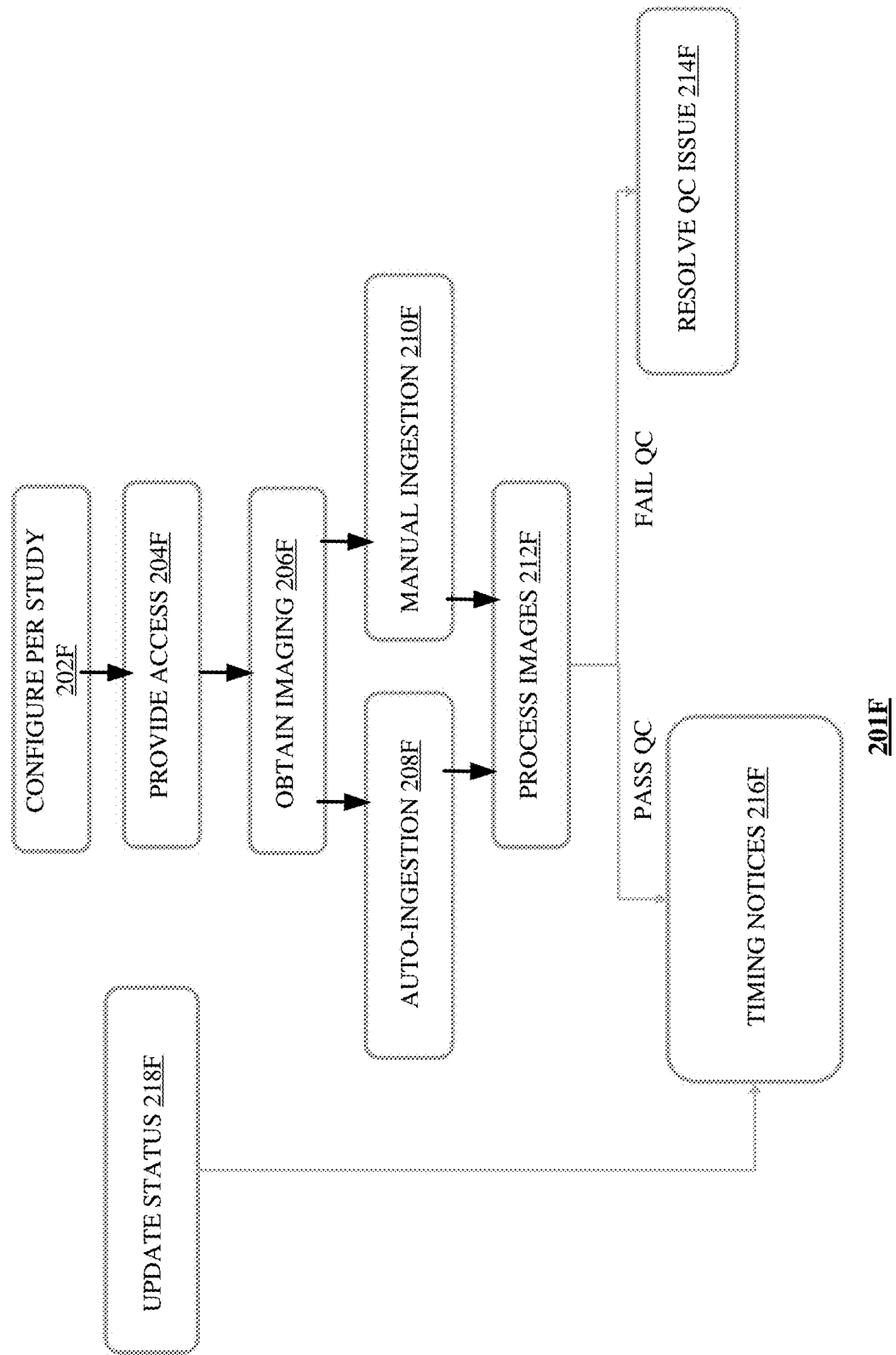

FIG. 2F is a block diagram illustrating an example, non-limiting embodiment of image processing and study metrics 201F for a clinical trial that employs image-based modeling (e.g., as described with respect to FIG. 2A) to facilitate one or more clinical trials and that can function or otherwise be performed within the system of FIG. 1 in accordance with various aspects described herein. Process 201F includes configuring the modeling platform according to parameters or requirements of the particular clinical trial at 202F, providing access and/or selective access to various entities, individuals and/or teams at 204F (as described with respect to FIG. 1), and obtaining imaging at 206F (e.g., follow-up images) such as according to protocol (described in the clinical trial or otherwise defined). For instance, follow-up CT scans may be required every 4-6 weeks or at other time intervals for each of the candidates after the treatment has commenced. At 208F and 210F, automatic or manual ingestion of the images by the modeling platform can occur to enable application of the image-based model. For example, automatic ingestion can include CT scans being pulled from a site Picture Archiving and Communication System (PACS) to the modeling platform via an online web application. As another example, manual ingestion can include CT scans being submitted to the modeling platform via an online web application. At 212F, the images can be processed by the modeling platform. For example, quality control and/or de-identification, as well as other pre-processing steps can be performed on each of the images.

At 214F, if it is determined that the image did not satisfy the quality control requirements then the particular issue can be resolved. For example, a site can be automatically contacted to resolve queries regarding the particular image. This can include a request for re-capturing the CT scan or other remedial action to assist the image in passing the requirements. This step is repeated until the image passes the quality control requirements. At 216F, if it is determined that the image did satisfy the quality control requirements then timing notices can be generated with respect to the particular candidate and/or with respect to the clinical trial. For example, based on expected images (per the protocol), the modeling platform can inform or otherwise indicate to the user/viewer when images are expected, as well as a percent completed per timepoint. In this example, the user/viewer can be one or more individuals of the clinical manager, sponsor, or pharmaceutical company associated with management of the clinical trial.

In one embodiment at 218F, the modeling platform can update status for the particular candidate. For example, the modeling platform can integrate with EDC (or other study systems) to update patient status.

Figure 2G:
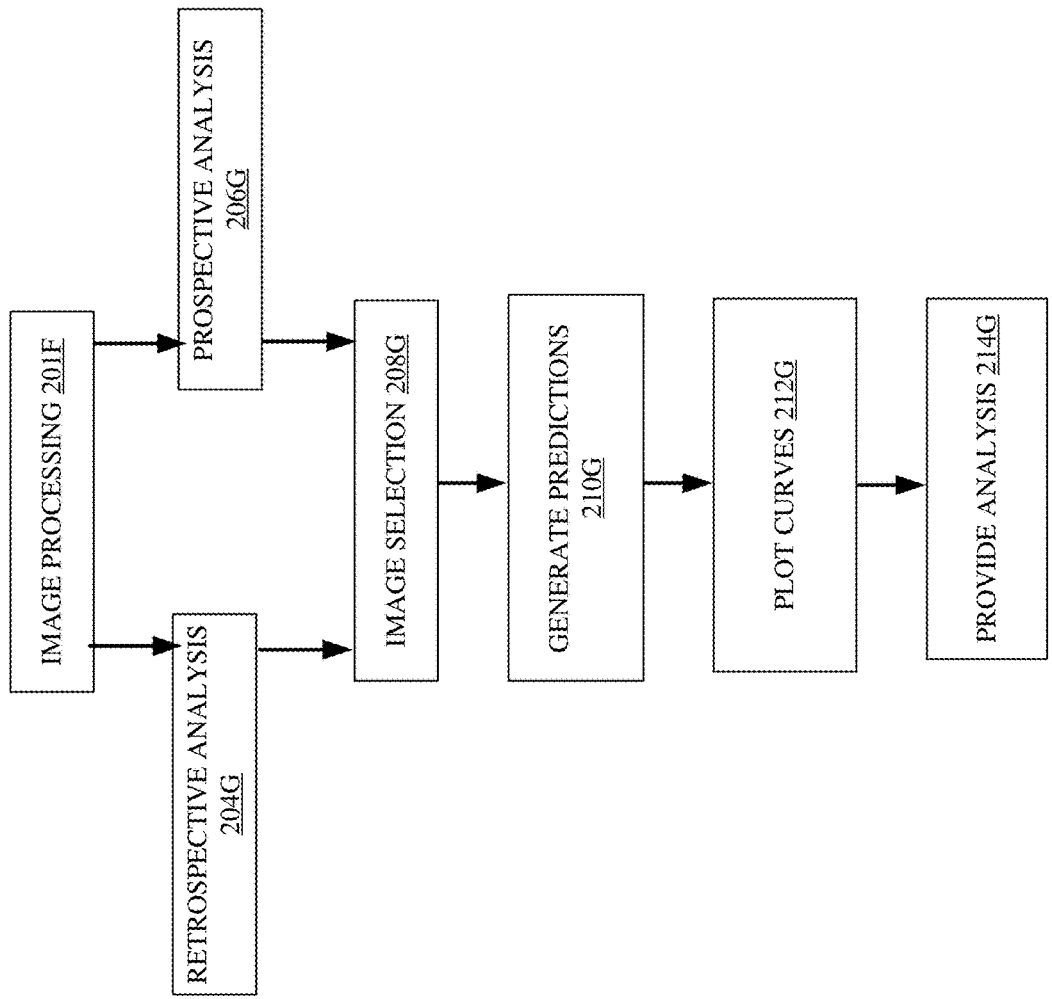

FIG. 2G is a block diagram illustrating an example, non-limiting embodiment of an analysis 201G for a clinical trial that employs image-based modeling (e.g., as described with respect to FIG. 2A) to facilitate one or more clinical trials and that can function or otherwise be performed within the system of FIG. 1 in accordance with various aspects described herein. Process 201G can begin with the image processing 201F which can be a retrospective analysis 204G, for example some or all of the sets of images (e.g., baseline/pre-treatment and/or follow-up images) are available (e.g., the clinical trial has already begun or has already ended) or can be a prospective analysis 206G, for example the trial is commencing or is on-going and only some of the sets of images (e.g., baseline/pre-treatment and/or follow-up images) are available. At 208G, image selection can be provided. As an example, a user/viewer can determine which of baseline/pre-treatment or follow-up image(s) are to be utilized in the analysis. For instance, using a "study day" timeline, images can be selected to be included or excluded in the analysis (see FIG. 3A). At 210G, predictions can be generated or otherwise obtained (e.g., from a data storage where the predictions had already been generated and stored by the image-based model). For example, based on selected and/or available data, survival, IPRO score, tumor size and tumor response predictions are generated or otherwise obtained). At 212G, representations of the data can be generated, such as curves, graphs, and so forth. For example, the predicted KM curves can be developed and plotted against the actual KM curve as well as other standard statistical models. At 214G, the analysis can be provided. For example, the final analysis can include: a comparison of the modeling platforms predictions vs other models; based on prospective Go/No Go criteria, a determination of when the program should be accelerated or considered futile; and/or baseline population (by arm) analysis.

In one embodiment, the analysis is performed retrospectively as described herein, to identify a sub-population of an investigational arm that had a significant improvement (e.g., improvement in survival above a particular threshold) so that the treatment can be focused on the particular subpopulation (e.g., individuals with similar characteristics as the sub-population). As an example, the identified sub-population can be examined for common, similar or otherwise correlated characteristics (physiological, behavioral, etc.) and a subsequent clinical trial can be run utilizing these common characteristics as study criteria for eligibility of candidates.

While for purposes of simplicity of explanation, the respective processes are shown and described as a series of blocks in FIGS. 2A-2G, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein. Further, the processes described in FIGS. 2A-2G can be performed in whole or in part by one or more devices described with respect to FIG. 1 or other devices described herein. In one or more embodiments, the processes described in FIGS. 2A-2G can be performed in whole or in part retrospectively or prospectively.

Example 1

A retrospective study was performed providing an end-to-end deep learning approach in which the entire thorax of individual lung cancer patients was automatically evaluated to generate an IPRO score. Using publicly available pretreatment CTs split across a 5-fold validation, an assessment was performed as to how IPRO compares to and complements TNM staging for purposes of 1-year, 2-year, and 5-year mortality risk predictions in the withheld validation set. IPRO's ability to stratify patients across and within TNM stages was evaluated. The distribution of known prognostic clinical variables like age, sex. TNM stage, and histology across IPRO's risk deciles was reviewed and the amount of attention placed on lung lesions was quantified. It was determined in this Example 1 that CT imaging features were predictive of mortality risk when quantified using deep learning technologies (e.g., IPRO) which can enhance image-based prognostication and risk stratification in lung cancer patients.

A fully-automated IPRO technique was developed using deep learning to predict 1-year, 2-year, and 5-year mortality from pretreatment CTs of stage I-IV lung cancer patients. Using 6 publicly available datasets from The Cancer Imaging Archive, a retrospective five-fold cross validation was performed using 2,924 CTs of 1,689 patients, of which 1,212 had available TNM staging information. Association of IPRO and TNM staging with patients' actual survival status from the date of CT acquisition was compared, and an "Ensemble" risk score that combines IPRO and TNM staging via generalized linear regression was assessed. IPRO's ability to stratify patients within individual TNM stages using hazard ratios and Kaplan-Meier curves was also evaluated. In this Example 1, the IPRO showed similar prognostic power (C-Index 1-year: 0.70, 2-year: 0.69, 5-year: 0.67) compared to that of TNM staging (C-Index 1-year: 0.68, 2-year: 0.70, 5-year: 0.69) at 1 and 2 years but underperformed TNM staging in predicting 5-year mortality. The Ensemble risk score yielded superior performance across all time points (C-Index 1-year: 0.76, 2-year: 0.76, 5-year: 0.75). IPRO stratified patients within TNM stages, discriminating between highest and lowest risk quintiles in stages I (HR: 7.44), II (HR: 5.51), III (HR: 3.93), and IV (HR: 1.57). This Example 1 illustrated that IPRO showed potential for enhancing imaging-based prognostication and risk stratification in lung cancer patients.

Lung cancer remains a leading cause of cancer death in North America and worldwide. The TNM staging system is used to classify the anatomic extent of cancerous tissue. This system helps to discriminate between patients in distinct groups, called TNM stages, and informs management of patients with cancer. In patients with lung cancer, TNM staging is a key prognostic factor, driving treatment and monitoring decisions. Radiological imaging, particularly computed tomography, plays a central role in defining the stage of disease. Analysis of CTs currently relies upon manual localization, classification, and measurement of nodules and is subject to inter- and intra-observer variability. More precise prognostication, as shown by the results of this Example 1 (and other embodiments described herein), can help clinicians make personalized treatment decisions that can, for example, spare a "low"-risk patient from aggressive treatment that might increase the risk of adverse effects, or, conversely, more proactively treat and monitor a "high"-risk patient.

CNNs, which are a form of deep learning, may be able to identify and quantify complex features in images that are not readily discernible to the naked eye. The use of CNNs to derive mortality risk prediction in patients with lung cancer, which rely upon manual steps, such as segmenting the primary lesion, or placing seed points or bounding boxes over regions of interest, would be inefficient. A fully automated approach, in which a system would analyze the entire thorax in a CT, may complement traditional TNM staging of lung cancer patients and provide greater prognostic power in an easily accessible manner.

In the Example 1, publicly available pretreatment CTs of lung cancer patients were identified that also contained survival outcomes. Imaging data and associated clinical information were obtained from six datasets made available in The Cancer Imaging Archive (TCIA) (Table 1). A total of 1,689 patients were selected that had a biopsy confirmed lung cancer diagnosis, survival information, and at least one pretreatment axial CT. Mortality and CT acquisition dates were used to compute survival time and status at specified censoring dates (i.e., 1 year, 2 years, and 5 years). Cases that were lost to follow-up prior to a given censoring date were excluded from training and validation (see FIG. 2L).

TABLE 1

Patient characteristics in six experimental datasets.

| Dataset | Number of Patients | Number of CTs | Gender (Male/Female) | Median Age (min, max) |
|---|---|---|---|---|
| NLST | 954 | 2,189 | 570/384 | 63 (55, 74) |
| NSCLC Radiomics | 422 | 422 | 290/132 | 68 (34, 92) |
| NSCLC Radiogenomics | 193 | 193 | 124/69 | 69 (24, 87) |
| TCGA-LUSC | 35 | 35 | 21/14 | 72 (39, 83) |
| TCGA-LUAD | 24 | 24 | 9/15 | 69 (42, 84) |
| LungCT Diagnosis | 61 | 61 | — | — |
| Total | 1,689 | 2,924 | 1,014/614 | 68 (24, 92) |

Given that some patients had multiple pretreatment CTs, validation was limited to only the final (i.e., most recent) pretreatment CT to assess the performance of IPRO and TNM staging. Multiple TNM staging types (e.g., clinical and pathological) and TNM staging editions (e.g., both the 6th and 7th edition of the AJCC staging system) were sometimes available for a given patient. Clinical TNM staging was prioritized over pathological TNM staging and used the most recent AJCC staging edition available for a given patient. Cases that were missing TNM staging were included in training but excluded from validation. Table 2 provides an overview of the distribution of TNM stages and survival status amongst the 5-year validation dataset, which contained 1,212 patients (605 alive, 607 deceased) with a median age of 64 (range: 43, 88) and in which 62% were male.

TABLE 2

Number of patients in 5-fold validation set by clinical TNM stage and outcome at 1 year, 2 years, and 5 years post image acquisition.

| Time from image acquisition | Number of Patients by Stage survived (deceased) | | | | |
|---|---|---|---|---|---|
| | I | II | III | IV | Total |
| 1 year | 556 (15) | 94 (21) | 272 (60) | 164 (30) | 1,086 (126) |
| 2 years | 523 (48) | 72 (43) | 184 (148) | 115 (79) | 894 (318) |
| 5 years | 438 (133) | 47 (68) | 81 (251) | 39 (155) | 605 (607) |

In the Example 1, scanning protocols were varied between sites and cases (e.g., radiation dose, use of contrast, slice spacing, anatomic regions included); as such all CTs were preprocessed to standardize model inputs and improve model generalizability. This included resampling each CT to 1 mm slice thickness and pixel spacing, and clipping Hounsfield Unit values at −1,000 to 1,000. Any CTs with greater than 5 mm slice thickness or fewer than 50 slices were excluded.

As shown in FIG. 2A, the IPRO framework consisted of a thorax localizer and a 3DCNN that extracted imaging features automatically along the axial, sagittal and coronal directions, simultaneously. The thorax localizer consisted of an algorithm that limited the model input to a 3D space (36 cm×36 cm×36 cm in size) centered on the lungs, thus excluding features outside of the thorax (e.g., abdomen) and outside of the skin (e.g., CT scanner table). The automatically identified thorax region was then fed into the 3DCNN which outputted probability scores between 0 and 1 indicating 1-year, 2-year, and 5-year mortality for a given CT.

The architecture of the 3DCNN was based on a neural network called InceptionNet. This architecture enabled features to be learned without being prone to overfitting, suitable for medical applications where individual data points tend to be large but the number of patients are few. To make the neural network three-dimensional, transfer learning was first applied to stabilize the network using ImageNet, and then intermediate layers were duplicated in a new temporal dimension (i.e., z-axis). The resulting architecture allowed for entire 3D CT volumes to be fed into the 3DCNN without further modifications.

A five-fold cross validation across six lung cancer datasets was performed to train and validate the IPRO which involved randomly splitting the data into 5 groups, while ensuring class balance based on survival status and TNM staging distribution. Each group was then iteratively withheld for validation while training on the remaining 4 groups until each group was used for validation. Models were trained to predict mortality as posterior probabilities between 0 (low-risk) and 1 (high-risk) at time t, given 3D CT volumes, where t=1, 2 or 5 years. To compare the prognostic power of IPRO to that of TNM staging, generalized linear regression models were trained using solely TNM staging information in the same 5-fold cross-validation to predict 1-year mortality. The "glm" library in R was used for training and predicting regression models on eight TNM sub-types. Ensemble models (which combined IPRO and TNM staging) were generated by training a linear regression model per fold, where the inputs were TNM staging and IPRO mortality risk scores at time t. Risk scores were compared with survival status at time t using concordance index (C-index) and area under the receiver operating characteristic curve (AUC). Pearson $r^2$ correlations between IPRO scores and time-to-event from date of CT acquisition were examined. Statistical significance between models was assessed using a two-sample t-test.

To assess stability of IPRO scores in a test-retest scenario, intra-class correlation coefficient (ICC) and mean absolute differences (MAD) between IPRO risk scores generated from the CTs in the RIDER dataset were evaluated. ICC of >0.90 was considered an "excellent" agreement. IPRO was used to stratify lung cancer patients, where Kaplan-Meier curves were generated per risk group. Each group was defined as a subset of the patients in the validation set sorted by ascending IPRO mortality risk scores. To quantify differences between predicted highest- and lowest-risk groups defined as quintiles (i.e., 20%) or deciles (i.e., 10%) of the patients with either the highest or lowest IPRO scores, the coxph function was used to report hazard ratio (HR) and log rank p-values. All statistical analyses were performed in R.

Associations between the outcome predictions and known prognostic clinical variables like age, sex, TNM stage, and histology across IPRO's risk deciles were explored. Gradient-weighted Class Activation Mapping (GradCAM) activation maps were generated as a visual explanation to indicate on which anatomical regions within the thorax IPRO placed attention to generate its mortality risk prediction. The middle (i.e., 8th) layer of the network was used to generate attention weights during backpropagation resulting in a 3D attention mask, offering both spatial information and relevance to the final classification layer. Attention maps were further normalized and scaled to fit the original 3D image space. Such visualizations offer insight into a subset of the features learned in the 3DCNN and the deep learning based predictions. To quantify model attention placed on lesions, CTs from a subset of patients in the validation set were interpreted by radiologists, who manually detected and volumetrically segmented lung lesions. For each CT scan, the average attention value in the thorax was calculated and compared to the average attention placed within the segmented lesions.

Figure 2H:
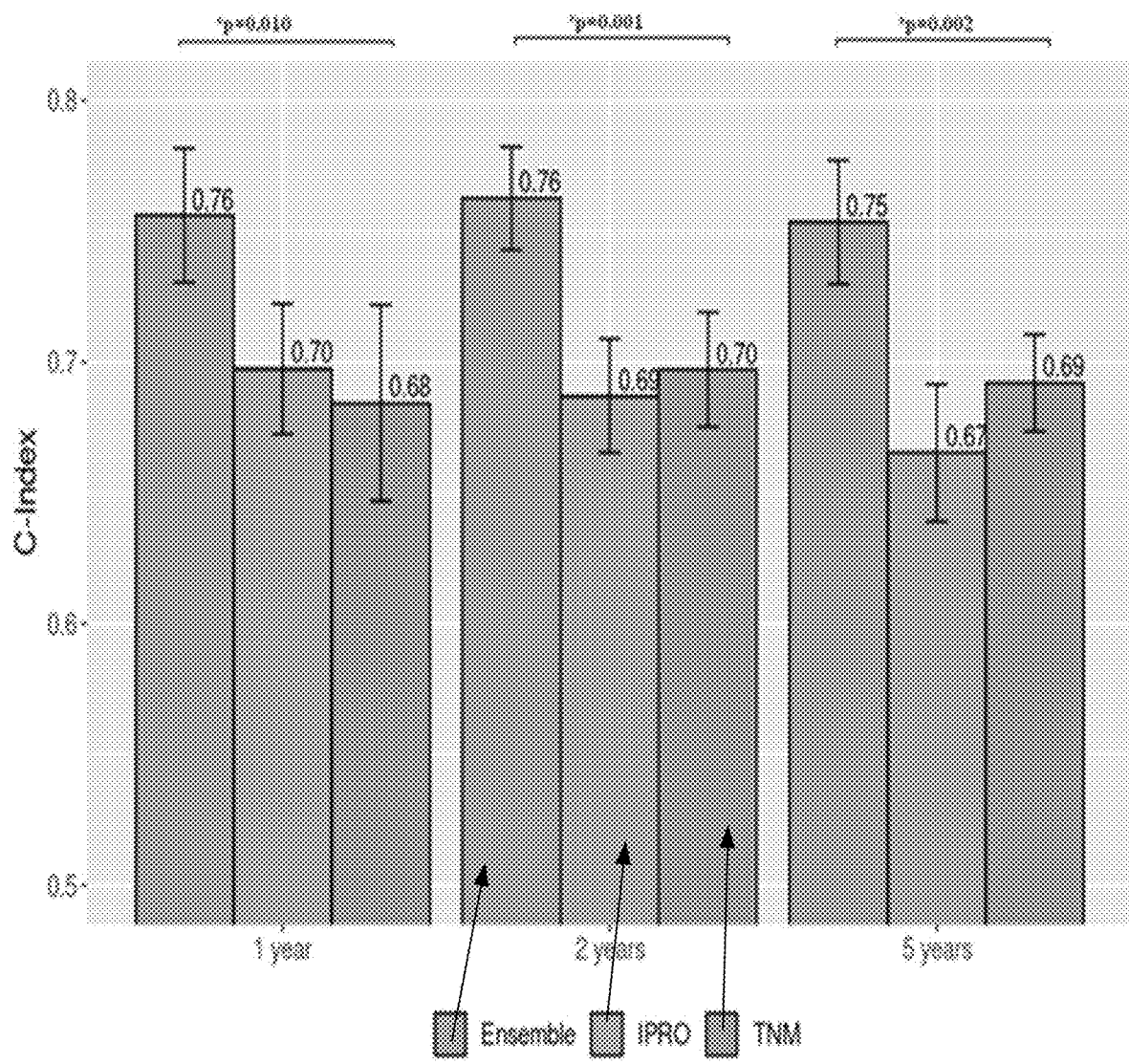
FIG. 2H is a graphical comparison of mortality risk prediction accuracy at 1 year, 2 years, and 5 years for a particular example 1 of the image-based modeling prediction pipeline of FIG. 2A.

IPRO showed evidence of similar prognostic power compared to that of TNM staging in predicting 1-year and 2-year mortality but underperformed TNM staging in predicting 5-year mortality (See FIG. 2H). The Ensemble model, which combines IPRO and TNM staging information, yielded significantly superior prognostic performance at all three time intervals ($p \leq 0.01$) when compared to that of TNM alone. Table 3 summarizes results across metrics including C-index, AUC, and Pearson $r^2$.

TABLE 3

Average C-Index, AUC and $r^2$ for mortality risk prediction models across 5 folds.

| | C-Index | | | AUC | | | Pearson $r^2$ | | |
|---|---|---|---|---|---|---|---|---|---|
| | 1 year | 2 years | 5 years | 1 year | 2 years | 5 years | 1 year | 2 years | 5 years |
| IPRO Standard Dev. | 0.697 ± 0.02 | 0.687 ± 0.02 | 0.665 ± 0.03 | 0.714 ± 0.01 | 0.716 ± 0.03 | 0.706 ± 0.04 | 0.159 ± 0.03 | 0.174 ± 0.03 | 0.178 ± 0.03 |
| TNM Standard Dev. | 0.684 ± 0.04 | 0.697 ± 0.02 | 0.692 ± 0.02 | 0.699 ± 0.03 | 0.731 ± 0.03 | 0.777 ± 0.02 | 0.203 ± 0.03 | 0.233 ± 0.04 | 0.240 ± 0.05 |
| Ensemble Standard Dev. | 0.756 ± 0.03 | 0.763 ± 0.02 | 0.754 ± 0.02 | 0.776 ± 0.02 | 0.803 ± 0.01 | 0.840 ± 0.02 | 0.293 ± 0.03 | 0.333 ± 0.04 | 0.341 ± 0.05 |

*$p < 0.001$ for all reported metrics

Figure 2I:
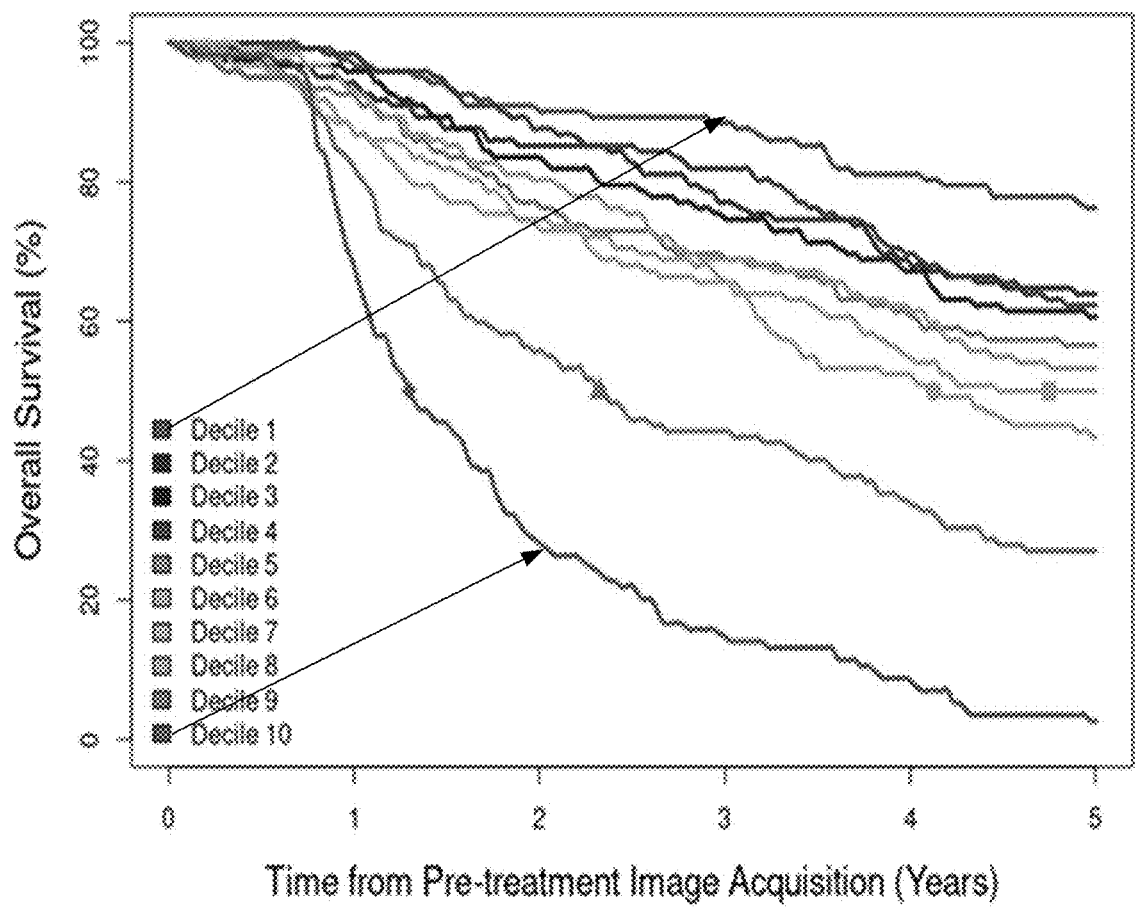
FIG. 2I illustrates Kaplan-Meier curves and corresponding data for 5-year IPRO mortality risk deciles (includes all TNM stages) for the particular example 1 of the image-based modeling prediction pipeline of FIG. 2A.

Stability assessment of IPRO using the test-retest RIDER dataset revealed strong correlations between the two consecutively acquired CTs, with average intra-class correlation coefficients of 0.87, 0.83 and 0.80 for the 1-year, 2-year and 5-year IPRO scores, respectively. Mean absolute differences between IPRO scores per RIDER patient were consistently less than 0.05 (1-year: 0.04, 2-year: 0.04, 5-year: 0.03). Kaplan-Meier curves were generated in FIG. 2I and show risk stratification by IPRO deciles of all lung cancer patients (stages I-IV) included in the 5-year validation. Hazard ratios (HRs) between each decile and the highest risk group (i.e., decile 10) were statistically significant. Hazard ratios between each decile and the lowest risk decile (i.e., decile 1) were statistically significant for deciles ≥6. Kaplan-Meier curves illustrating the 1-year and 2-year IPRO deciles were generated and are shown in FIGS. 2M and 2N.

Figure 2J:
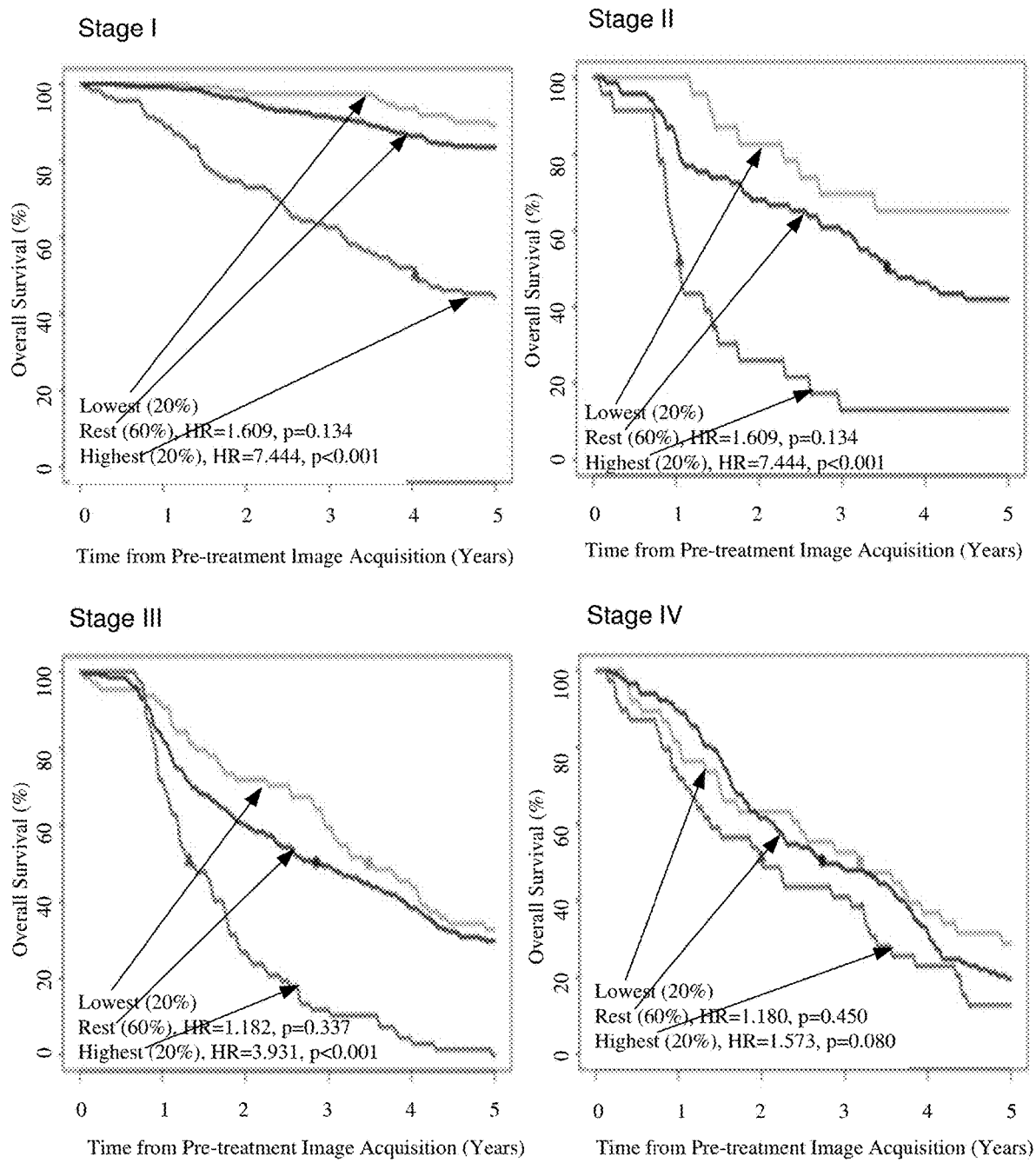
FIG. 2J illustrates stage-specific Kaplan-Meier curves for 5-year IPRO mortality risk quintiles for the particular example 1 of the image-based modeling prediction pipeline of FIG. 2A.
Figure 2K:
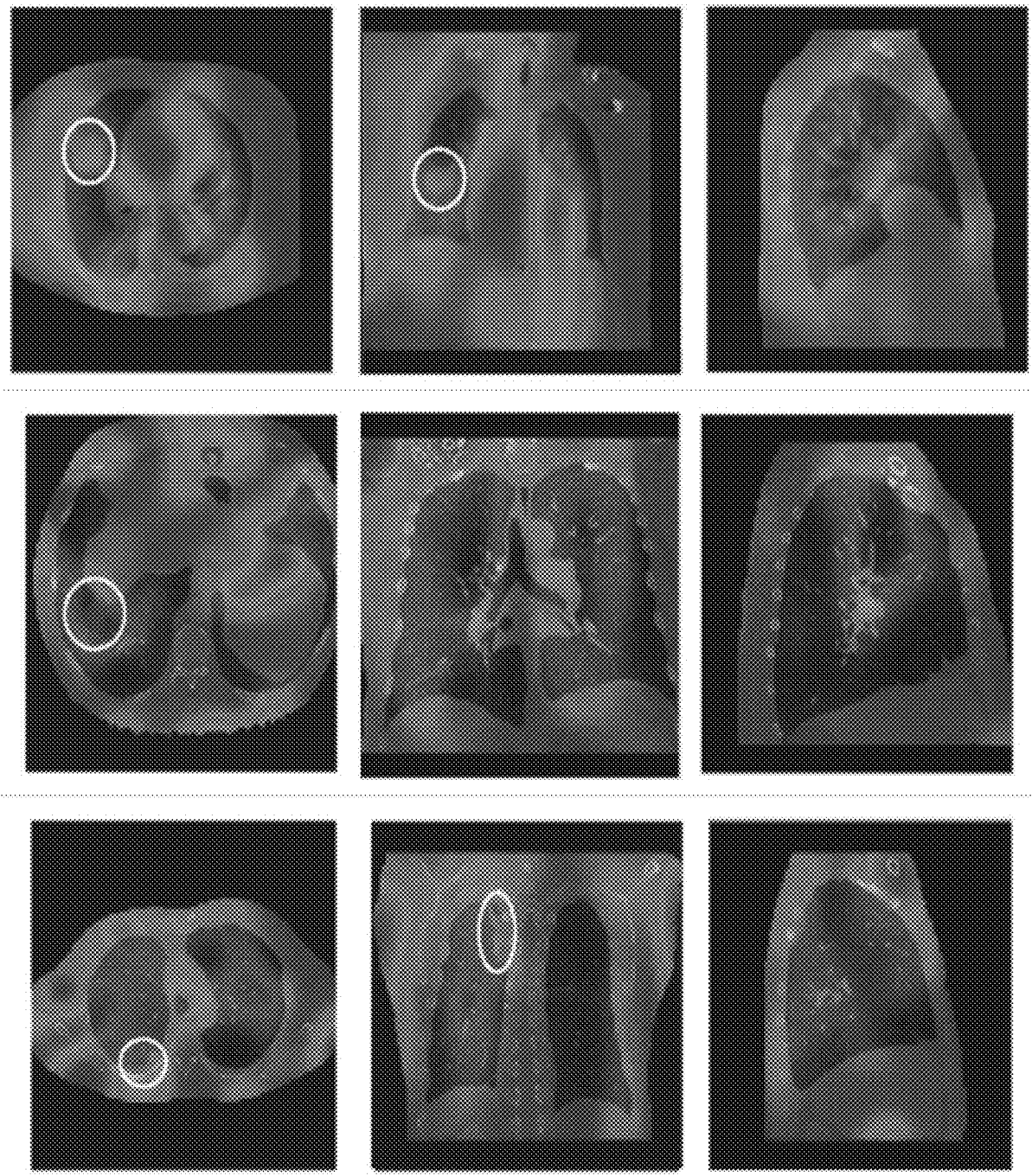
FIG. 2K illustrates activation or attention maps for patients who received high IPRO mortality risk scores in stage I (top) and stage II (middle and bottom) for the particular example 1 of the image-based modeling prediction pipeline of FIG. 2A.
Figure 2L:
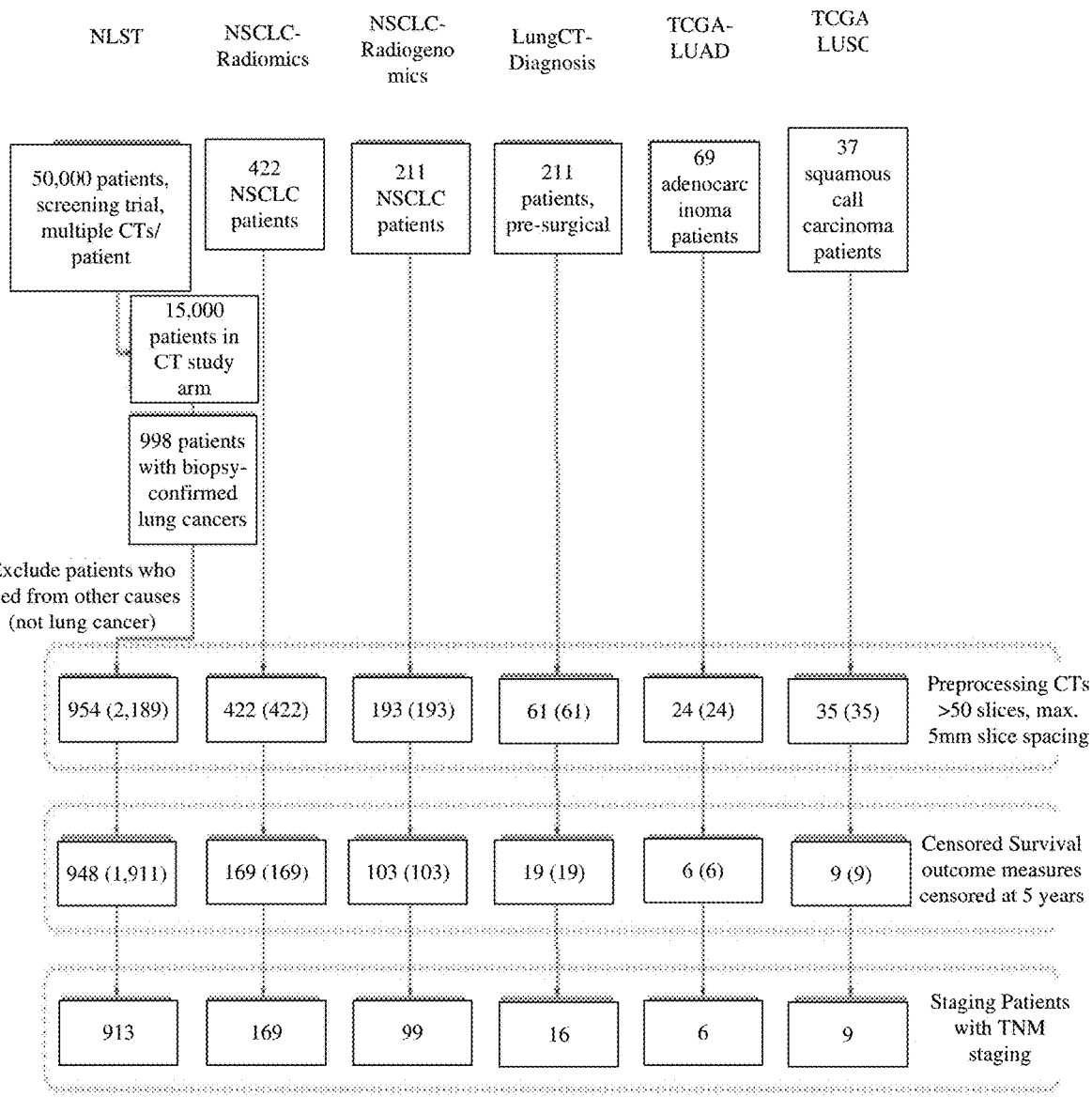
FIG. 2L illustrates exclusion criteria for experimental datasets for the particular example 1 of the image-based modeling prediction pipeline of FIG. 2A.
Figure 2M:
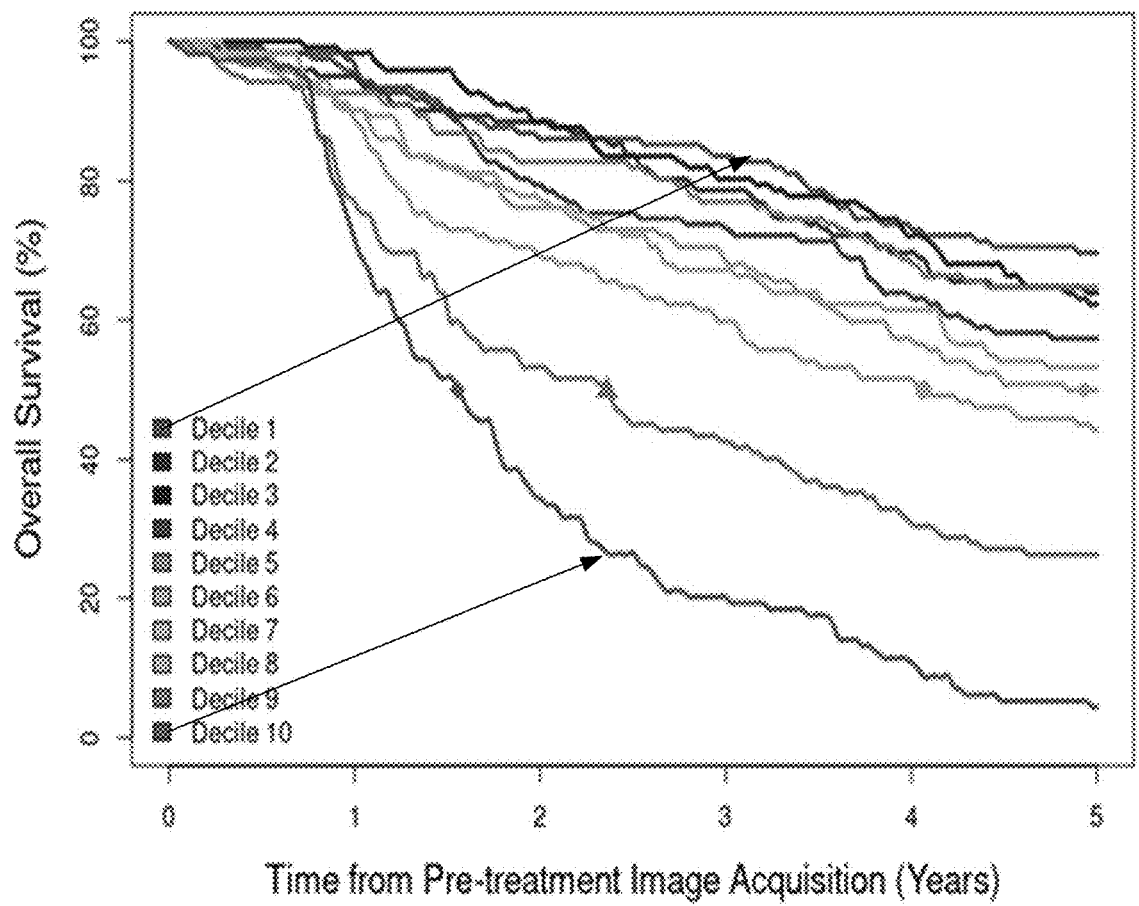
FIG. 2M illustrates Kaplan-Meier curves and corresponding data for 1-year IPRO mortality risk deciles (includes all TNM stages) for the particular example 1 of the image-based modeling prediction pipeline of FIG. 2A.
Figure 2N:
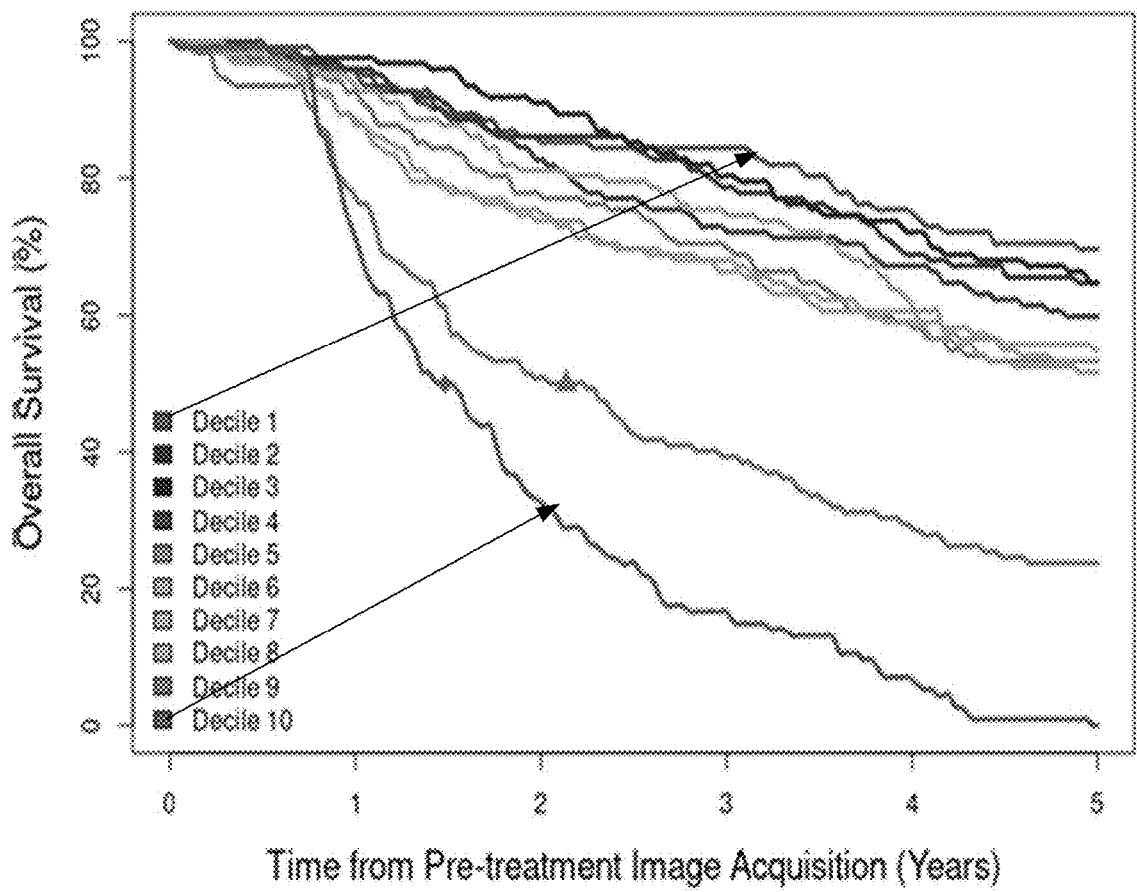
FIG. 2N illustrates Kaplan-Meier curves and corresponding data for 2-year IPRO mortality risk deciles (includes all TNM stages) for the particular example 1 of the image-based modeling prediction pipeline of FIG. 2A.
Figure 2O:
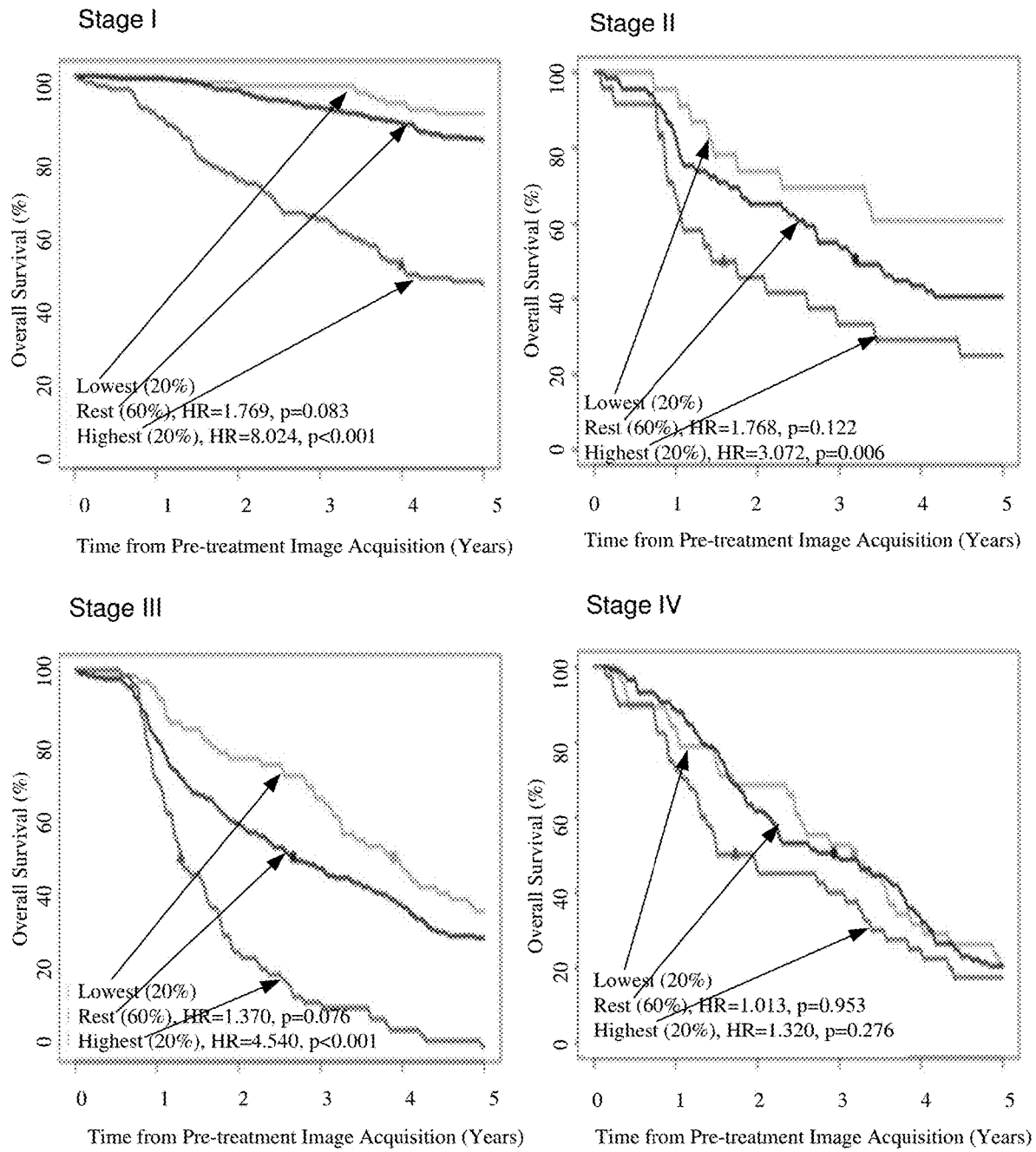
FIG. 2O illustrates stage-specific Kaplan-Meier curves for 1-year IPRO mortality risk quintiles for the particular example 1 of the image-based modeling prediction pipeline of FIG. 2A.
Figure 2P:
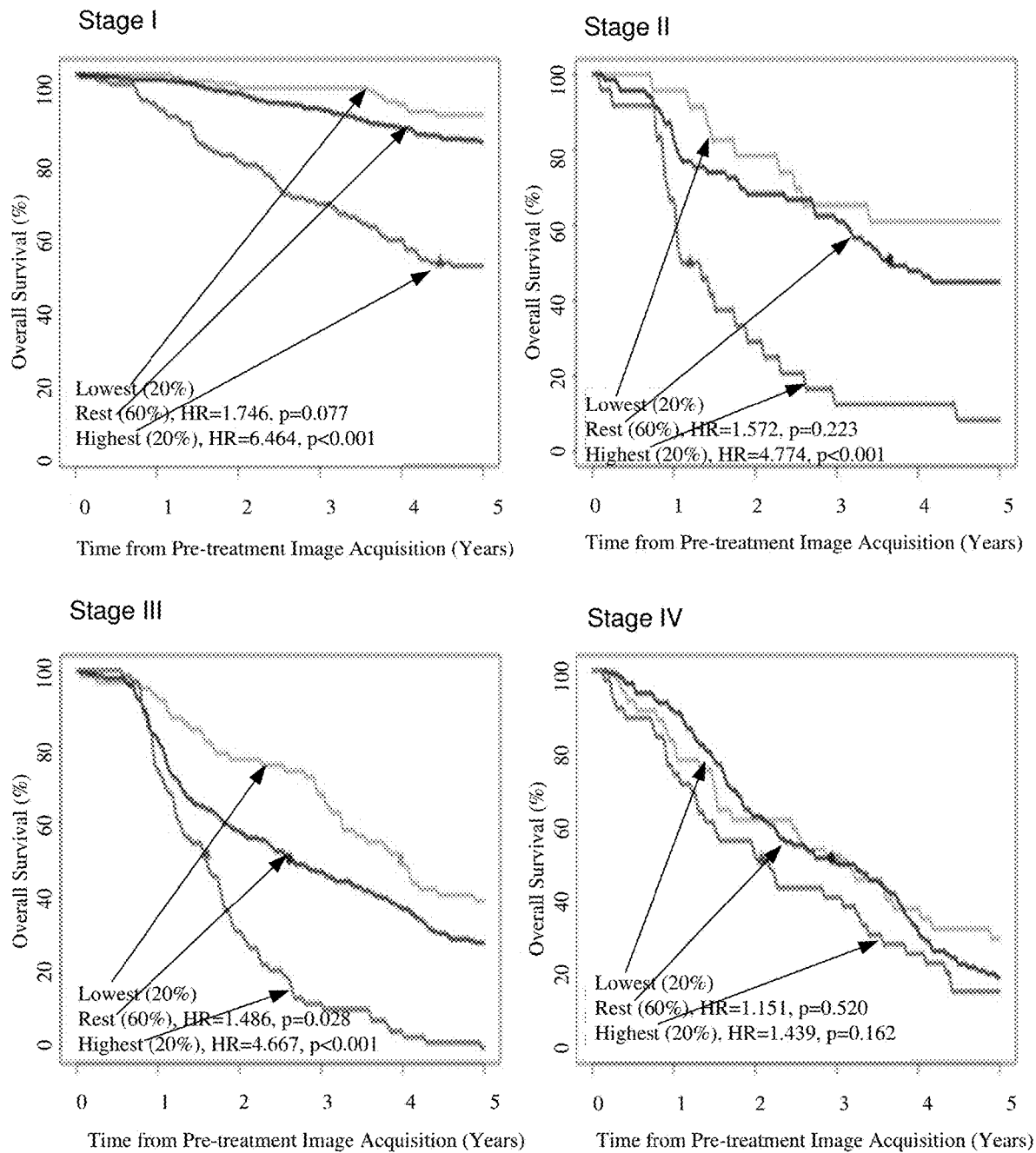
FIG. 2P illustrates stage-specific Kaplan-Meier curves for 2-year IPRO mortality risk quintiles for the particular example 1 of the image-based modeling prediction pipeline of FIG. 2A.

IPRO's ability to stratify patients within each TNM stage via high-risk and low-risk quintiles was assessed (see FIG. 2J). Stage I patients in the highest risk IPRO quintile had a 7.4-fold (95% CI 4.0-13.8, p<0.001) increased 5-year mortality hazard compared to stage I patients in the lowest risk quintile. Similarly, in stage II and stage III, patients in the highest risk IPRO quintile had a 5.5-fold (95% CI 2.4-12.7, p<0.001) and 3.9-fold (95% CI 2.6-6.0, p<0.001) increased 5-year mortality hazard compared to stage II and stage III patients in the lowest risk quintile, respectively. Across all TNM stages, the weakest patient stratification existed for stage IV patients where the highest risk IPRO quintile had a 1.6-fold (95% CI 0.9-2.6, p=0.080) increased 5-year mortality hazard compared to stage IV patients in the lowest risk quintile. Kaplan-Meier curves were generated by TNM stage illustrating the 1-year and 2-year IPRO quintiles and are shown in FIGS. 2O and 2P.

To further explore IPRO's 5-year mortality predictions, the distribution of known prognostic variables including age, sex, TNM stage, and histology across the IPRO risk deciles (Table 4) was assessed. Comparing the characteristics of patients IPRO deemed lowest risk (decile 1) to those deemed highest risk (decile 10), the median age increases from 62 to 68 years and the sex composition shifts from 32.0% male in the lowest risk patients to 67.9% male in the highest risk patients. The most common histological subtype in patients comprising the lowest risk decile was adenocarcinoma (41%), while squamous cell carcinoma (38%) and large-cell carcinoma (24%) accounted for the majority of highest risk patients. Lung cancer patients diagnosed as TNM stages I & II account for 73.0% of patients in the lowest risk decile but only 29.8% of patients in the highest risk decile.

TABLE 4

Distribution of known prognostic factors by IPRO risk decile including age, sex, TNM stage and histology subtype.

| IPRO Risk Decile | Median Age | Sex* (M/F) | Stage | | | | Histology* | | | | |
|---|---|---|---|---|---|---|---|---|---|---|---|
| | | | I | II | III | IV | SqCC | AC | SCC | LCC | Other |
| 1 (low) | 62 | 39/83 | 83 | 6 | 16 | 17 | 12 | 50 | 12 | 3 | 45 |
| 2 | 64 | 58/64 | 73 | 3 | 23 | 23 | 34 | 37 | 7 | 4 | 40 |
| 3 | 63 | 56/64 | 68 | 8 | 23 | 23 | 22 | 45 | 14 | 3 | 36 |
| 4 | 63 | 68/53 | 62 | 7 | 30 | 23 | 30 | 41 | 11 | 5 | 34 |
| 5 | 64 | 82/40 | 60 | 7 | 27 | 28 | 23 | 50 | 19 | 3 | 27 |
| 6 | 64 | 80/40 | 55 | 14 | 27 | 26 | 24 | 44 | 15 | 7 | 30 |
| 7 | 65 | 100/16 | 51 | 15 | 33 | 23 | 32 | 45 | 10 | 5 | 24 |
| 8 | 65 | 96/25 | 58 | 15 | 28 | 21 | 35 | 38 | 11 | 4 | 33 |
| 9 | 67 | 84/32 | 44 | 23 | 45 | 10 | 34 | 41 | 3 | 12 | 26 |
| 10 (high) | 68 | 76/36 | 17 | 17 | 80 | 0 | 42 | 20 | 0 | 27 | 23 |

*excludes 20 patients that are missing sex and histology information.

GradCAM activation maps indicated that IPRO learned to place outsized attention on lesions. On average, twice the amount of attention was placed on lesions (0.248) compared to the average attention placed on the thorax (0.120). GradCAM activation maps were reviewed to qualitatively assess on which anatomical regions within the thorax IPRO placed attention to generate the 5-year mortality risk prediction. In FIG. 2K, three sample cases are provided depicting areas that received the greatest attention (red) and the least attention (blue). Hand-drawn white ellipses (not visible to IPRO) denote areas containing primary lesions.

Based on the results of this Example 1, it is demonstrated that deep learning can provide additional prognostic information based on both known and unknown features present in CTs in a quantifiable, continuous variable. The end-to-end fully-automated framework of IPRO can ingest CTs of varying sources and imaging protocols, and can automatically analyse a 3D region encompassing the thorax. IPRO predicted mortality consistently and accurately at 1-year, 2-year, and 5-year time intervals, and generated similar performance to TNM staging. By combining IPRO with TNM, the Ensemble model showed improved performance across all time intervals, suggesting that IPRO- and human-derived features are complementary. By encompassing the anatomical structures comprising the thorax, IPRO is not limited to learning prognostic features only from present lung lesion(s). This approach has the benefit of not needing radiologists to manually annotate regions of interest, such as primary tumors. Manual annotation is a time-consuming process, requires radiological expertise, is subject to inter-reader variability, and enforces the implication that only annotated regions of interest are correlated with outcomes.

In reviewing regions of the CT volume that received the greatest attention by IPRO (FIG. 2K), it was determined that IPRO gravitated towards tissue comprising primary lesions, indicating that IPRO learned that this tissue has prognostic value. Given that lesion annotations were not provided during training, this showed that features used by IPRO correlate with those defined in manual image interpretation guidelines such as TNM or RECIST 1.1. More interesting are the peritumoral areas also highlighted in the attention maps (FIG. 2K), indicating such areas hold additional prognostic insight. Known prognostic variables such as age and sex for patients within each risk group (Table 4) revealed that those patients in the highest risk group (decile 10) were on average 6 years older and mostly male compared to those in the lowest risk group (decile 1). Histology subtypes in decile 10 were also more likely to exhibit large cell carcinoma and squamous cell carcinoma subtypes. Given the incorporation of the entire chest in the model, not only characteristics of the tumor, lymph nodes and metastasis, other potential useful information, such as coronary artery calcification, size of the heart, body composition, or pulmonary emphysema may have been learned and used by the model. In one embodiment, training and evaluating of region-specific 3DCNNs can be performed to better derive anatomic origins of IPRO's predictions.

The primary component of IPRO is an end-to-end 3DCNN that, unlike two-dimensional neural networks that learn from features in only the XY dimension (i.e., from a single CT slice), learns a series of feature maps at multiple scales across an additional dimension (i.e., Z), capturing millions of patterns not easily discernible to the naked eye. This can help IPRO incorporate richer features like volume of tumors and features in peritumoral tissue that span multiple CT slices, rather than just a single 2D slice. This Example 1 predicts mortality risk for lung cancer patients and incorporates a wider range of pretreatment CTs from multiple datasets and sites.

Staging classification systems are not a primarily prognostic tool, but instead can be a way to provide a consistent means of communication, allowing physicians to exchange information about an individual tumor or group of tumors. Nonetheless, the anatomic extent of disease can be a major factor affecting prognosis and can help in selecting the appropriate treatment approach. Clinical trials comparing different treatment regimens for lung cancer, for example, use TNM staging categories as inclusion/exclusion criteria. In this context and based on the results of this Example 1, despite the lack of detailed information regarding tumor biology and type of treatment offered, IPRO provided at least similar prognostic insight when compared to TNM staging.

In this Example 1, IPRO was able to stratify patients within the same TNM stage. Particularly in stage I, II and III, there are clear distinctions in survival outcomes between the IPRO highest-risk and lowest-risk quintiles. While TNM staging has prognostic power, the ability to further separate high and low risk subgroups within the same stage is an improvement. In one or more embodiments described herein, studies incorporating follow up CTs during and after treatment may be used to further refine mortality prediction.

IPRO's complementary insight via predictive data such as mortality risk may intensify treatment and monitoring of high-risk patients (e.g., at the clinician's discretion), while watchful waiting approaches for low risk patients may assist in avoiding aggressive treatment that might unnecessarily increase risk of adverse effects or reduce quality of life. In one or more embodiments, the IPRO can train and validate predictive models according to larger, independent datasets, as well as in prospective studies. In one or more embodiments, the datasets for training and validation can be expanded to different stages of cancers, different ages, and/or different habits (e.g., smoking vs non-smoking). In one or more embodiments, treatment (which is a major determinant of patient prognosis after a diagnosis of lung cancer) can be incorporated or otherwise utilized by the IPRO model, which in the Example 1 described above was based exclusively on pretreatment imaging.

In this Example 1, to enable the framework to adapt to multiple scanning protocols, V-Net segmentation models were developed to identify and contour the lungs and skin automatically. Such segmentation masks were used to mask out artifacts outside the body and navigate the model to a fixed 3D box centered in the thorax to encapsulate both lungs. The V-Net was based on a deep segmentation model that has been used in medicine and can adapt to multiple organs and tissue types. In IPRO, two separate V-Net models were trained: one to identify regions encased in the body (i.e., within the skin), and the other to segment the lung air space. The skin segmentation mask was used to eliminate artifacts such as the table, blanket, etc., whereas the lung segmentation mask acted as a guide for centering the 3D box (360×360×360 pixels) to encapsulate the lungs. The 3D box centered on the lungs was further downscaled by a factor of 2 and was used as the input for the 3DCNN.

To train both V-Nets, publicly available NSCLC-Cetuximab (RTOG-0617) dataset was used, containing CTs from 490 patients, in which organs at risk including the lungs and skin were contoured for radiotherapy treatment planning. Scans were selected containing annotated regions for lung_cntr or lung_ipsi, and skin, and distributed into training and test sets as shown in Table 5. CT volumes and contours were then rescaled to a size of 100×128×128 pixels to fit into GPU memory. As a post-processing, hole filling was applied to lung segmentation masks to remove spurious regions. Performance of the both V-Nets on held-out test sets were determined and are illustrated in Table 6.

TABLE 5

Number of CTs used for training lung and skin segmentation V-Net models.

|  | Train | Test |
|---|---|---|
| Lung Segmentation | 389 | 97 |
| Skin Segmentation | 384 | 95 |

TABLE 6

Performance of lung and skin segmentation V-Net models. Standard deviation between scans is provided in brackets.

|  | Intersection Over Union | Sørensen-Dice coefficient |
|---|---|---|
| Lung Segmentation Standard Deviation | 81.20 ± 10.81 | 89.03 ± 10.13 |
| Skin Segmentation Standard Deviation | 87.91 ± 18.08 | 92.20 ± 14.43 |

3DCNN training was performed over ten epochs with a learning rate of 5e-7 and a batch size of 48. Model parallelization was used across 8 GPUs to speed up training, taking ~11 hours per fold. Five percent of the training set was allocated for the tuning set which was used to set the number of training iterations and weight decay parameters. An lr-finder open source library was used prior to training to initialize the learning rate. To encourage generalizability, Dropout was applied to the final layers of each IPRO model and a focal loss function was adopted to deal with extreme class imbalance.

To assess stability of IPRO's predictions, an independent publicly available dataset, RIDER, was used consisting of 32 patients diagnosed with lung cancer. Each patient underwent two chest CTs within 15 minutes using the same imaging protocol, therefore only minute changes were visible between scans.

FIG. 3A is an illustrative embodiment of a GUI 300A. The GUI 300A can serve as an illustrative embodiment of a user interface that can be accessed or selectively accessed by various devices to provide various information to various individuals, such as patients, healthcare providers, clinical trial managers, pharmaceutical companies, and so forth. In one embodiment, access to the GUI 300A can be by way of a trial dashboard where an entity involved in multiple clinical trials can access information for each of them.

As an example, GUI 300A can be a trial view that provides access to buttons for an overview, data management, and analysis of the clinical trial. For instance, GUI 300A can provide event estimation information such as survival data (e.g., KM curves) to be generated (based on the image-based model applied to the baseline/pre-treatment and/or follow-up images of the clinical trial) and/or presented according to a selection of particular images as shown in the option "time point." The data, such as the KM curves, can be shown for the investigational arm, the control arm or both (as is depicted in FIG. 3A). For example, a user/viewer can determine which of baseline/pre-treatment and/or follow-up image(s) are to be utilized in the analysis. For instance, using a "study day" timeline, images can be selected to be included or excluded in the analysis. In one embodiment, the 300A allows a viewer to toggle on or off the image predictions for any follow-up images such that if toggled on then the KM curve will include those images in the predictions.

GUI 300A depicts KM curves based on data generated from applying the image-based algorithm on images (e.g., baseline/pre-treatment and/or follow-up images) that have been ingested so far and the KM curves are the predicted KM curves based on that data. As an example, the prediction can be a time to mortality as of the date of image acquisition.

GUI 300A depicts KM curves where the investigational arm is performing (according to survival) better than the control arm which is indicative of or otherwise shows or measures the treatment effect for the clinical trial. In this example, the control arm can include digital twins for one, some or all of the actual candidates in the investigational arm, where the digital twins (and its corresponding predicted variables) are generated by the image-based model from the baseline/pre-treatment image of the particular candidate with or without incorporation of other medical user data into the modeling. In one or more embodiments, the control arm can be made of only digital twins, such as a one-to-one correspondence of digital twins with actual candidates (which are in the investigation arm). In other embodiments, the control arm may include only actual candidates; or may include actual candidates along with digital twins of actual candidates from the investigational arm. As explained herein, the analysis (which includes generating data by applying the image-based model to the baseline/pre-treatment and/or follow-up images) can be prospective such as during an on-going trial where treatment has not yet finished (e.g., predicting the treatment effect) or can be retrospective such as where the clinical trial has been completed.

FIG. 3B is an illustrative embodiment of a GUI 300B. The GUI 300B can serve as an illustrative embodiment of a user interface that can be accessed or selectively accessed by various devices to provide various information to various individuals, such as patients, healthcare providers, clinical trial managers, pharmaceutical companies, and so forth. GUI 300B can allow for image-based predictions to be generated which can in some embodiments complement traditional imaging interpretation frameworks. For instance, the GUI 300B can allow for annotations to be manually entered. In another embodiment, the annotations are generated by the image-based model. Other information can be provided, such as activation maps that indicate regions of attention in the organ according to weighting by the model.

In one or more embodiments, the modeling platform can streamline customizable imaging workflows, increase reproducibility of imaging interpretation, and/or generate (e.g., with or without user input or user assistance) annotations for ML research and biomarker discovery.

FIG. 3C is an illustrative embodiment of a GUI 300C. The GUI 300C can serve as an illustrative embodiment of a user interface that can be accessed or selectively accessed by various devices to provide various information to various individuals, such as patients, healthcare providers, clinical trial managers, pharmaceutical companies, and so forth. In this example, the user/viewer can be one or more individuals of the clinical manager, sponsor, or pharmaceutical company associated with management of the clinical trial. In one embodiment, GUI 300C can be accessed via the data management button for the clinical trial which shows current image acquisition (e.g., 105 of 105 baseline/pre-treatment images acquired; 101 of 105 follow-up one images acquired, and so forth) to facilitate managing the clinical trial.

FIG. 3D is an illustrative embodiment of a GUI 300D. The GUI 300D can serve as an illustrative embodiment of a user interface that can be accessed or selectively accessed by various devices to provide various information to various individuals, such as patients, healthcare providers, clinical trial managers, pharmaceutical companies, and so forth. For example, based on expected images (per the protocol), the modeling platform can inform or otherwise indicate to the user/viewer when images are expected, as well as a percent completed per timepoint. In this example, the user/viewer can be one or more individuals of the clinical manager, sponsor, or pharmaceutical company associated with management of the clinical trial. GUI 300D provides for projected completion information and further indicates for this example that about 50% of the images have been ingested. GUI 300D also provides information regarding imaging deviations, such as indicating imaging quality or incorrect format. GUI 300D can also indicate what images (or the number thereof) have been uploaded, de-identified, and/or quality controlled.

FIG. 3E is an illustrative embodiment of a GUI 300E. The GUI 300E can serve as an illustrative embodiment of a user interface that can be accessed or selectively accessed by various devices to provide various information to various individuals, such as patients, healthcare providers, clinical trial managers, pharmaceutical companies, and so forth. For instance, the GUI 300E (e.g., a trial view) can show information indicating the status of the clinical trial, such as subjects screened, screen failures, subjects enrolled, which may be broken down by various criteria such as site names, investigators, and so forth. Other information, including event estimation information, survival data, KM curves, can be generated (according to predictions from applying the image-based models to the images as described herein) and presented.

FIG. 3F is an illustrative embodiment of a GUI 300F. The GUI 300F can serve as an illustrative embodiment of a user interface that can be accessed or selectively accessed by various devices to provide various information to various individuals, such as patients, healthcare providers, clinical trial managers, pharmaceutical companies, and so forth. In one embodiment, the GUI 300F can be a patient view accessed by one or more of the devices 120, 130, 135 to view patient-specific data that is related to a particular candidate without providing access to a remainder of the graphical user interface (e.g., data of other candidates). In one embodiment, the GUI 300F can include baseline/pre-treatment and follow-up images of the organ or body part that has been utilized by the model for predictions. In one embodiment, the GUI 300F allows for annotations to be made to images and/or provides for automated annotations based on determined points of interest (e.g., points of interest as determined by the image-based model).

In one embodiment, the GUI 300F can include a predicted image(s) of the organ or body part at a future time(s) that is generated based on the image-modeling of the baseline/pre-treatment and/or on-treatment images, and/or based on the predicted variables and/or the predicted on-treatment variables. As an example, the predicted image(s) of the organ or body part at the future time(s) can be generated based on predicted tumor size, predicted tumor shape, predicted growth rate, predicted tumor shape change, and/or predicted tumor location (which can be generated based on the image-modeling of the baseline/pre-treatment and/or on-treatment images). GUI 300F can be used by the healthcare provider to facilitate treatment and treatment decisions for the particular patient as described herein.

Figure 3G:
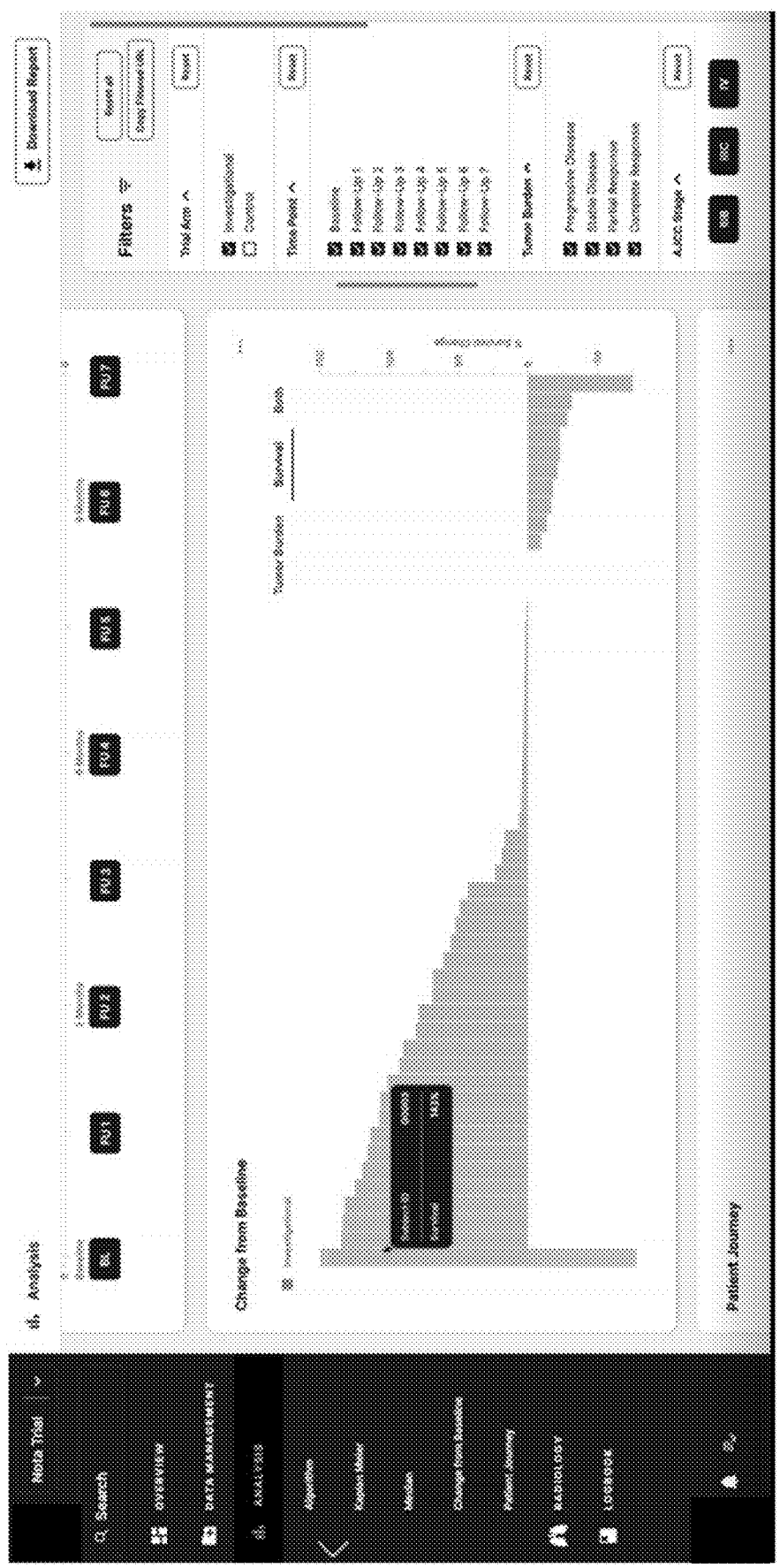

FIG. 3G is an illustrative embodiment of a GUI 300G. The GUI 300G can serve as an illustrative embodiment of a user interface that can be accessed or selectively accessed by various devices to provide various information to various individuals, such as patients, healthcare providers, clinical trial managers, pharmaceutical companies, and so forth. GUI 300G provides information regarding changes to predicted survival such as for the investigational arm patients. For example, the subject ID 00003 is predicted to survive 143% longer than their baseline prediction based on applying the image-based model to the most recent image for the patient. GUI 300G can also selectively provide tumor burden information and changes from baseline such as for the investigational arm patients. In one embodiment, GUI 300G can also selectively provide predicted survival information, tumor burden information and/or changes from baseline for the control arm.

Figure 3H:
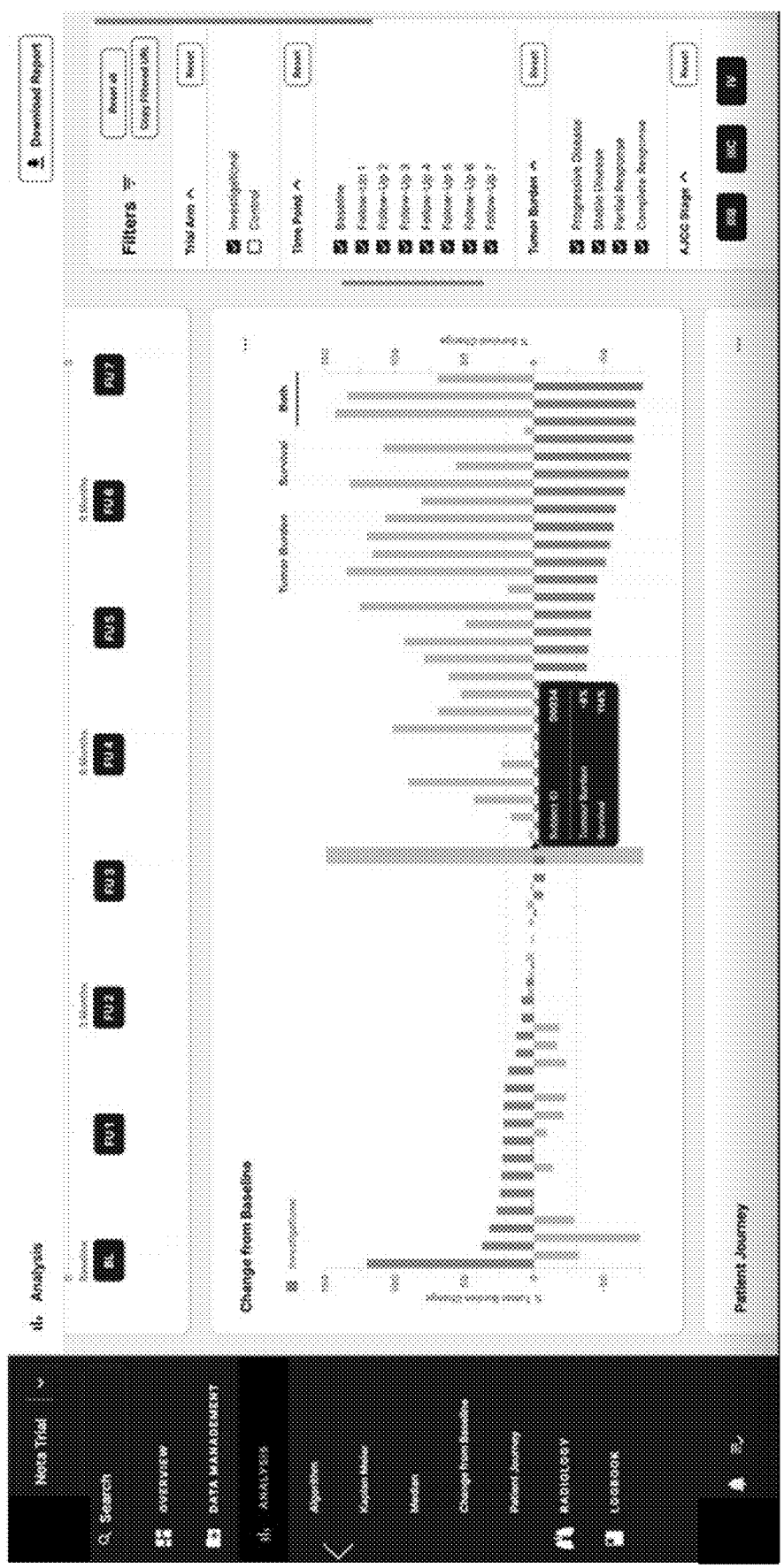

FIG. 3H is an illustrative embodiment of a GUI 300H. The GUI 300H can serve as an illustrative embodiment of a user interface that can be accessed or selectively accessed by various devices to provide various information to various individuals, such as patients, healthcare providers, clinical trial managers, pharmaceutical companies, and so forth. GUI 300H provides information regarding changes to both predicted survival and tumor burden, such as for the investigational arm patients. For example, the subject ID 00034 is predicted to survive 114% longer than their baseline prediction and an 8% decrease in tumor burden based on applying the image-based model to the most recent image for the patient. In one or more embodiments, GUI 300H allows access directly into CT scans or other images of the patient whose data is being reviewed. In one embodiment, GUI 300H can also selectively provide predicted survival information, tumor burden information and/or changes from baseline for the control arm.

Figure 3I:
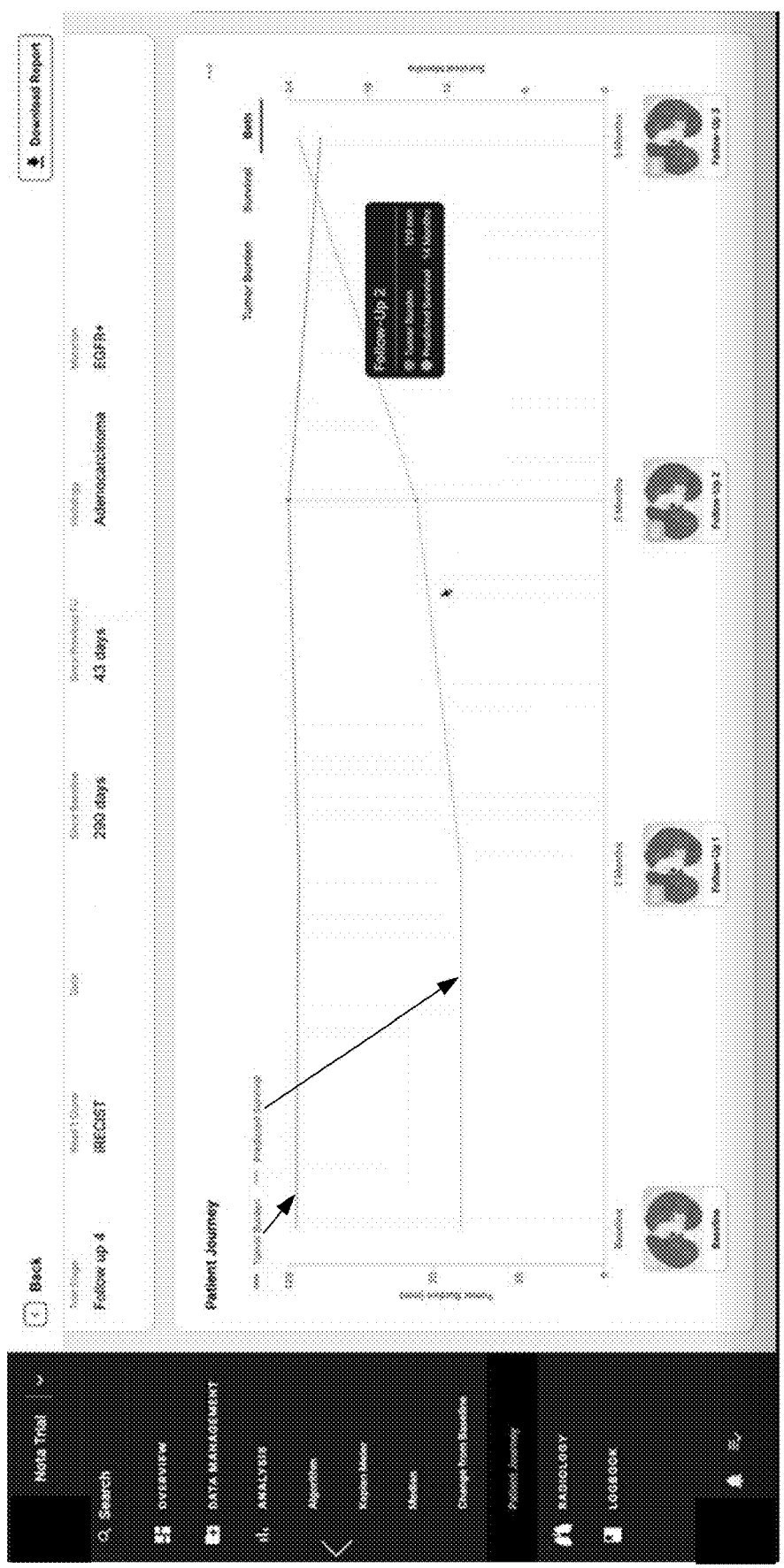

FIG. 3I is an illustrative embodiment of a GUI 300I. The GUI 300I can serve as an illustrative embodiment of a user interface that can be accessed or selectively accessed by various devices to provide various information to various individuals, such as patients, healthcare providers, clinical trial managers, pharmaceutical companies, and so forth. GUI 300I provides a patients journey with relevant data over the treatment time period including tumor burden, baseline/pre-treatment and follow-up images, and survival data. In one embodiment of GUI 300I, portions of the relevant data provided in the patient's journey is predicted data (predicted survival, predicted tumor size, and so forth).

Figure 3J:

FIG. 3J is a case study 300J indicating outcome variability between two patients having similar characteristics (e.g., lung squamous cell carcinoma (SqCC), stage (T/N/M) being 1A (1/0/0), age 65, males, ECOG 0, similar BMI, surgical treatment). However, patient A survived greater than 61 months while patient B survived 9 months. Consistent with the survival data, the image-based model as described herein being applied to baseline/pre-treatment images (activation maps of which are shown in FIG. 3J) accurately quantifies risk for patient A as low (2/10) and risk for patient B as high (9/10).

FIG. 3K is a case study 300K indicating outcome variability between two patients having similar characteristics (e.g., non-small cell lung cancer (NSCLC), stage IIIB, age 72, ECOG 0, chemotherapy treatment). However, patient A survived 40 months while patient B survived 13 months. Consistent with the survival data, the image-based model as described herein being applied to baseline/pre-treatment images (activation maps of which are shown in FIG. 3K) accurately quantifies risk for patient A as low (2/10) and risk for patient B as high (10/10).

FIG. 3L is a case study 300L indicating outcome variability between two patients having similar characteristics (e.g., NSCLC, stage IIIB, age 67, males, smoking history, ECOG 0, chemotherapy treatment). However, patient A survived greater than 71 months while patient B survived 9 months. Consistent with the survival data, the image-based model as described herein being applied to baseline/pre-treatment images (activation maps of which are shown in FIG. 3L) accurately quantifies risk for patient A as low (4/10) and risk for patient B as high (10/10).

Figure 3M:
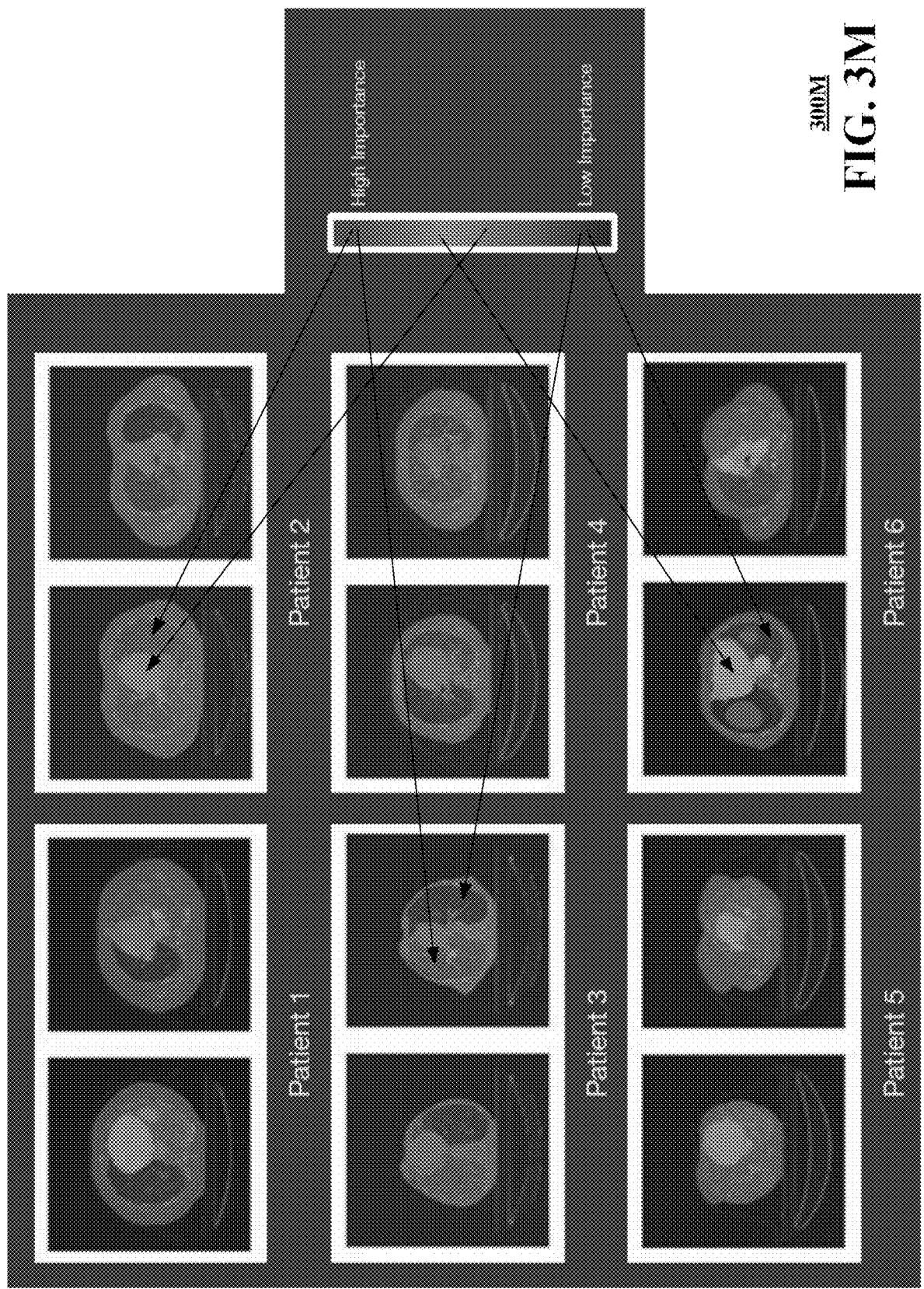
FIG. 3M illustrates an activation or attention map for different patients generated in accordance with various aspects described herein.

FIG. 3M is an illustrative example of attention heatmaps or activation maps generated for different patients where the weighting applied by the exemplary image-based model is determined and indicated for the entire organ rather than for the particular pixels or areas within the organ (see FIG. 2K). As explained herein, in one or more embodiments, activation maps can be generated by the modeling platform to indicate organ segmentation illustrating prognostic importance to the image-based model. In this example, the activation maps can indicate that the image-based model has placed attention on the correct organ(s). In other embodiments where the activation maps show weighting for particular pixels or areas within the organ (see e.g., FIG. 2K), the activation maps can be generated to indicate that the image-based model has weighted tumors and peritumoral tissue heavily even though the image-based model was not trained to focus on tumors.

Figure 3N:
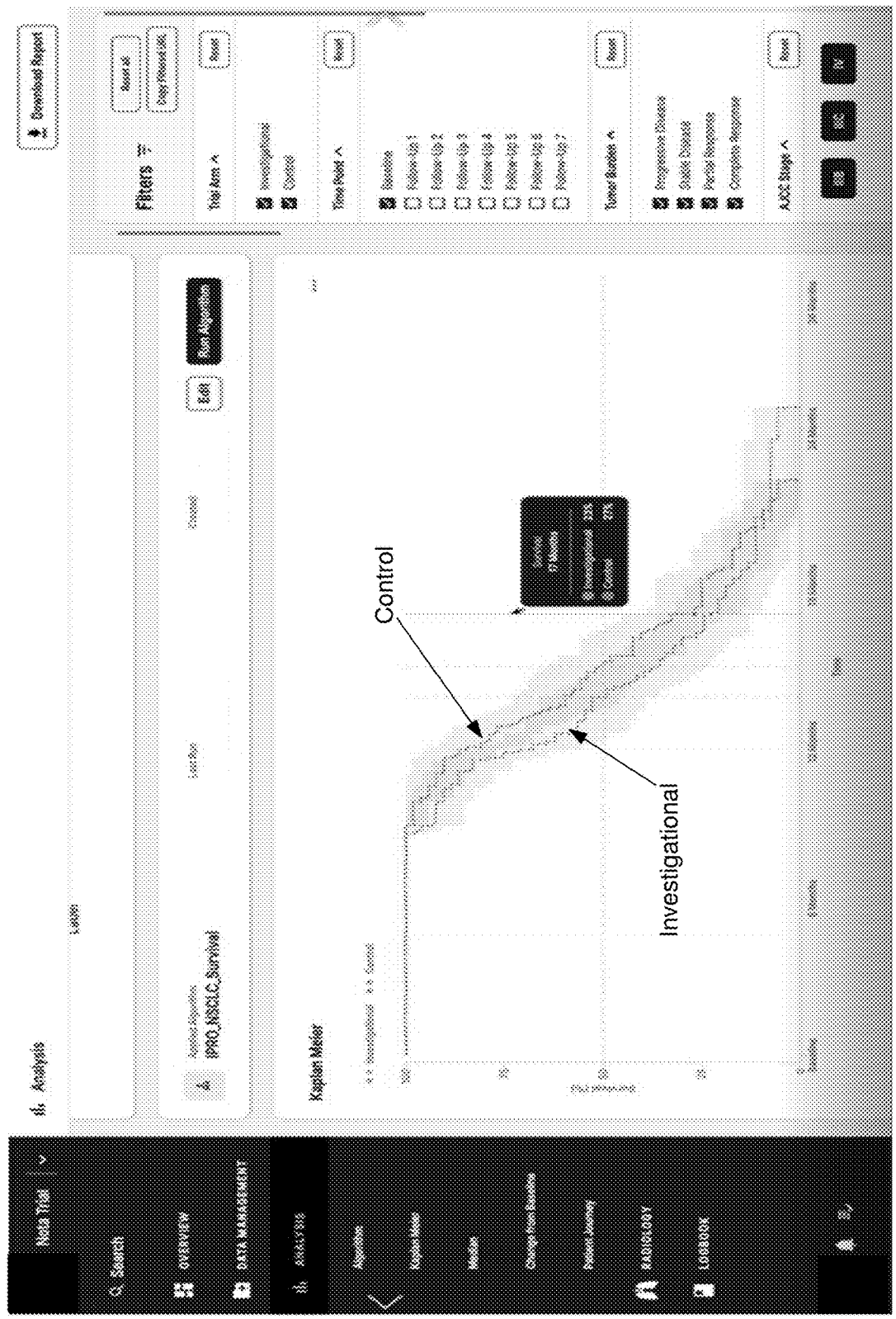
Figure 30:
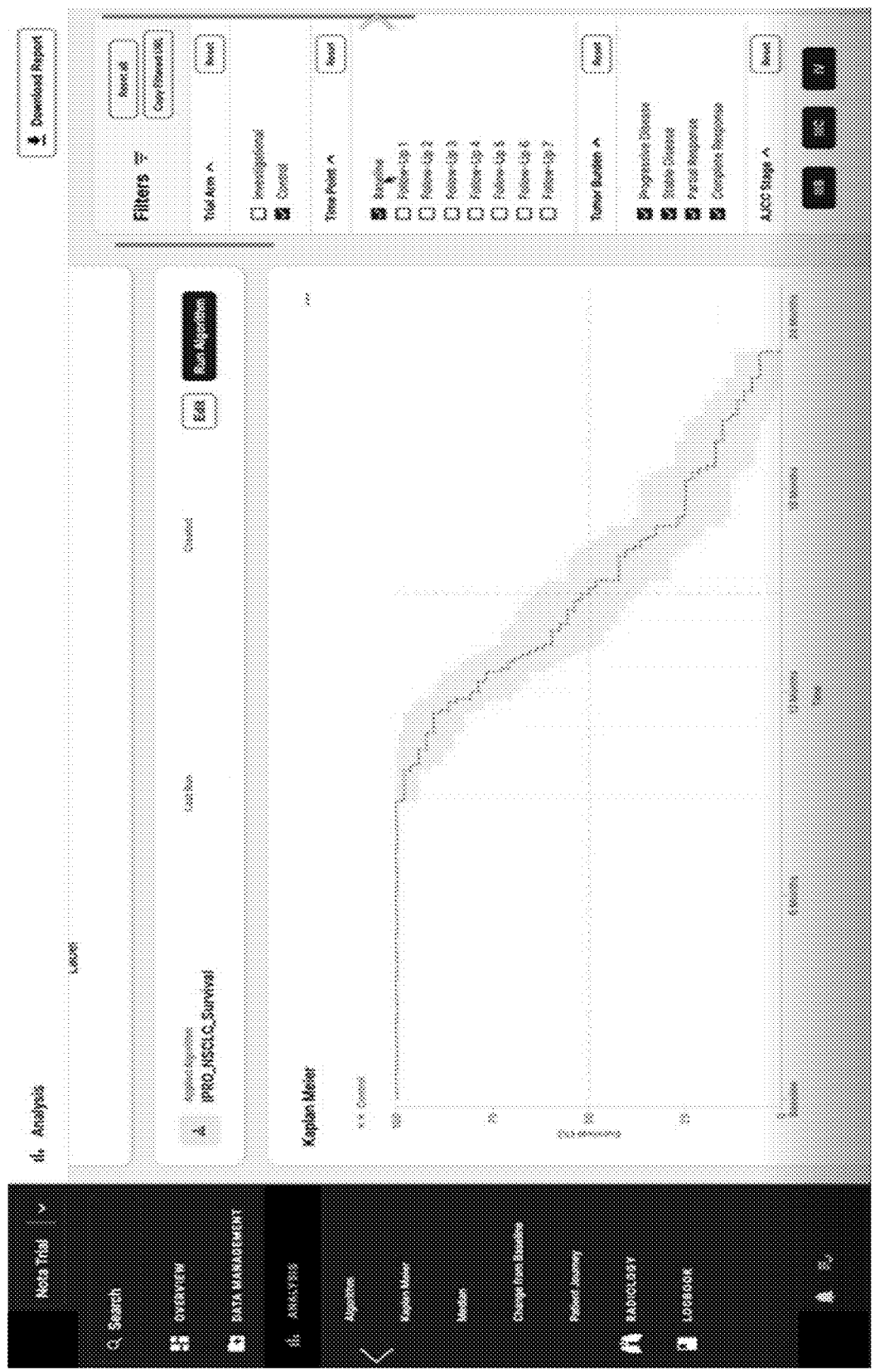

FIG. 3N is an illustrative embodiment of a GUI 300N. The GUI 300N can serve as an illustrative embodiment of a user interface that can be accessed or selectively accessed by various devices to provide various information to various individuals, such as patients, healthcare providers, clinical trial managers, pharmaceutical companies, and so forth. In this example, the user/viewer can be one or more individuals of the clinical manager, sponsor, or pharmaceutical company associated with management of the clinical trial. Continuing with this example, the clinical trial has already commenced. Based on the KM curves for the investigational arm and the control arm (which have been generated according to the application of the image-based model to the baseline/pre-treatment CT scans (which is indicated by the selection mark for the baseline button under Time Point)), an imbalance in the clinical trial exists. In this instance, this particular KM curve is showing that the control arm is predicted to survive longer than the treatment arm, which may be a result of an imperfect or erroneous randomization (e.g., healthier patients were utilized in the control arm as compared to the investigational arm). GUI 300N allows quantification and/or visualization of the error in randomization (e.g., the difference between the KM curves such as at baseline). This quantification allows the clinical managers or other entities looking at the data to better understand the results, such as at the end of the trial, when comparing the actual survival of the treatment arm and the control arm, so that the imbalance can be taken into account. As described with respect to process 201E of FIG. 2E, the modeling platform also prevents or reduces this error by allowing for balanced randomization such that the investigational arm and the control arm can be properly balanced according to the predictions from application of the image-based model to the baseline/pre-treatment CT scans.

Figure 3P:
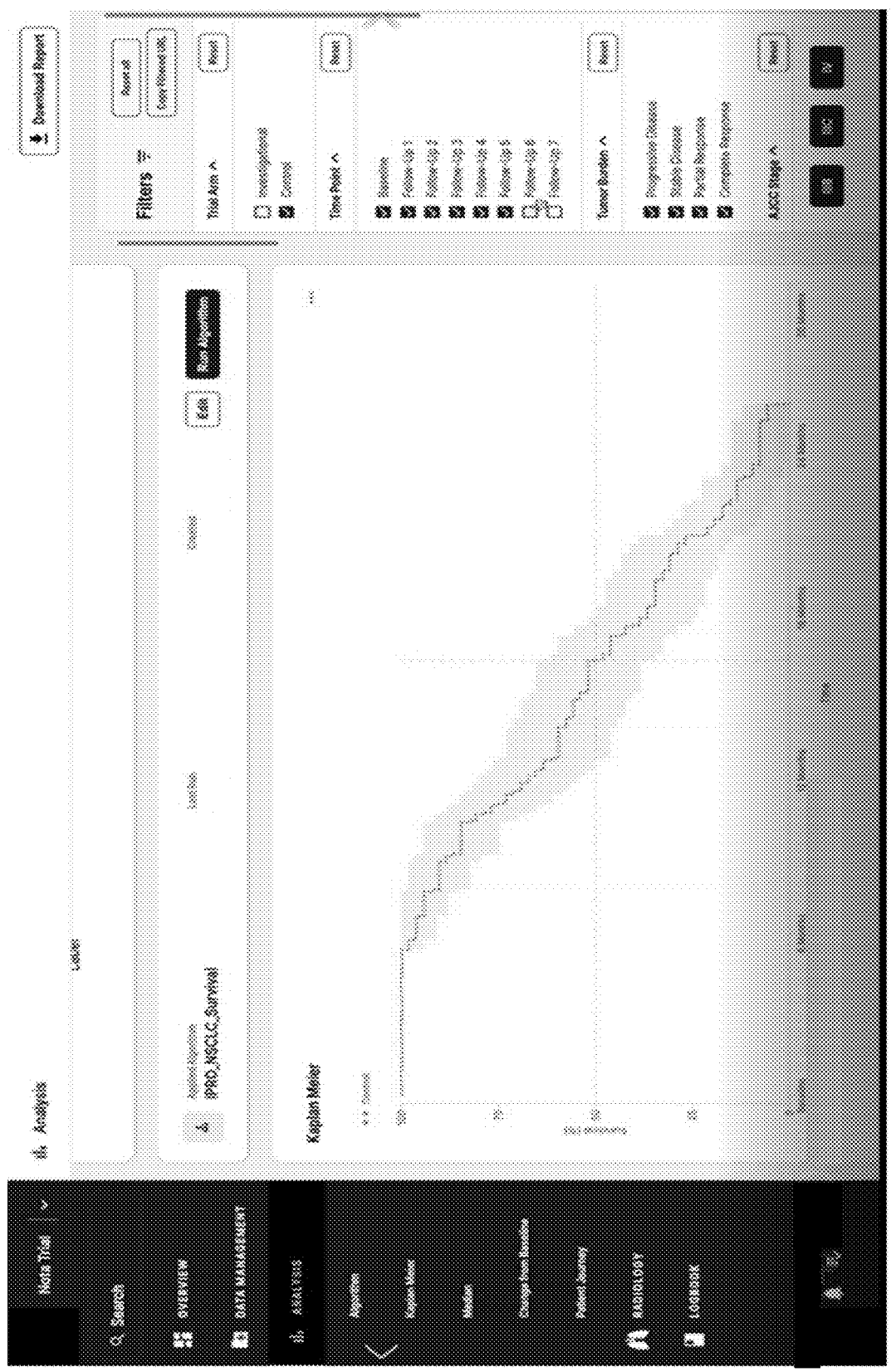
Figure 3Q:
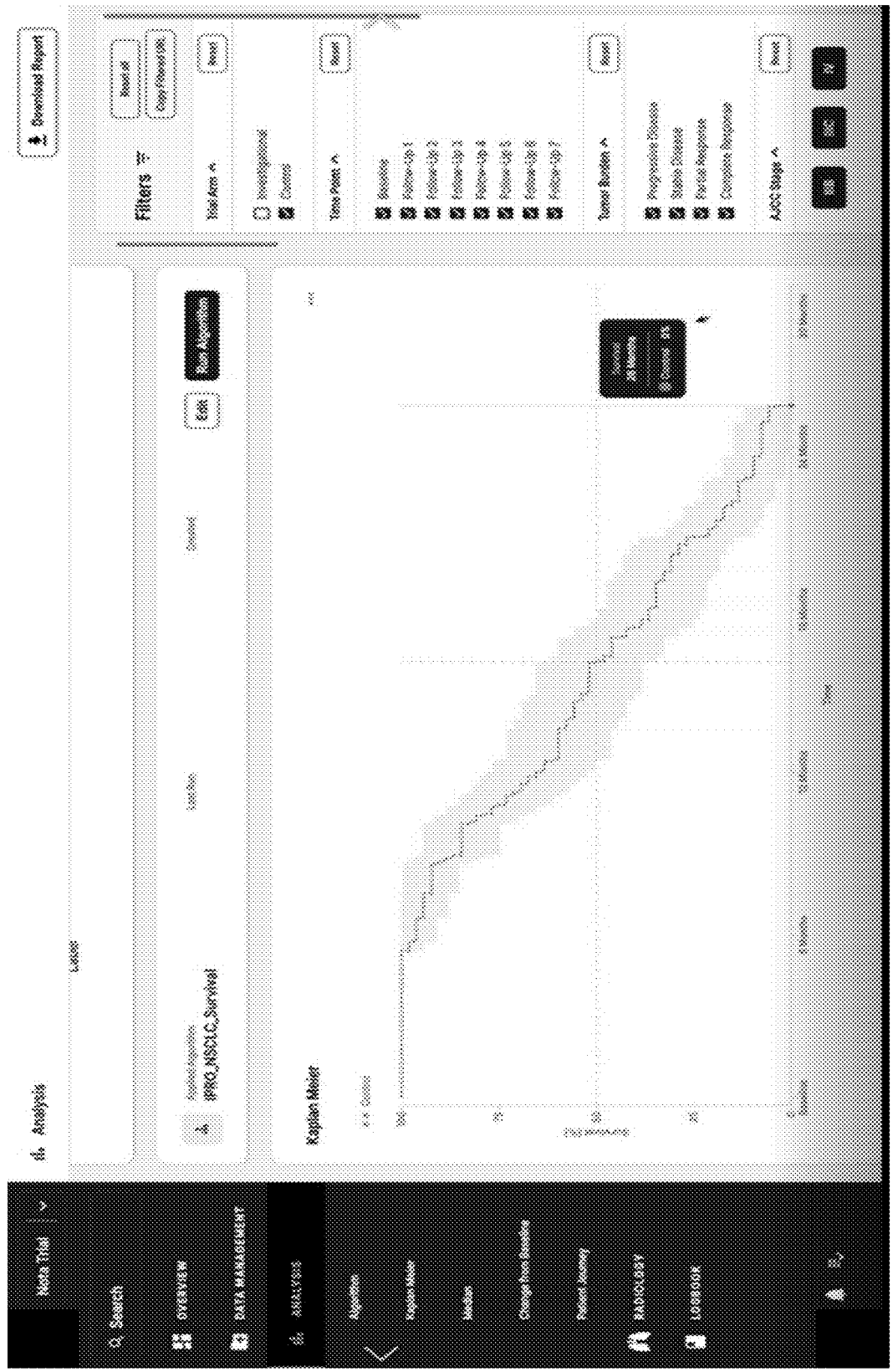

FIGS. 3O-3Q are illustrative embodiments of GUIs 300O, 300P, 300Q. The GUIs 300O, 300P, 300Q can serve as illustrative embodiments of user interfaces that can be accessed or selectively accessed by various devices to provide various information to various individuals, such as patients, healthcare providers, clinical trial managers, pharmaceutical companies, and so forth. GUI 300O shows a KM curve generated for the control arm according to predictions made from the application of the image-based model to the baseline/pre-treatment CT scans. As more follow-up scans are obtained and ingested, the predictions of the control arm can be updated (according to the application of the image-based model to the most recent follow-up CT scans) and the KM curves will then adjust or change as illustrated by the differences in the KM curves presented by GUI 300P (i.e., follow-up images five) as compared to GUI 300Q (follow-up images seven). Other types of event estimation information can be generated or otherwise predicted including time-to-event information, survival data, and so forth.

Figure 3R:
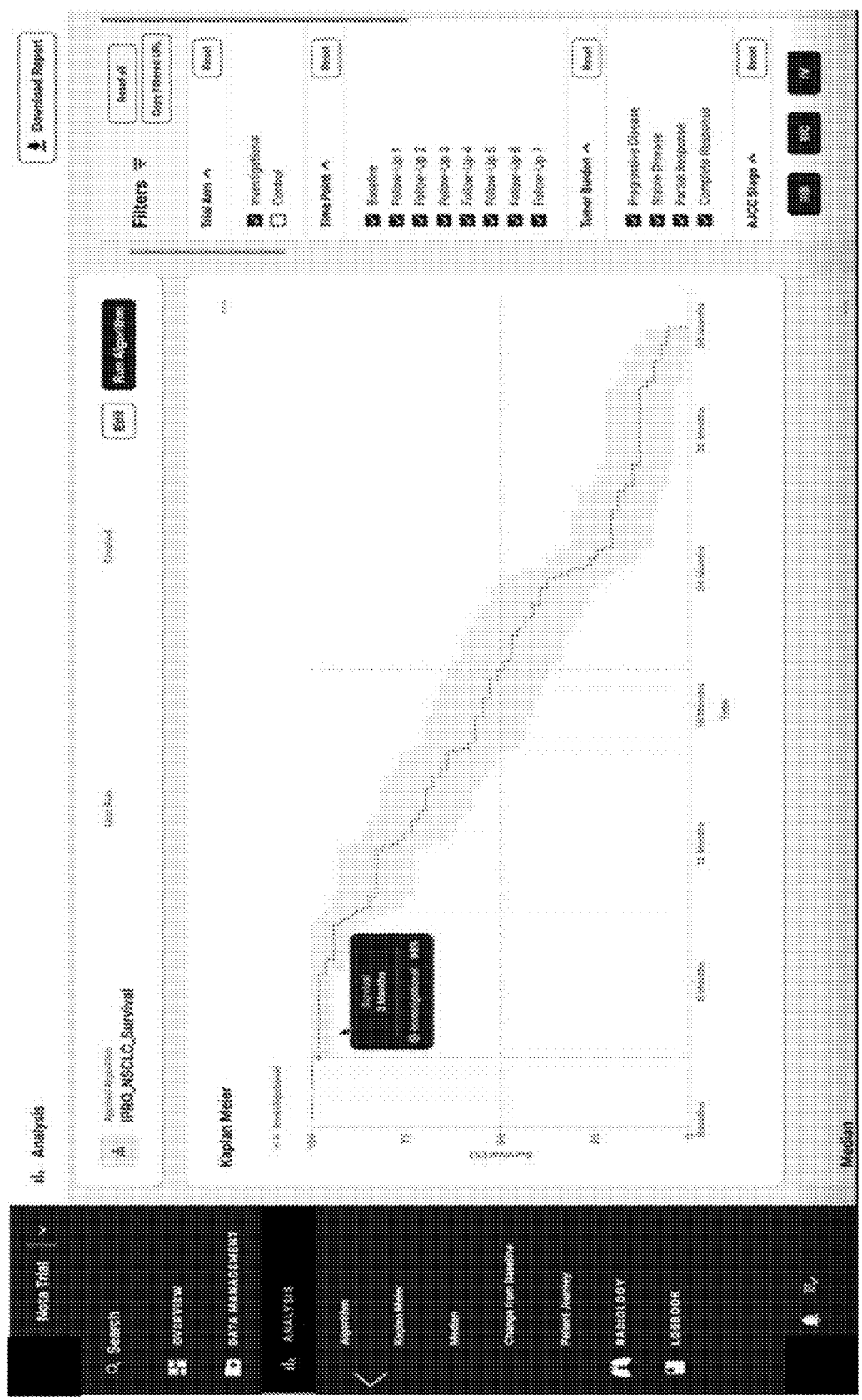

FIG. 3R is an illustrative embodiment of a GUI 300R. The GUI 300R can serve as an illustrative embodiment of a user interface that can be accessed or selectively accessed by various devices to provide various information to various individuals, such as patients, healthcare providers, clinical trial managers, pharmaceutical companies, and so forth. As an example, GUI 300R can be a trial view that provides access to event estimation information such as KM curves (as well as other generated data). In this example, the KM curves are generated according to predictions that are determined by the image-based model applied to the most recent follow-up image for each patient of the clinical trial. The selection of the investigational arm causes the GUI 300R to present the KM curve for the investigational arm that was generated according to predictions made from the image-based model as applied to the follow-up seven images.

In one or more embodiments, one, some, or all of the functions described herein can be performed in conjunction with a virtualized communication network. For example, a virtualized communication network can facilitate in whole or in part providing image-based modeling and a modeling platform to assist in clinical trials, healthcare treatment or other health-related events, such as through presenting predictive variables for a treatment at different future time periods. In particular, a cloud networking architecture can leverage cloud technologies and support rapid innovation and scalability such as via a transport layer, a virtualized network function cloud and/or one or more cloud computing environments. In various embodiments, this cloud networking architecture can be an open architecture that leverages application programming interfaces (APIs); reduces complexity from services and operations; supports more nimble business models; and rapidly and seamlessly scales to meet evolving customer requirements including traffic growth, diversity of traffic types, and diversity of performance and reliability expectations. For example, the virtualized communication network can employ virtual network elements (VNEs) that perform some or all of the functions of traditional network elements such as providing a substrate of networking capability, (e.g., Network Function Virtualization Infrastructure (NFVI)) or infrastructure that is capable of being directed with software and Software Defined Networking (SDN) protocols to perform a broad variety of network functions and services.

Figure 4:
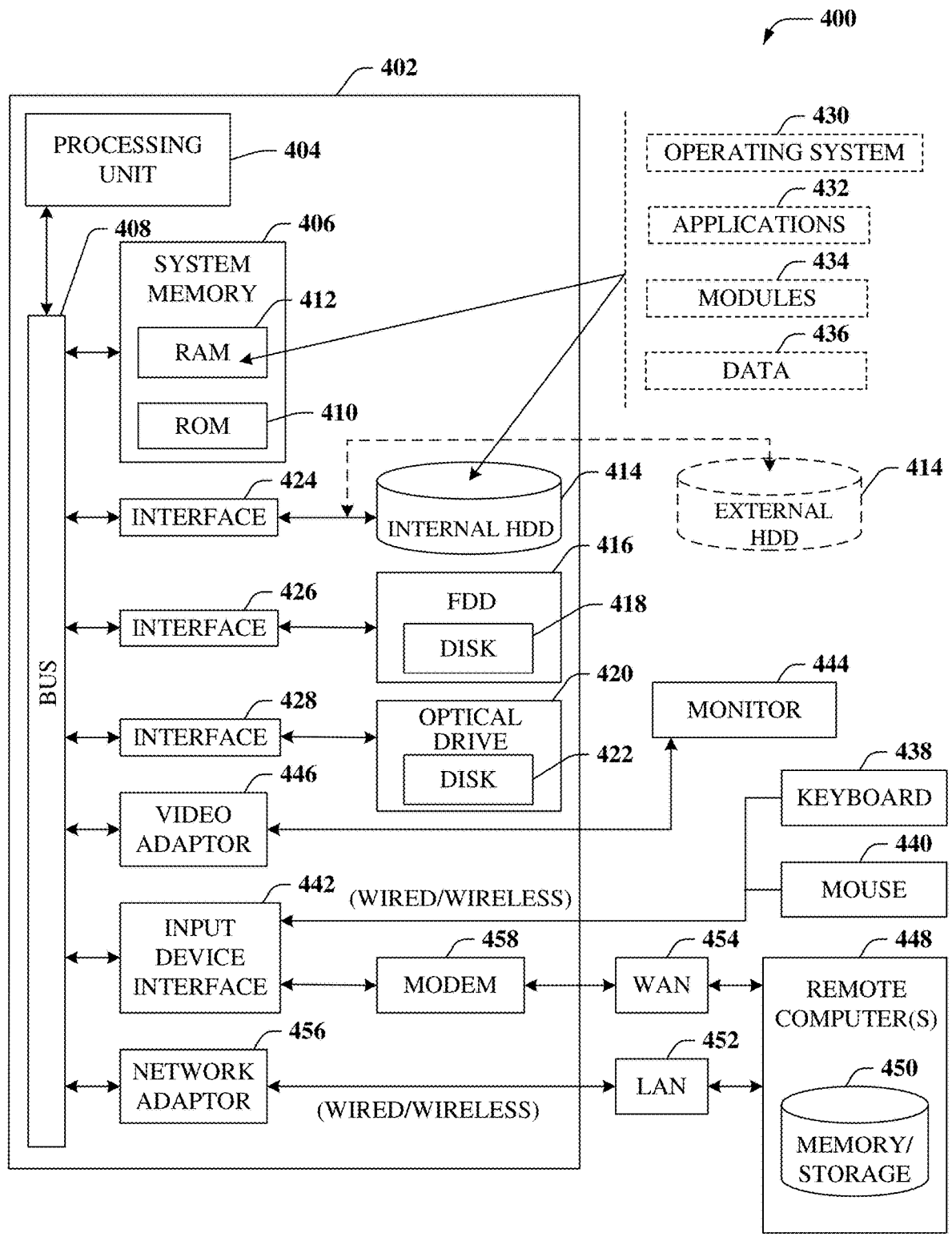
FIG. 4 is a block diagram of an example, non-limiting embodiment of a computing environment in accordance with various aspects described herein.

Turning now to FIG. 4, there is illustrated a block diagram of a computing environment in accordance with various aspects described herein. In order to provide additional context for various embodiments of the embodiments described herein, FIG. 4 and the following discussion are intended to provide a brief, general description of a suitable computing environment 400 in which the various embodiments of the subject disclosure can be implemented. Each of these devices can be implemented via computer-executable instructions that can run on one or more computers, and/or in combination with other program modules and/or as a combination of hardware and software. For example, computing environment 400 can facilitate in whole or in part providing image-based modeling and a modeling platform to assist in clinical trials, healthcare treatment or other health-related events, such as through presenting predictive variables for a treatment at different future time periods.

Generally, program modules comprise routines, programs, components, data structures, etc., that perform particular tasks or implement particular abstract data types. Moreover, those skilled in the art will appreciate that the methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

As used herein, a processing circuit includes one or more processors as well as other application specific circuits such as an application specific integrated circuit, digital logic circuit, state machine, programmable gate array or other circuit that processes input signals or data and that produces output signals or data in response thereto. It should be noted that while any functions and features described herein in association with the operation of a processor could likewise be performed by a processing circuit.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 4, the example environment can comprise a computer 402, the computer 402 comprising a processing unit 404, a system memory 406 and a system bus 408. The system bus 408 couples system components including, but not limited to, the system memory 406 to the processing unit 404. The processing unit 404 can be any of various commercially available processors. Dual microprocessors and other multiprocessor architectures can also be employed as the processing unit 404.

The system bus 408 can be any of several types of bus structure that can further interconnect to a memory bus (with or without a memory controller), a peripheral bus, and a local bus using any of a variety of commercially available bus architectures. The system memory 406 comprises ROM 410 and RAM 412. A basic input/output system (BIOS) can be stored in a non-volatile memory such as ROM, erasable programmable read only memory (EPROM), EEPROM, which BIOS contains the basic routines that help to transfer information between elements within the computer 402, such as during startup. The RAM 412 can also comprise a high-speed RAM such as static RAM for caching data.

The computer 402 further comprises an internal hard disk drive (HDD) 414 (e.g., EIDE, SATA), which internal HDD 414 can also be configured for external use in a suitable chassis (not shown), a magnetic floppy disk drive (FDD) 416, (e.g., to read from or write to a removable diskette 418) and an optical disk drive 420, (e.g., reading a CD-ROM disk 422 or, to read from or write to other high capacity optical media such as the DVD). The HDD 414, magnetic FDD 416 and optical disk drive 420 can be connected to the system bus 408 by a hard disk drive interface 424, a magnetic disk drive interface 426 and an optical drive interface 428, respectively. The hard disk drive interface 424 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 402, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 412, comprising an operating system 430, one or more application programs 432, other program modules 434 and program data 436. All or portions of the operating system, applications, modules, and/or data can also be cached in the RAM 412. The systems and methods described herein can be implemented utilizing various commercially available operating systems or combinations of operating systems.

A user can enter commands and information into the computer 402 through one or more wired/wireless input devices, e.g., a keyboard 438 and a pointing device, such as a mouse 440. Other input devices (not shown) can comprise a microphone, an infrared (IR) remote control, a joystick, a game pad, a stylus pen, touch screen or the like. These and other input devices are often connected to the processing unit 404 through an input device interface 442 that can be coupled to the system bus 408, but can be connected by other interfaces, such as a parallel port, an IEEE 1394 serial port, a game port, a universal serial bus (USB) port, an IR interface, etc.

A monitor 444 or other type of display device can be also connected to the system bus 408 via an interface, such as a video adapter 446. It will also be appreciated that in alternative embodiments, a monitor 444 can also be any display device (e.g., another computer having a display, a smart phone, a tablet computer, etc.) for receiving display information associated with computer 402 via any communication means, including via the Internet and cloud-based networks. In addition to the monitor 444, a computer typically comprises other peripheral output devices (not shown), such as speakers, printers, etc.

The computer 402 can operate in a networked environment using logical connections via wired and/or wireless communications to one or more remote computers, such as a remote computer(s) 448. The remote computer(s) 448 can be a workstation, a server computer, a router, a personal computer, portable computer, microprocessor-based entertainment appliance, a peer device or other common network node, and typically comprises many or all of the elements described relative to the computer 402, although, for purposes of brevity, only a remote memory/storage device 450 is illustrated. The logical connections depicted comprise wired/wireless connectivity to a local area network (LAN) 452 and/or larger networks, e.g., a wide area network (WAN) 454. Such LAN and WAN networking environments are commonplace in offices and companies, and facilitate enterprise-wide computer networks, such as intranets, all of which can connect to a global communications network, e.g., the Internet.

When used in a LAN networking environment, the computer 402 can be connected to the LAN 452 through a wired and/or wireless communication network interface or adapter 456. The adapter 456 can facilitate wired or wireless communication to the LAN 452, which can also comprise a wireless AP disposed thereon for communicating with the adapter 456.

When used in a WAN networking environment, the computer 402 can comprise a modem 458 or can be connected to a communications server on the WAN 454 or has other means for establishing communications over the WAN 454, such as by way of the Internet. The modem 458, which can be internal or external and a wired or wireless device, can be connected to the system bus 408 via the input device interface 442. In a networked environment, program modules depicted relative to the computer 402 or portions thereof, can be stored in the remote memory/storage device 450. It will be appreciated that the network connections shown are example and other means of establishing a communications link between the computers can be used.

The computer 402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, ag, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands for example or with products that contain both bands (dual band), so the networks can provide real-world performance similar to the basic 10BaseT wired Ethernet networks used in many offices.

The terms "first," "second," "third," and so forth, as used in the claims, unless otherwise clear by context, is for clarity only and doesn't otherwise indicate or imply any order in time. For instance, "a first determination," "a second determination," and "a third determination," does not indicate or imply that the first determination is to be made before the second determination, or vice versa, etc.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory, non-volatile memory, disk storage, and memory storage. Further, non-volatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, smartphone, watch, tablet computers, netbook computers, etc.), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

In one or more embodiments, information regarding use of services can be generated including services being accessed, media consumption history, user preferences, and so forth. This information can be obtained by various methods including user input, detecting types of communications (e.g., video content vs. audio content), analysis of content streams, sampling, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

Some of the embodiments described herein can also employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of each cell site of the acquired network. A classifier is a function that maps an input attribute vector, $x=(x1, x2, x3, x4 \ldots, xn)$, to a confidence that the input belongs to a class, that is, $f(x)$ =confidence (class). Such classification can employ a probabilistic and/or statistical-based analysis (e.g., factoring into the analysis utilities and costs) to determine or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to predetermined criteria which of the acquired cell sites will benefit a maximum number of subscribers and/or which of the acquired cell sites will add minimum value to the existing communication network coverage, etc.

As used in some contexts in this application, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/communications media. For example, computer readable storage media can include, but are not limited to, magnetic storage devices (e.g., hard disk, floppy disk, magnetic strips), optical disks (e.g., compact disk (CD), DVD), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an"

as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer." "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

As used herein, terms such as "data storage," data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

As may also be used herein, the term(s) "operably coupled to", "coupled to", and/or "coupling" includes direct coupling between items and/or indirect coupling between items via one or more intervening items. Such items and intervening items include, but are not limited to, junctions, communication paths, components, circuit elements, circuits, functional blocks, and/or devices. As an example of indirect coupling, a signal conveyed from a first item to a second item may be modified by one or more intervening items by modifying the form, nature or format of information in a signal, while one or more elements of the information in the signal are nevertheless conveyed in a manner than can be recognized by the second item. In a further example of indirect coupling, an action in a first item can cause a reaction on the second item, as a result of actions and/or reactions in one or more intervening items.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

What is claimed is:

1. A method, comprising:
obtaining, by a processing system including a processor, a pre-treatment image for a patient that is to be subject to treatment for a disease, the pre-treatment image capturing at least an organ that is to be subject to the treatment, the pre-treatment image being captured prior to the treatment;
analyzing, by the processing system, the pre-treatment image according to an imaging model that is a machine learning model, wherein the imaging model is trained based on ingesting other images of the organ for individuals and based on survival rate data for the individuals, wherein the individuals corresponding to the other images underwent the treatment, and wherein the imaging model is not trained to focus on tumors;
predicting, by the processing system and according to the analyzing of the pre-treatment image, one or more clinical variables for the pre-treatment image resulting in a predicted variable;
generating, by the processing system, a graphical user interface that includes event estimation information based at least in part on the predicted variable, wherein the event estimation information includes one of time-to-event curves, survival curves, Kaplan-Meier curves, or a combination thereof; and
providing, by the processing system, equipment of a healthcare provider of the patient with access to the graphical user interface.

2. The method of claim 1, comprising:
obtaining, by the processing system, an image for the patient resulting in an on-treatment image, the on-treatment image being associated with a time period of the treatment;
analyzing, by the processing system, the on-treatment image according to the imaging model;
predicting, by the processing system based on the analyzing of the on-treatment image, the one or more clinical variables for the on-treatment image resulting in a predicted on-treatment variable;
generating, by the processing system, revised event estimation information based at least in part on the predicted on-treatment variable; and
providing, by the processing system, the revised event estimation information in the graphical user interface that is accessible to the equipment of the healthcare provider of the patient.

3. The method of claim 2, wherein the graphical user interface includes a predicted image of the organ at a future time that is generated based on the analyzing the pre-treatment image, the analyzing the on-treatment image, the predicted variable, the predicted on-treatment variable, or a combination thereof.

4. The method of claim 2, wherein the predicted on-treatment variable includes survival data, an Imaging-Based Prognostication (IPRO) score, tumor size, tumor response, or a combination thereof.

5. The method of claim 2, wherein the pre-treatment image and the on-treatment image include 3D Computed Tomography (CT) images, wherein the imaging model includes a 3D convolutional neural network (3DCNN), and wherein the other images of the individuals include 3D CT images.

6. The method of claim 5, wherein the pre-treatment image, the on-treatment image, and the other images undergo 3D segmentation to capture a total volume that is greater than the organ and includes a surrounding volume around at least a portion of the organ, wherein the imaging model is trained based in part on the surrounding volume, and wherein the analyzing the pre-treatment image according to the imaging model includes an analysis of the surrounding volume.

7. The method of claim 2, comprising:
repeating, by the processing system, the obtaining of the image for the patient at different time periods of the treatment resulting in a set of on-treatment images;
repeating, by the processing system, the analyzing the set of on-treatment images according to the imaging model;
repeating, by the processing system and based on the analyzing of the sets of on-treatment images, the pre-dicting the one or more clinical variables for the set of on-treatment images resulting in a predicted set of on-treatment variables;
repeating, by the processing system, the generating revised event estimation information based at least in part on the predicted set of on-treatment variables;
providing, by the processing system, an option in the graphical user interface for selecting one or more time periods of the different time periods of the treatment;
receiving, by the processing system, a user input that selects at least one time period; and
providing, by the processing system, the revised event estimation information in the graphical user interface that is accessible to the equipment of the healthcare provider of the patient corresponding to the at least one time period.

8. The method of claim 7, comprising:
obtaining an image for the patient after treatment has concluded resulting in a post-treatment image;
analyzing the post-treatment image according to the imaging model;
predicting, based on the analyzing of the post-treatment image, one or more clinical variables for the post-treatment image resulting in predicted post-treatment variables; and
generating event estimation curves based on the predicted post-treatment variables, wherein the different time periods of the treatment include a post-treatment time period, wherein the predicted variable includes age, sex, weight, Eastern Cooperative Oncology Group (ECOG) status, smoking status, competing mortality risk, cardiac and pulmonary toxicity, TNM (Tumor, Nodes and Metastases) stage, pulmonary function, or a combination thereof.

9. The method of claim 1, comprising:
generating, by the processing system and based at least on the predicted variable, a digital twin for the patient.

10. A device, comprising:
a processing system including a processor; and
a memory that stores executable instructions that, when executed by the processing system, facilitate performance of operations, the operations comprising:
obtaining a pre-treatment image for a patient that is to be subject to treatment for a disease, the pre-treatment image capturing at least an organ that is to be subject to the treatment, the pre-treatment image being captured prior to the treatment;
analyzing the pre-treatment image according to an imaging model that is a machine learning model, wherein the imaging model is trained based on ingesting other images of the organ for individuals and based on survival rate data for the individuals;
predicting, according to the analyzing of the pre-treatment image, one or more clinical variables for the pre-treatment image resulting in a predicted variable;
generating event estimation information based at least in part on the predicted variable;
obtaining images for the patient at different time periods of the treatment resulting in a set of on-treatment images;
analyzing the set of on-treatment images according to the imaging model;
predicting, based on the analyzing of the sets of on-treatment images, the one or more clinical variables for the set of on-treatment images resulting in a predicted set of on-treatment variables;

generating revised event estimation information based at least in part on the predicted set of on-treatment variables;
generating a graphical user interface;
providing equipment of a healthcare provider of the patient with access to the graphical user interface;
providing an option in the graphical user interface for selecting one or more time periods of the different time periods of the treatment;
receiving a user input that selects at least one time period; and
providing the event estimation information or the revised event estimation information in the graphical user interface that is accessible to the equipment of the healthcare provider of the patient corresponding to the at least one time period.

11. The device of claim 10 wherein the graphical user interface includes a predicted image of the organ at a future time that is generated based on the analyzing the pre-treatment image, the analyzing the set of on-treatment images, the predicted variable, the predicted set of on-treatment variables, or a combination thereof.

12. The device of claim 10, wherein the pre-treatment image and the set of on-treatment images include 3D Computed Tomography (CT) images, wherein the imaging model includes a 3D convolutional neural network (3DCNN), and wherein the other images of the individuals include 3D CT images.

13. The device of claim 12, wherein the pre-treatment image, the set of on-treatment images, and the other images undergo 3D segmentation to capture a total volume that is greater than the organ and includes a surrounding volume around at least a portion of the organ, wherein the imaging model is trained based in part on the surrounding volume, and wherein the analyzing the pre-treatment image or the set of on-treatment images according to the imaging model includes an analysis of the surrounding volume.

14. The device of claim 10, wherein the individuals corresponding to the other images underwent the treatment, wherein the imaging model is not trained to focus on tumors, and wherein the event estimation information includes one of time-to-event curves, survival curves, Kaplan-Meier curves, or a combination thereof.

15. The device of claim 10, wherein the operations further comprise:
obtaining an image for the patient after treatment has concluded resulting in a post-treatment image;
analyzing the post-treatment image according to the imaging model;
predicting, based on the analyzing of the post-treatment image, one or more clinical variables for the post-treatment image resulting in predicted post-treatment variables; and
generating event estimation curves based on the predicted post-treatment variables, wherein the different time periods of the treatment include a post-treatment time period,
wherein the predicted variable includes age, sex, weight, Eastern Cooperative Oncology Group (ECOG) status, smoking status, competing mortality risk, cardiac and pulmonary toxicity, TNM (Tumor, Nodes and Metastases) stage, pulmonary function tests, or a combination thereof.

16. The device of claim 10, wherein the operations further comprise:
generating, based at least on the predicted variable, a digital twin for the patient.

17. A non-transitory machine-readable medium, comprising executable instructions that, when executed by a processing system including a processor, facilitate performance of operations, the operations comprising:
generating a graphical user interface that is configured to selectively present event estimation information and revised event estimation information for a patient associated with treatment for a disease of an organ, wherein the event estimation information is generated based on a predicted variable determined from analyzing a pre-treatment image of the patient according to an imaging model that includes a machine learning model, wherein the pre-treatment image captures at least an organ prior to the treatment, wherein the imaging model is trained based on ingesting other images of the organ for individuals and based on survival rate data for the individuals, wherein the analyzing of the pre-treatment image predicts one or more clinical variables for the pre-treatment image resulting in the predicted variable, wherein the revised event estimation information is generated based on a predicted set of on-treatment variables determined from analyzing a set of on-treatment images of the patient according to the imaging model, wherein the set of on-treatment images captures at least the organ at different time periods of the treatment, wherein the analyzing of the set of on-treatment images predicts the one or more clinical variables for the set of on-treatment images resulting in the predicted set of on-treatment variables;
providing equipment of a healthcare provider of the patient with access to the graphical user interface;
providing an option in the graphical user interface for selecting one or more time periods of the different time periods of the treatment;
receiving a user input that selects at least one time period; and
providing the event estimation information or the revised event estimation information in the graphical user interface that is accessible to the equipment of the healthcare provider of the patient corresponding to the at least one time period.

18. The non-transitory machine-readable medium of claim 17, wherein the graphical user interface includes a predicted image of the organ at a future time that is generated based on the analyzing the pre-treatment image, the analyzing the set of on-treatment images, the predicted variable, the predicted set of on-treatment variables, or a combination thereof.

19. The non-transitory machine-readable medium of claim 17, wherein the pre-treatment image and the set of on-treatment images include 3D Computed Tomography (CT) images, wherein the imaging model includes a 3D convolutional neural network (3DCNN), wherein the other images of the individuals include 3D CT images, wherein the pre-treatment image, the set of on-treatment images, and the other images undergo 3D segmentation to capture a total volume that is greater than the organ and includes a surrounding volume around at least a portion of the organ, wherein the imaging model is trained based in part on the surrounding volume, wherein the analyzing the pre-treatment image or the set of on-treatment images according to the imaging model includes an analysis of the surrounding volume, wherein the event estimation information includes one of time-to-event curves, survival curves, Kaplan-Meier curves, or a combination thereof.

* * * * *